(12) United States Patent
Hickey et al.

(10) Patent No.: US 7,235,566 B2
(45) Date of Patent: Jun. 26, 2007

(54) PYRIDINONE DERIVATIVES FOR TREATMENT OF ATHEROSCLEROSIS

(75) Inventors: Deirdre Mary Bernadette Hickey, Stevenage (GB); Robert John Ife, Stevenage (GB); Colin Andrew Leach, King of Prussia, PA (US); John Liddle, Stevenage (GB); Ivan Leo Pinto, Stevenage (GB); Stephen Allan Smith, Stevenage (GB); Steven James Stanway, Harlow (GB)

(73) Assignee: Smithkline Beecham p.l.c. (GB)

( * ) Notice: Subject to any disclaimer, the term of this patent is extended or adjusted under 35 U.S.C. 154(b) by 0 days.

(21) Appl. No.: 10/900,489

(22) Filed: Jul. 28, 2004

(65) Prior Publication Data

US 2005/0014793 A1 Jan. 20, 2005

Related U.S. Application Data

(63) Continuation of application No. 10/399,022, filed as application No. PCT/EP01/11610 on Oct. 5, 2001, now abandoned.

(30) Foreign Application Priority Data

Oct. 10, 2000 (GB) .................. 0024808.8

(51) Int. Cl.
*C07D 215/36* (2006.01)
*C07D 401/02* (2006.01)
*A61K 31/47* (2006.01)

(52) U.S. Cl. .............. 514/314; 546/193; 546/291; 546/276.4; 546/300; 514/342; 514/343; 514/346; 514/351

(58) Field of Classification Search ........... 546/300, 546/193, 291, 276.4; 514/351, 314, 342, 514/343, 346
See application file for complete search history.

(56) References Cited

FOREIGN PATENT DOCUMENTS

WO WO 99/24420 5/1999

*Primary Examiner*—Zinna N. Davis
(74) *Attorney, Agent, or Firm*—James M. Kanagy; Mary E. McCarthy; Charles Kinzig

(57) ABSTRACT

Compounds of formula (I):

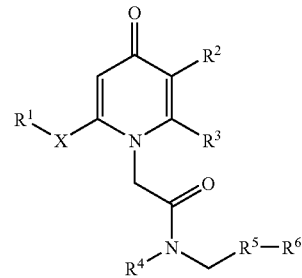

are inhibitors of the enzyme Lp-PLA$_2$ and are of use in therapy, in particular for treating atherosclerosis.

20 Claims, No Drawings

PYRIDINONE DERIVATIVES FOR TREATMENT OF ATHEROSCLEROSIS

This application is a continuation of U.S. Ser. No. 10/399,022 filed on 9 Sep. 2003 now abandoned which is a 371 application of PCT/EP01/11610 filed 5 Oct. 2001.

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describes the phospholipase $A_2$ enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996: 16; 591–9) wherein it is referred to as LDL-$PLA_2$. A later patent application (WO 95/09921, Icos Corporation) and a related publication in Nature (Tjoelker et al, vol 374, 6 Apr. 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, in particular having several pro-atherogenic activities ascribed to it including monocyte chemotaxis and induction of endothelial dysfunction, both of which facilitate monocyte-derived macrophage accumulation within the artery wall. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

A recently published study (WOSCOPS—Packard et al, N. Engl. J. Med. 343 (2000) 1148–1155) has shown that the level of the enzyme Lp-$PLA_2$ is an independent risk factor in coronary artery disease.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid oxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, ischaemia, reperfusion injury and acute and chronic inflammation.

Patent applications WO 96/12963, WO 96/13484, WO 96/19451, WO 97/02242, WO 97/217675, WO 97/217676, WO 96/41098, and WO 97/41099 (SmithKline Beecham plc) disclose inter alia various series of 4-thionyl/sulfinyl/sulfonyl azetidinone compounds which are inhibitors of the enzyme Lp-$PLA_2$. These are irreversible, acylating inhibitors (Tew et al, Biochemistry, 37, 10087, 1998).

A further class of compounds has now been identified which are non-acylating inhibitors of the enzyme Lp-$PLA_2$. Thus, WO 99/24420, WO 00/10980, WO 00/66566, WO 00/66567 and WO 00/68208 (SmithKline Beecham plc) disclose a class of pyrimidone compounds. We have now found that the pyrimidone ring may be replaced by a pyridone ring, to give compounds having good activity as inhibitors of the enzyme Lp-$PLA_2$.

Accordingly, the present invention provides a compound of formula (I):

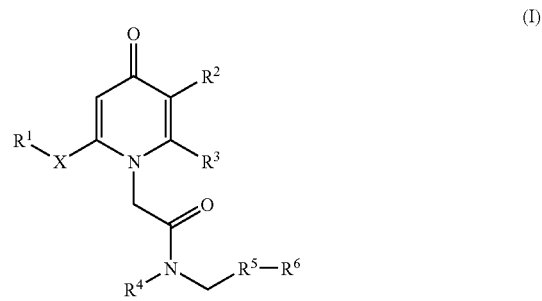

in which:

$R^1$ is an aryl group, optionally substituted by 1, 2, 3 or 4 substituents which may be the same or different selected from $C_{(1-6)}$alkyl, $C_{(1-6)}$alkoxy, $C_{(1-6)}$alkylthio, hydroxy, halogen, CN, mono to perfluoro-$C_{(1-4)}$alkyl, mono to perfluoro-$C_{(1-4)}$alkoxyaryl, and aryl$C_{(1-4)}$alkyl;

$R^2$ is halogen, $C_{(1-3)}$alkyl, $C_{(1-3)}$alkoxy, hydroxy$C_{(1-3)}$alkyl, $C_{(1-3)}$alkylthio, $C_{(1-3)}$alkylsulphinyl, amino$C_{(1-3)}$alkyl, mono- or di-$C_{(1-3)}$alkylamino$C_{(1-3)}$alkyl, $C_{(1-3)}$alkylcarbonylamino$C_{(1-3)}$alkyl, $C_{(1-3)}$alkoxy$C_{(1-3)}$alkylcarbonylamino$C_{(1-3)}$alkyl, $C_{(1-3)}$alkylsulphonylamino$C_{(1-3)}$alkyl, $C_{(1-3)}$alkylcarboxy, $C_{(1-3)}$alkylcarboxy$C_{(1-3)}$alkyl, and $R^3$ is hydrogen, halogen, $C_{(1-3)}$alkyl, or hydroxy$C_{(1-3)}$alkyl; or $R^2$ and $R^3$ together with the pyridone ring carbon atoms to which they are attached form a fused 5- or 6-membered carbocyclic ring; or $R^2$ and $R^3$ together with the pyridone ring carbon atoms to which they are attached form a fused benzo or heteroaryl ring optionally substituted by 1, 2, 3 or 4 substituents which may be the same or different selected from halogen, $C_{(1-4)}$alkyl, cyano, $C_{(1-3)}$alkoxy$C_{(1-3)}$alkyl, $C_{(1-4)}$alkoxy or $C_{(1-4)}$alkylthio, or mono to perfluoro-$C_{(1-4)}$alkyl;

$R^4$ is hydrogen, $C_{(1-6)}$alkyl which may be unsubstituted or substituted by 1, 2 or 3 substituents selected from hydroxy, halogen, $OR^7$, $COR^7$, carboxy, $COOR^7$, $CONR^9R^{10}$, $NR^9R^{10}$, $NR^7COR^8$, mono- or di-(hydroxy$C_{(1-6)}$alkyl)amino and N-hydroxy$C_{(1-6)}$alkyl-N—$C_{(1-6)}$alkylamino; or $R^4$ is Het-$C_{(0-4)}$alkyl in which Het is a 5- to 7-membered heterocyclyl ring comprising N and optionally O or S, and in which N may be substituted by $COR^7$, $COOR^7$, $CONR^9R^{10}$, or $C_{(1-6)}$alkyl optionally substituted by 1, 2 or 3 substituents selected from hydroxy, halogen, $OR^7$, $COR^7$, carboxy, $COOR^7$, $CONR^9R^{10}$ or $NR^9R^{10}$, for instance, piperidin-4-yl, pyrrolidin-3-yl;

$R^5$ is an aryl or a heteroaryl ring optionally substituted by 1, 2, 3 or 4 substituents which may be the same or different selected from $C_{(1-6)}$alkyl, $C_{(1-6)}$alkoxy, $C_{(1-6)}$alkylthio, aryl$C_{(1-6)}$alkoxy, hydroxy, halogen, CN, $COR^7$, carboxy, $COOR^7$, $NR^7COR^8$, $CONR^9R^{10}$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy;

$R^6$ is an aryl or a heteroaryl ring which is further optionally substituted by 1, 2, 3 or 4 substituents which may be the same or different selected from $C_{(1-6)}$alkyl, $C_{(1-6)}$alkoxy, $C_{(1-6)}$alkylthio, $C_{(1-6)}$alkylsulfonyl, aryl$C_{(1-6)}$alkoxy, hydroxy, halogen, CN, $COR^7$, carboxy, $COOR^7$, $CONR^9R^{10}$, $NR^7COR^8$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy, or $C_{(5-10)}$alkyl;

$R^7$ and $R^8$ are independently hydrogen or $C_{(1-12)}$alkyl, for instance $C_{(1-4)}$alkyl (e.g. methyl or ethyl);

$R^9$ and $R^{10}$ which may be the same or different is each selected from hydrogen, or $C_{(1-12)}$alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylcarboxy, aryl, e.g. phenyl, or aralkyl, e.g benzyl, for instance morpholine or piperazine; and X is a $C_{(2-4)}$alkylene group (optionally substituted by 1, 2 or 3 substituents selected from methyl and ethyl), CH=CH, $(CH_2)_nS$ or $(CH_2)_nO$ where n is 1, 2 or 3.

In a further aspect the present invention provides a compound of formula (I) as defined above in which:

$R^2$ and $R^3$ together with the pyridone ring carbon atoms to which they are attached form a fused benzo or heteroaryl ring optionally substituted by 1, 2, 3 or 4 substituents which may be the same or different selected from halogen, $C_{(1-4)}$alkyl, cyano, $C_{(1-4)}$alkoxy or $C_{(1-4)}$alkylthio, or mono to perfluoro-$C_{(1-4)}$alkyl.

Representative examples of $R^1$ when an aryl group include phenyl and naphthyl. Preferably, $R^1$ is phenyl optionally substituted by halogen, $C_{(1-6)}$alkyl, trifluoromethyl, $C_{(1-6)}$alkoxy, preferably, from 1 to 3 fluoro, more preferably, 2,3-difluoro.

Representative examples of $R^2$ include methyl, ethyl, and trifluoroethyl when $R^3$ is hydrogen.

Representative examples of $R^3$ include methyl when $R^2$ is methyl.

Further representative examples of $R^2$ and $R^3$ include when $R^2$ and $R^3$ together with the pyridone ring carbon atoms to which they are attached form a fused 5-membered carbocyclic (cyclopentenyl) ring, or a fused benzo, pyrido, pyrazolo or thieno ring.

Further representative examples of $R^2$ and $R^3$ include when $R^2$ and $R^3$, together with the pyridone ring carbon atoms to which they are attached, form a pyrazolo ring substituted on the N atom by $C_{(1-3)}$alkyl or methoxyethyl; and when $R^2$ and $R^3$, together with the pyridone ring carbon atoms to which they are attached, form either a thiazolyl, thieno or pyrido ring substituted by methyl.

Preferably, $R^2$ and $R^3$ together with the pyridone ring carbon atoms to which they are attached form a fused 5-membered carbocyclic (cyclopentenyl) ring or a fused benzo, pyrido, thieno or pyrazolo ring.

Preferably, $R^2$ and $R^3$, together with the pyridone ring carbon atoms to which they are attached, form a fused thiazolyl ring substituted by methyl.

Representative examples of $R^4$ include hydrogen, methyl, 2-diethylamino)ethyl, 2-(piperidin-1-yl)ethyl, 2-(pyrrolidin-1-yl)ethyl, 3-(morpholin-4-yl)propyl, 1-ethyl-piperidin-4-yl and 1-ethyl-pyrrolidin-2-ylmethyl. Preferably $R^4$ is 2-(diethylamino)ethyl or 1-ethyl-piperidin-4-yl.

Further representative examples of $R^4$ include piperidin-4-yl substituted at the 1-position by methyl, isopropyl, 1-(2-methoxyethyl), 1-(2-hydroxyethyl), t-butoxycarbonyl or ethoxycarbonylmethyl; ethyl substituted at the 2-position by aminoethyl; 1-ethylpiperidinylmethyl; piperidin-4-yl; 3-diethylaminopropyl; 4-pyrrolidin-1-ylbutyl and 1-ethylpyrrolidin-3-yl.

Preferably $R^4$ is 1-(2-methoxyethyl)piperidin-4-yl, 1-methylpiperidin-4-yl or 1-ethylpyrrolidin-3-yl.

Representative examples of $R^5$ include phenyl and pyridyl. Preferably, $R^5$ is phenyl.

Representative examples of $R^6$ include phenyl optionally substituted by halogen, or trifluoromethyl, preferably at the 4-position and hexyl. Preferably, $R^6$ is phenyl substituted by trifluoromethyl at the 4-position.

Further representative examples of $R^6$ include phenyl substituted by 1 or more $C_{(1-3)}$alkyl. Preferably, $R^6$ is phenyl substituted by ethyl in the 4-position.

Preferably, $R^5$ and $R^6$ together form a 4-(phenyl)phenyl or a 2-(phenyl)pyridinyl substituent in which the remote phenyl ring may be optionally substituted by halogen or trifluoromethyl, preferably at the 4-position.

Preferably X is $C_{(2-4)}$alkylene, more preferably $C_{(2-3)}$ alkylene, most preferably, $(CH_2)_2$, or $CH_2S$.

It will be appreciated that within the compounds of formula (I) there is a sub-group of compounds (group A) in which:

$R^1$ is phenyl substituted by 2,3-difluoro;

$R^2$ and $R^3$, together with the pyridone ring carbon atoms to which they are attached, form a fused 5-membered carbocyclic (cyclopentenyl) ring, or a fused benzo or pyrido ring;

$R^4$ is 2-(diethylamino)ethyl, 1-ethyl-piperidin-4-yl, 1-(2-methoxyethyl)piperidin-4-yl, 1-methylpiperidin-4-yl or 1-ethylpyrrolidin-3-yl;

$R^5$ is phenyl;

$R^6$ is phenyl substituted by ethyl or trifluoromethyl in the 4-position; and

X is $CH_2S$.

It will be appreciated that within the compounds of formula (I) there is a further sub-group of compounds (group B) in which:

$R^1$ is phenyl substituted by 2,3-difluoro;

$R^2$ and $R^3$, together with the pyridone ring carbon atoms to which they are attached, form a fused thiazolyl ring substituted by methyl, or a benzo or pyrido ring;

$R^4$ is 2-(diethylamino)ethyl, 1-ethyl-piperidin-4-yl, 1-(2-methoxyethyl)piperidin-4-yl, 1-methylpiperidin-4-yl or 1-ethylpyrrolidin-3-yl;

$R^5$ is phenyl;

$R^6$ is phenyl substituted by trifluoromethyl in the 4-position; and

X is $(CH_2)_2$.

It will be appreciated that within the compounds of formula (I) there is a further sub-group of compounds (group C) in which:

$R^1$ is phenyl substituted by 2,3-difluoro;

$R^2$ and $R^3$, together with the pyridone ring carbon atoms to which they are attached, form a fused benzo or pyrido ring;

$R^4$ is 1-(2-methoxyethyl)piperidin-4-yl;

$R^5$ and $R^6$ together form a 4-(phenyl)phenyl substituent in which the remote phenyl ring is substituted by trifluoromethyl, preferably at the 4-position; and X is $CH_2S$ or $(CH_2)_2$.

It will be appreciated that compounds of the present invention may comprise one or more chiral centres so that stereoisomers may be formed. The present invention covers all such stereoisomers, including individual diastereoisomers and enantiomers, and mixtures thereof.

It will be appreciated that in some instances, compounds of the present invention may include a basic function such as an amino group as a substituent. Such basic functions may be used to form acid addition salts, in particular pharmaceutically acceptable salts. Pharmaceutically acceptable salts include those described by Berge, Bighley, and Monkhouse, *J. Pharm. Sci,* 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, taurocholic acid, benzenesulfonic, p-toluenesulfonic, hydrochloric, hydrobromic, sulfuric, cyclohexylsulfamic, phosphoric and nitric acids.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm. Sci.,* 1977, 66, 1–19. Preferred salts include alkali metal salts such as the sodium and potassium salts.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the term "aryl" refers to, unless otherwise defined, a mono- or bicyclic aromatic ring system containing up to 10 carbon atoms in the ring system, for instance phenyl or naphthyl.

When used herein, the term "heteroaryl" refers to a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When used herein, the terms "halogen" and "halo" include fluorine, chlorine, bromine and iodine and fluoro, chloro, bromo and iodo, respectively.

Most preferred compounds of formula (I) are:

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide;

or a pharmaceutically acceptable salt thereof, in particular the bitartrate, hydrochloride, dihydrochloride or paratoluenesulfonate salt.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are re-crystallised from organic solvents, solvent of crystallisation may be present in the crystalline product This invention includes Within its scope such solvates. Similarly, some of the compounds of this invention may be crystallised or re-crystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-$PLA_2$) and as such are expected to be of use in therapy, in particular in the treatment of atherosclerosis. In a further aspect therefore the present invention provides a compound of formula (I) for use in therapy.

The compounds of formula (I) are inhibitors of lysophosphatidylcholine production by Lp-$PLA_2$ and may therefore also have a general application in any disorder that involves endothelial dysfunction, for example atherosclerosis, diabetes, hypertension, angina pectoris and after ischaemia and reperfusion. In addition, compounds of formula (I) may have a general application in any disorder that involves lipid oxidation in conjunction with enzyme activity, for example in addition to conditions such as atherosclerosis and diabetes, other conditions such as rheumatoid arthritis, stroke, inflammatory conditions of the brain such as Alzheimer's Disease, myocardial infarction, ischaemia, reperfusion injury, sepsis, and acute and chronic inflammation.

Further applications include any disorder that involves activated monocytes, macrophages or lymphocytes, as all of these cell types express Lp-$PLA_2$. Examples of such disorders include psoriasis.

Accordingly, in a further aspect, the present invention provides for a method of treating a disease state associated with activity of the enzyme Lp-$PLA_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid oxidation in conjunction with Lp-$PLA_2$ activity; or with endothelial dysfunction.

Compounds of the present invention may also be of use in treating the above mentioned disease states in combination with an anti-hyperlipidaemic, anti-atherosclerotic, anti-diabetic, anti-anginal, anti-inflammatory, or anti-hypertension agent or an agent for lowering Lp(a). Examples of the above include cholesterol synthesis inhibitors such as statins, antioxidants such as probucol, insulin sensitisers, calcium channel antagonists, and anti-inflammatory drugs such as NSAIDs. Examples of agents for lowering Lp(a) include the aminophosphonates described in WO 97/02037, WO 98/28310, WO 98/28311 and WO 98/28312 (Symphar SA and SmithKline Beecham).

A preferred combination therapy will be the use of a compound of the present invention and a statin. The statins are a well known class of cholesterol lowering agents and include atorvastatin, simvarstatin, pravastatin, cerivastatin, fluvastatin, lovastatin and rosuvastatin (also referred to as S-4522 or ZD 4522, Astra Zeneca). The two agents may be administered at substantially the same time or at different times, according to the discretion of the physician.

A further preferred combination therapy will be the use of a compound of the present invention and an anti-diabetic agent or an insulin sensitiser, as coronary heart disease is a major cause of death for diabetics. Within this class, preferred compounds for use with a compound of the present invention include the PPARgamma activators, for instance G1262570 (GlaxoSmithKline) and the glitazone class of compounds such as rosiglitazone (Avandia, GlaxoSmithKline), troglitazone and pioglitazone.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intramuscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

A compound of formula (I) may be prepared by reacting an acid compound of formula (II):

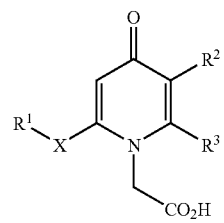

(II)

in which X, $R^1$, $R^2$ and $R^3$ are as hereinbefore defined, with an amine compound of formula (III):

$$R^6\text{---}R^5\text{---}CH_2NHR^4 \qquad (III)$$

in which $R^4$, $R^5$ and $R^6$ are as hereinbefore defined; under amide forming conditions.

Suitable amide forming conditions are well known in the art and include treating the acid of formula (II) with the amine of formula (III) in the presence of a coupling agent such as 1-(3-dimethyl-aminopropyl)-3-ethylcarbodiimide (DEC) and 1-hydroxybenzotriazole (HOBt), or O-(7-azabenzotriazol-1-yl)-N,N,N',N'-tetramethyluronium hexafluorophosphate (HATU) and di-isopropylethylamine, in an aprotic solvent such as dichloromethane or dimethylformamide.

A compound of formula (II) may be readily prepared from a corresponding ester of formula (IV):

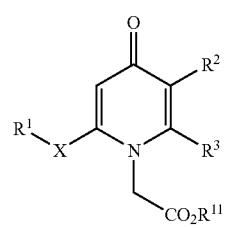

(IV)

in which X, $R^1$, $R^2$ and $R^3$ are as hereinbefore defined, and $R^{11}$ is $C_{(1-6)}$alkyl, for example ethyl or t-butyl, by treating with a de-esterifying agent, for instance, when $R^{11}$ is t-butyl, trifluoroacetic acid or when $R^{11}$ is ethyl, sodium hydroxide in dioxan.

The overall synthesis of compounds of formula (I) is illustrated in the following scheme wherein $R^1$ to $R^{11}$ are as hereinbefore defined:

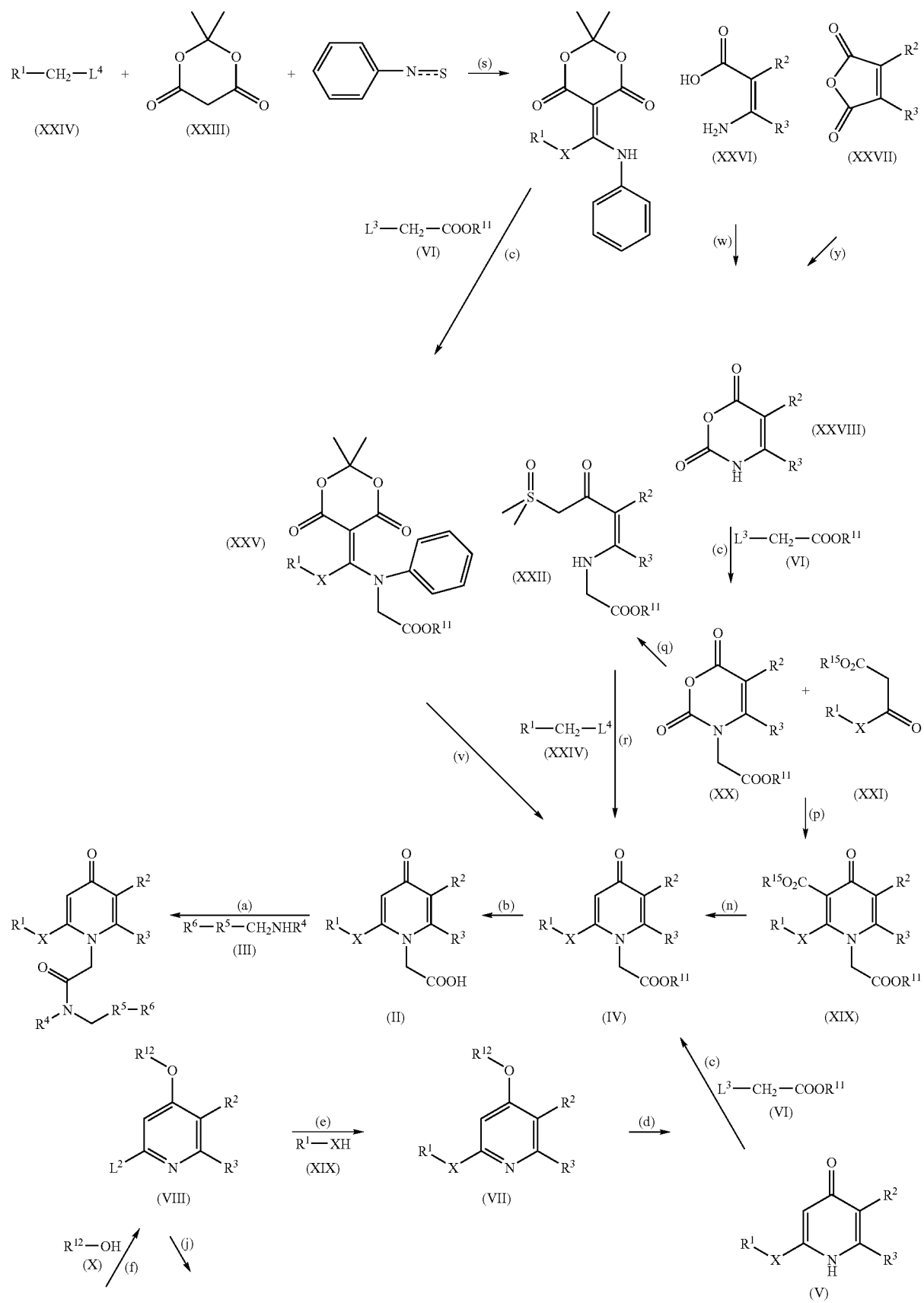

-continued

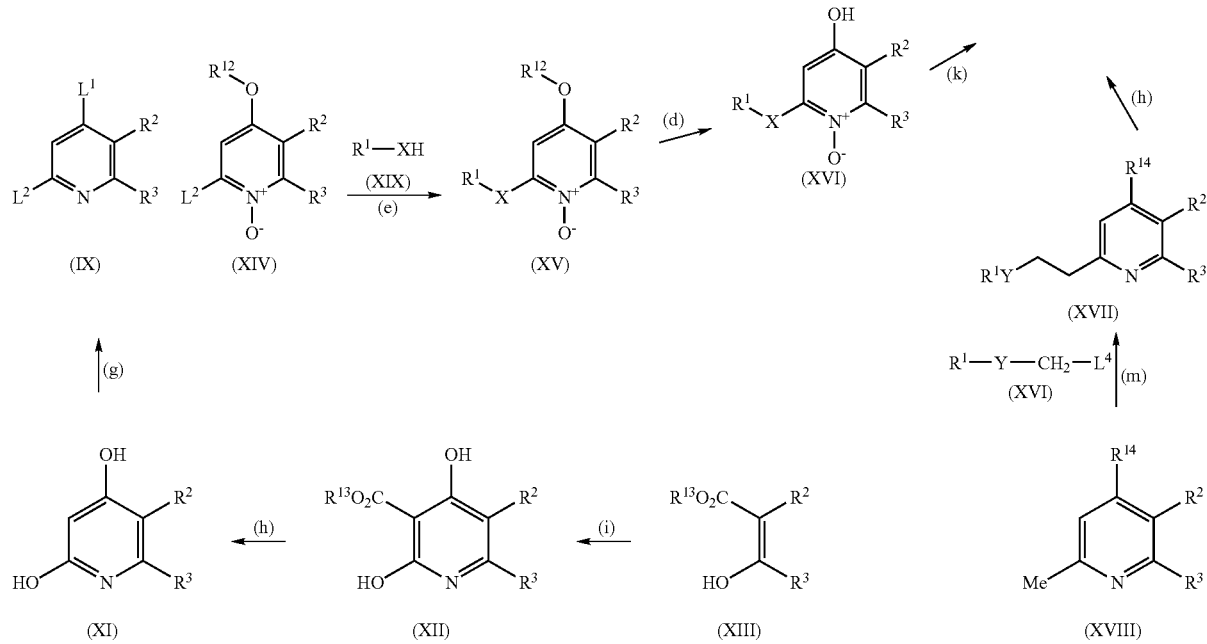

Referring to the scheme, the ester (IV) is usually prepared by N-1 alkylation of (V) using (VI), in which $R^{11}$ is as hereinbefore defined e.g. (VI) is t-butyl bromoacetate or ethyl bromoacetate, in the presence of a base e.g. BuLi in THF or sodium hydride in N-methyl pyrrolidinone (NMP) (step c).

When X is $CH_2S$, the key intermediate (IV) may be synthesised by reacting (XX) with dimethyloxosulfonium methylide, generated via the treatment of trimethylsulfoxonium iodide with sodium hydride at-low temperature, to yield a sulfur ylid (XXII) (step q). Subsequent treatment of (XXII) with carbon disulfide in the presence of diisopropylamine, followed by $R^1 CH_2\text{-}L^4$, where $L^4$ is a leaving group, yields intermediate (IV) (step r).

Alternatively, when X is $CH_2S$, the $R^1X$ substituent may be introduced by displacement of a leaving group $L^2$ (e.g. Cl) (step e) either on a pyridine (VIII) or pyridine N-oxide (XIV), to give 2-substituted pyridines (VII) and (XV). Transformation of (VII) or (XV) to the 4-pyridone (V) is accomplished by deprotection of the 4-oxygen (e.g. using $(Ph_3P)_3RhCl$ when in aq. ethanol when $R^{12}$=allyl) (step d), followed, for (XVI), by removal of the N-oxide substituent, using hydrogen in the presence of Pd/C in acetic acid (step k). The pyridine (VIII) or pyridine N-oxide (XIV) may be prepared by steps (j), (h), (g), (f), and G), in which:

(j) treatment of (VIII) with m-chloroperbenzoic acid in dichloromethane;

(f) treatment of (IX) with $R^{12}OH$ (X), in which $R^{12}$ is allyl, and sodium hydride in DMF;

(g) treatment of (XI) with phosphorus oxychloride;

(h) treatment of (XII) with aq HCl with heating;

(i) treatment of (XIII) with di-lower alkyl malonate and sodium alkoxide in alcohol (in which $R^{13}$ is $C_{(1-6)}$alkyl, typically $R^{13}$=Et); and $R^1 CH_2SH$ (XIX) is typically prepared from the thioacetate, which is formed from the corresponding alkyl bromide $R^1$—$CH_2Br$.

Alternatively, when X is $CH_2S$ and $R^2$ and $R^3$, together with the pyridone ring carbon atoms to which they are attached, form a fused benzo ring, intermediate (IV) may be synthesised from known starting materials by steps (s), (c) and (v) in which:

(s) treatment of Meldrum's acid (XXIII) with sodium hydride at low temperature, followed by reaction with phenylisothiocyanate and subsequent treatment with $R^1CH_2\text{-}L^4$;

(c) as hereinbefore discussed;

(v) treatment of (XXV) with trifluoroacetic acid.

When X is alkylene, it is preferable to use steps (m) and (h) (intermediates (XVII), (XVIII)) or steps (n) and (p) (intermediates (XIX), (XX), (XXI)) in which:

(h) transformation of a 4-substituted pyridine into a 4-pyridone e.g. by treatment of (XVII) $R^{14}$=Cl with aq HCl and dioxan, or deprotection of $R^{14}$=$OR^{12}$, e.g. using conditions of step (d).

(m) chain extension of a 2-alkyl pyridine, e.g. where X=$YCH_2CH_2$ by treatment of a 2-methylpyridine (XVIII) with $R^1$—Y—$CH_2$-$L^4$ (XVI) in which $L^4$ is a leaving group and a strong base, such as BuLi, in THF.

In the alternative route, the 3-ester group is removed from intermediate (XIX) $R^{15}$=$C_{(1-6)}$alkyl by heating in diphenyl ether where $R^{15}$=tBu (step n); Intermediate (XIX) is formed from the 2,6-dioxo-1,3-oxazine (XX) and ester (XXI) by treatment with a base such as NaH in DMF or 1,8-diazabicyclo[5.4.0]undec-7-ene in dichloromethane.

Synthesis of (XX) from known starting materials may be achieved via steps (w) and (c) or steps (y) and (c) in which:

(w) treatment of(VII) with azidotrimethylsilane in THF;

(y) treatment of (XXVI) with phosgene;

(c) as hereinbefore described.

It will be appreciated by those skilled in the art that all other starting materials and intermediates are either known compounds or may be prepared by literature methods, such as those described in "Comprehensive Organic Transformations: a guide to functional group preparations" by Richard Larock (VCH, 1989), incorporated herein by reference.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See for example, those described in 'Protective Groups in Organic Synthesis' by Theodora W Green and Peter G M Wuts, second edition, (John Wiley and Sons, 1991), incorporated herein by reference, which also describes methods for the removal of such groups.

The present invention will now be illustrated by the following examples.

EXAMPLES

The structure and purity of the intermediates and examples was confirmed by 1H-NMR and (in nearly all cases) mass spectroscopy, even where not explicitly indicated below Intermediate A1
4-(4-Trifluoromethylphenyl)benzaldehyde

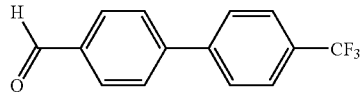

A 3 L 3-neck flask fitted with top stirrer, condenser and argon inlet/outlet was charged with 4-trifluoromethybenzene boronic acid (90.0 g, 0.474 mol), 4-bromobenzaldehyde (83.29 g, 0.450 mol) and 1,2-dimethoxyethane (1.3 L), followed by 2M aqueous sodium carbonate (474 ml) and palladium acetate (5.32 g, 0.0237 mol). The stirring mixture was heated to reflux for 4 h under argon, then allowed to cool to room temperature over 16 h. The reaction mixture was filtered through hyflo. The filtrate was diluted with saturated brine and extracted 3× with ethyl acetate. The combined extracts were dried over magnesium sulfate and filtered through hyflo, giving a clear orange filtrate which was evaporated to a solid (ca. 120 g, crude). Flash chromatography (silica, 10–50% dichloromethane in pet. ether, 10% steps) gave a white solid which dissolved in hexane (500 ml) on boiling. Crystallisation, finally in ice, gave the title compound as a solid which was filtered off, washed with ice cold hexane and dried, (86.33 g, 77%). $^1$H-NMR (CDCl$_3$) δ 7.77–8.03 (8H, m), 10.09 (1H, s).

Intermediate A2 N,N-diethyl-N'-(4'-trifluoromethyl-biphenyl-4-ylmethyl)ethane-1,2-diamine

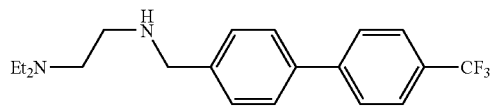

4-(4-Trifluoromethylphenyl)benzaldehyde (85.43 g, 0.3414 mol) (Int. A1) and 4 A molecular sieve (400 g, predried at 120° C.) were suspended in dichloromethane (1.4 L), then N,N-diethyl-ethylenediamine (47.97ml, 0.3414 mol) was added. The mixture was left at room temperature for 16 h with occasional shaking, then the sieves were filtered off and washed with dichloromethane. The combined filtrates were evaporated to a yellow solid and dried under high vacuum. This material (114.3 g, 0.328 mol) in ethanol (1 L) was cooled in an ice bath, and sodium borohydride (12.41 g, 0.328 mol) was added under argon with stirring. Hydrogen evolution was observed. After 30 min the ice bath was removed, and the cloudy yellow solution was left to stand at room temperature for 16 h. The solvent was removed in vacuo, water and brine were added, and the mixture was extracted 3× with dichloromethane. The combined extracts were dried over potassium carbonate and evaporated to give the title compound as a yellow solid, (112.1 g, 98%). $^1$H-NMR (CDCl$_3$) δ 7.66 (4H, s), 7.53–7.56 (2H, m), 7.40–7.44 (2H, m), 3.86 (2H, s), 2.47–2.75 (9H, m), 0.96–1.10 (6H, m); MS(APCI+) found (M+1)=351, C$_{20}$H$_{25}$F$_3$N$_2$ requires 350.

Intermediate A3—4-(4-Trifluoromethylphenyl)benzonitrile

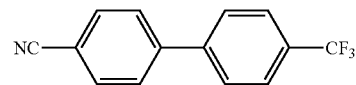

Prepared by the method of intermediate A1 using 4-trifluoromethylbenzeneboronic acid and 4-bromobenzonitrile. $^1$H-NMR (d6 DMSO) δ 7.99–7.94 (6H, m), 7.86 (2H, d); MS(APCI+) found (M+1)=248, C$_{14}$H$_8$NF$_3$ requires 247.

Intermediate A4—4-(4-Trifluoromethylphenyl)benzylamine, free base and hydrochloride salt

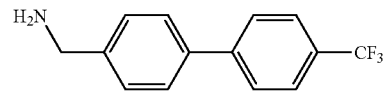

(a) A solution of intermediate A3 (75.5 g, 0.306 mol) in anhydrous THF (500 ml) was added dropwise to a solution of lithium aluminum hydride (460 ml, 1.0M solution in THF) at 0° C. under argon. The mixture was stirred at room temperature for 16 h, then water (17 ml), 10% aqueous sodium hydroxide solution (10 ml) and water (50 ml) were carefully added dropwise over 8 h under argon. The mixture was stirred for 16 h, then filtered through celite and the filtrate evaporated. The residue was dissolved in dichloromethane (500 ml) and washed with brine, dried and evaporated to give the title compound as a cream solid (66.3 g, 86%). $^1$H-NMR (CDCl$_3$) δ 7.68 (4H, s), 7.57 (2H, d), 7.42 (2H, d), 3.94 (2H, s), 1.50 (2H, s); MS(APCI+) found (M−NH$_2$)=235, C$_{14}$H$_{12}$F$_3$N requires 251.

(b) To a solution of intermediate A3 (96.7 g, 0.39 mol) in absolute ethanol (5 L) and concentrated hydrochloric acid (200 ml) was added 10% palladium on charcoal (30.0 g, 54% H$_2$O paste). The mixture was stirred under 50 psi hydrogen for 16 h. Additional 10% palladium on charcoal (25.0 g, 54% H$_2$O paste) was added and the mixture was stirred under 50 psi hydrogen for &further 16 h. The mixture was filtered through celite and the solvent evaporated to give the hydrochloride salt of the title compound as a cream solid (102.5 g, 91%). $^1$H-NMR (d6 DMSO) δ 8.61 (3H, s), 7.93 (2H, d), 7.83 (2H, d), 7.80 (2H, d), 7.65 (2H, d), 4.08 (2H, s); MS(APCI+) found (M−NH$_2$)=235, C$_{14}$H$_{12}$F$_3$N requires 251.

Intermediate A5—N-(1-Methyl-piperidin-4-yl)-4-(4-trifluoromethylphenyl)benzylamine

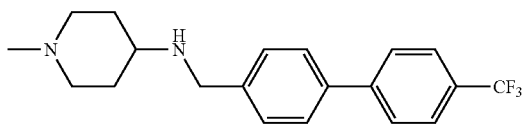

A mixture of intermediate A4 hydrochloride salt (6.0 g, 20.87 mnmol), 1-methyl-piperidin-4-one (2.56 ml, 20.84 mmol), sodium triacetoxyborohydride (6.20 g, 29.25 mmol) and acetic acid (1.3 ml) in dichloroethane (50 ml) was stirred at room temperature under argon for 16 h then poured into 2M sodium hydroxide solution (150 ml). The organic phase was separated and the aqueous layer extracted with dichloromethane. The combined organic phases were washed with brine, dried and evaporated. Chromatography (silica, dichloromethane to 97:3 dichloromethane/methanolic ammonia) gave the product as a cream solid (6.3 g, 87%). $^1$H-NMR (CDCl$_3$) δ 7.68 (4H, s), 7.57 (2H, d), 7.42 (2H, d), 3.87 (2H, s), 2.82 (2H, m), 2.52 (1H, m), 2.27 (3H, s), 1.90–2.02 (4H, m), 1.45–1.51 (2H, m); MS(APCI+) found (M+1)=349, C$_{20}$H$_{23}$N$_2$F$_3$ requires 348.

The following intermediate was made as described in WO 00/66567

| No. | Structure | Name |
|---|---|---|
| A6 | H$_2$N–⟨structure⟩–Cl | 4-(4-Chlorophenyl)-benzylamine |

The following intermediates were made by the method of Intermediate A1:

| No. | Precursors | Name |
|---|---|---|
| A7 | 4-bromobenzaldehyde, 4-methylbenzeneboronic acid | 4-(4-methylphenyl)benzaldehyde |
| A8 | 4-bromobenzaldehyde, 4-ethylbenzeneboronic acid | 4-(4-ethylphenyl)benzaldehyde |
| A9 | 4-isopropyliodobenzene 4-formylbenzeneboronic acid | 4-(4-isopropylphenyl)benzaldehyde |
| A10 | 4-bromo-o-xylene 4-formylbenzeneboronic acid | 4-(3,4-dimethylphenyl) benzaldehyde |
| A11 | 3,4-difluoroiodobenzene 4-formylbenzeneboronic acid | 4-(3,4-difluorophenyl) benzaldehyde |

The following intermediates were made by the method of Intermediate A2: Amine precursors were either commercially available, or readily prepared from commercially available materials by literature methods or minor modifications thereof.

| No. | Precursor | Structure | Name |
|---|---|---|---|
| A20 | Int. A1 | 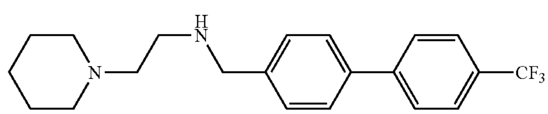 | N-(2-piperidin-1-yl)ethyl)-4-(4-trifluoromethylphenyl)benzylamine |
| A22 | Int. A1 | 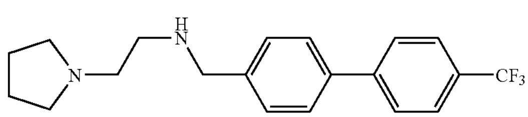 | N-(2-(pyrrolidin-1-yl)ethyl)-4-(4-trifluoromethylphenyl)benzylamine |
| A23 | Int. A1 | 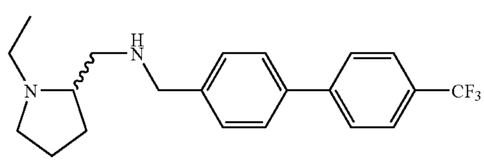 | (±)-N-(1-ethylpyrrolidin-2-ylmethyl)-4-(4-trifluoromethyl-phenyl)benzylamine |
| A24 | Int. A1 | 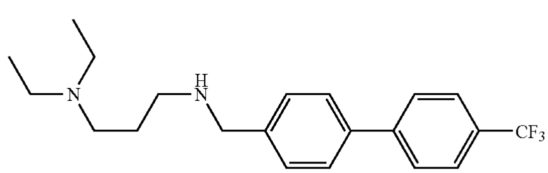 | N-(3-diethylaminopropyl)-4-(4-trifluoromethylphenyl)benzylamine |

-continued

| No. | Precursor | Structure | Name |
|---|---|---|---|
| A25 | Int. A1 | 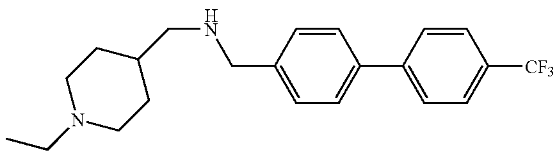 | N-(1-ethylpiperidin-4-ylmethyl)-4-(4-trifluoromethylphenyl)benzylamine |
| A26 | Int. A7 | 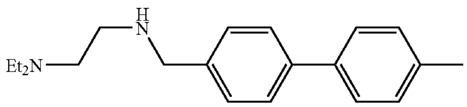 | N-(2-diethylaminoethyl)-4-(4-methylphenyl)benzylamine |
| A27 | Int. A8 | 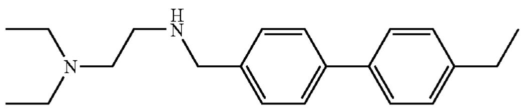 | N-(2-diethylaminoethyl)-4-(4-ethylphenyl)benzylaniine |
| A28 | Int. A9 | 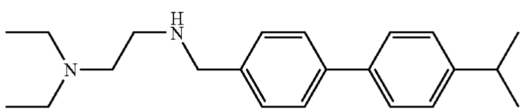 | N-(2-diethylaminoethyl)-4-(4-isopropylphenyl)benzylamine |
| A29 | Int. A8 | 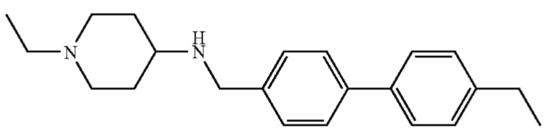 | N-(1-ethylpiperidin-4-yl)-4-(4-ethylphenyl)benzylamine |
| A30 | Int. A10 | 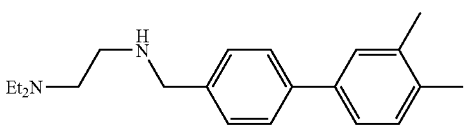 | N-(2-diethylaminoethyl)-4-(3,4-dimethylphenyl)benzylamine |
| A31 | Int. A11 | 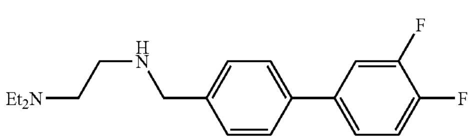 | N-(2-diethylaminoethyl)-4-(3,4-difluorophenyl)benzylamine |
| A32 | Int. A1 | 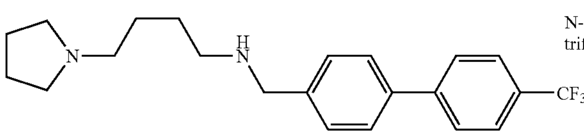 | N-(4-(pyrrolidin-1-yl)butyl)-4-(4-trifluoromethylphenyl)benzylamine |
| A33 | Int. A1 | 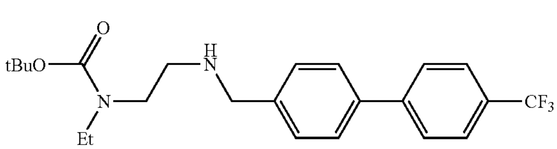 | N-(2-(N'-t-butoxycarbonyl-N'-ethylamino)ethyl)-4-(4-trifluoromethylphenyl)benzylamine |

The following intermediates were made by the method of Intermediate A5: Piperidone precursors were either commercially available, or readily prepared from commercially available materials by literature methods or minor modifications thereof.

| No. | Precursor | Structure | Name |
|---|---|---|---|
| A40 | Int. A4 | 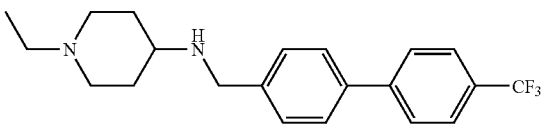 | N-(1-ethylpiperidin-4-yl)-4-(4-trifluoromethyl-phenyl)benzylamine |
| A41 | Int. A4 | 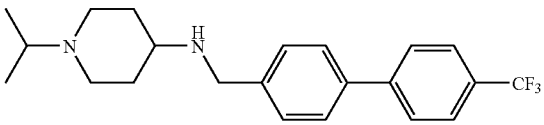 | N-(1-isopropylpiperidin-4-yl)-4-(4-trifluoromethyl-phenyl)benzylamine |
| A42 | Int. A4 | 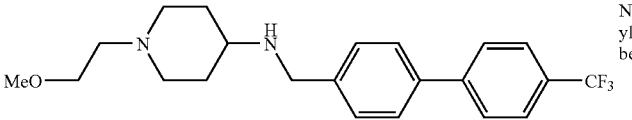 | N-(1-(2-methoxyethyl)piperidin-4-yl)-4-(4-trifluoromethylphenyl)-benzylamine |
| A43 | Int. A4 | 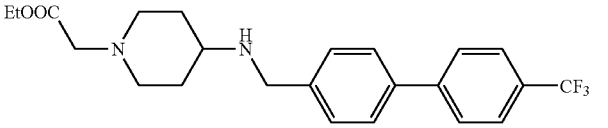 | N-(1-ethoxycarbonylmethylpiperidin-4-yl)-4-(4-trifluoromethylphenyl)-benzylamine |
| A44 | Int. A6 | 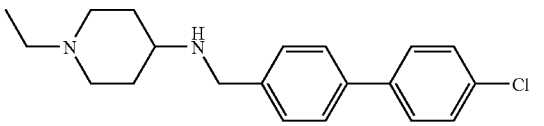 | N-(1-ethylpiperidin-4-yl)-4-(chlorophenyl)benzylamine |
| A45 | Int. A6 | 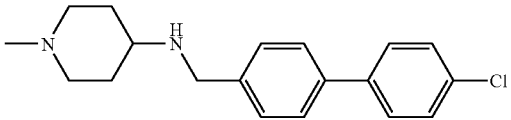 | N-(1-methylpiperidin-4-yl)-4-(4-chlorophenyl)benzylamine |
| A46 | Int. A6 | 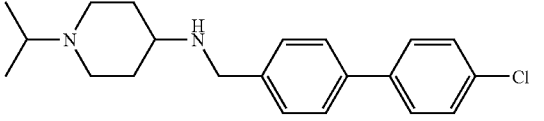 | N-(1-isopropylpiperidin-4-yl)-4-(4-chlorophenyl)benzylamine |
| A47 | Int. A6 | 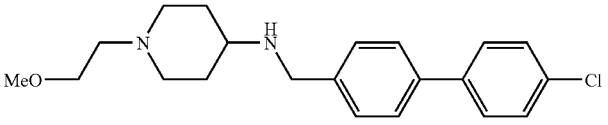 | N-(1-(2-methoxyethyl)piperidin-4-yl)-4-(4-chlorophenyl)-benzylamine |
| A48 | Int. A4 | 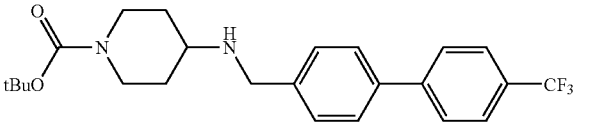 | N-(1-(t-butoxycarbonyl)piperidin-4-yl)-4-(4-trifluoromethyl-phenyl)benzylamine |

Intermediate B1—Thioacetic acid S-(2,3-difluorobenzyl)ester

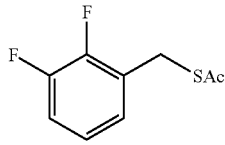

Potassium thioacetate (13.45 g, 1.2 equiv) was added portionwise to a solution of 2,3-difluorobenzyl bromide (20 g, 1 equiv) in dimethylformamide (200 ml) and the reaction stirred for 4 h at room temperature. The resultant solid was filtered off and the filtrate partitioned between diethyl ether and water, the organic phase was dried and evaporated. Chromatography (silica, 20:1 petrol/ethyl acetate) gave the title compound as a yellow oil (18.35 g). $^1$H-NMR (CDCl$_3$) δ 2.35 (3H, s), 4.15 (2H, d), 6.98–7.13 (3H, m).

Intermediate B2—2,3-Difluorobenzyl mercaptan

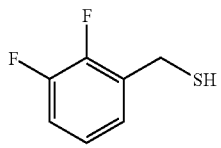

A mixture of thioacetic acid S-(2,3-difluorobenzyl)ester (Intermediate B1) (18.35 g, 1 equiv) and potassium carbonate (25.11 g, 2 equiv) in methanol (200 ml) and water (400 ml) was stirred overnight before being poured into dichloromethane (500 ml). The organic phase was dried and evaporated and distilled (125° C.@5.6 mBar) to give the title compound as a colourless oil (12.15 g). $^1$H-NMR (CDCl$_3$) δ 1.89 (1H, t), 3.78 (2H, d), 7.05 (3H, m).

Intermediate B3—Ethyl 2,4-dihydroxy-6,7-dihydro-5H-[1]pyrindine-3-carboxylate

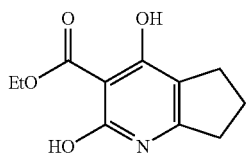

A mixture of ethyl 2-amino-1-cyclopentene-1-carboxylate (10.1 g, 1 equiv), diethyl malonate (9.9 ml, 1 equiv), sodium ethoxide (26.7 ml, 1.1 equiv, 21 wt % solution in ethanol) in ethanol was heated in a sealed vessel to 110° C. for 96 h. After cooling the solvent was removed and the residue suspended in water. The suspension was acidified with aqueous hydrochloric acid (pH~3) and the precipitate was collected and dried to give the title compound as a light brown solid (11.52 g). $^1$H-NMR (d6-DMSO) δ 1.27 (3H, t), 2.00 (2H, qn), 2.60 (2H, t), 2.73 (2H, t), 4.30 (2H, q), 11.62 (1H, br s), 13.18 (1H, br s).

Intermediate B4—2,4-Dihydroxy-6,7-dihydro-5H-[1]pyrindine

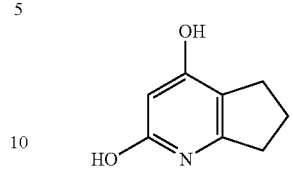

A mixture of ethyl 2,4-dihydroxy-6,7-dihydro-5H-[1]pyrindine-3-carboxylate (Int. B3) (11.52 g) and aqueous hydrochloric acid (2M, 100 ml) was heated together overnight. After cooling the solvent was removed by freeze drying and the title compound obtained as a brown solid (8.02 g). $^1$H-NMR (d$_6$-DMSO) 2.09 (2H, qn), 2.72 (2H, t), 2.93 (2H, t), 6.56 (1H, s); MS (APCI+) found (M+1)=152; C$_8$H$_9$NO$_2$ requires 151.

Intermediate B5—2,4-Dichloro-6,7-dihydro-5H-[1]pyrindine

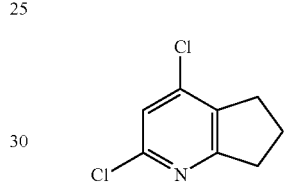

A mixture of 2,4dihydroxy-6,7-dihydro-5H-[1]pyrindine (Int. B4) (8.02 g) and phosphorous oxychloride (40 ml) was heated to reflux overnight. The excess phosphorous oxychloride was evaporated off and the residue poured over ice. The resulting brown solid was filtered off and dried (7.36 g). $^1$H-NMR (CDCl$_3$) δ 2.17 (2H, m), 2.96 (2H, t), 3.07 (2H, t), 7.12 (1H, s); MS (APCI+) found (M+1)=188; C$_8$H$_7$$^{35}$Cl$_2$N requires 187.

Intermediate B6—4-Allyloxy-2-chloro-6,7-dihydro-5H-[1]pyrindine

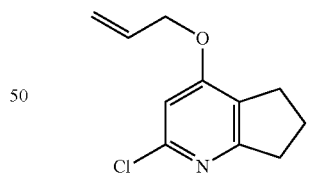

Allyl alcohol (4.1 ml, 1.2 equiv) was added dropwise to a suspension of sodium hydride (2.2 g, 1.1 equiv, 60% dispersion in mineral oil) in dimethylformamnide (80 ml) under argon at 0° C. The reaction mixture was stirred for 20 min prior to adding dropwise to a solution of 2,4-dichloro-6,7-dihydro-5H-[1]pyrindine (Int. B5) (9.42 g, 1 equiv) in dimethylformamide (70 ml) at 0° C., stirring was continued at ambient temperature overnight. The solvent was evaporated and the residue partitioned between water and ethyl acetate, the organic phase was dried and evaporated. Chromatography (silica, 10:1 toluene/ethyl acetate) gave the title compound as an off white solid (8.99 g). $^1$H-NMR (CDCl$_3$) δ 2.11 (2H, m), 2.84 (2H, t), 2.97 (2H, t), 4.58 (2H, m), 5.30–5.46 (2H, m), 5.94–6.07 (1H, m), 6.59 (1H, s); MS (APCI+) found (M+1)=210; $C_{11}H_{12}{}^{35}ClNO$ requires 209.

Intermediate B7—4-Allyloxy-2-chloro-6,7-dihydro-5H-[1]pyrindine-1-oxide

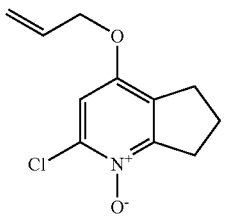

A mixture of 3-chloroperbenzoic acid (19.5 g, 1.5 equiv) and 4-allyloxy-2-chloro-6,7-dihydro-5H-[1]pyrindine (Int. B6) (8.99 g, 1 equiv) in dichloromethane (100 ml) was stirred at ambient temperature under argon for 4 h, washed with aqueous sodium bicarbonate, dried and evaporated. Chromatography (silica, 5% methanol in dichloromethane) gave the title compound as a white solid (6.98 g). $^1$H-NMR (CDCl$_3$) δ 2.19 (2H, qn), 2.97 (2H, t), 3.22 (2H, t), 4.57 (2H, m), 5.30–5.45 (2H, m), 5.93–6.08 (1H, m), 6.80 (1H, s); MS (APCI+) found (M+1)=226; $C_{11}H_{12}{}^{35}ClNO_2$ requires 225.

Intermediate B8—4-Allyloxy-2-(4-fluorobenzylthio) 6,7-dihydro-5H-[1]pyrindine 1-oxide

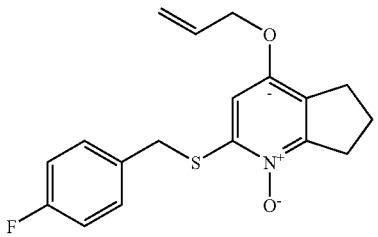

4-Fluorobenzyl mercaptan (1.59 g, 1.2 equiv) was added dropwise to a suspension of sodium hydride (0.372 g, 1.0 equiv, 60% dispersion in mineral oil) in dimethylformamide (30 ml) under argon at 0° C. The reaction was stirred for 20 min, before adding dropwise to a solution of 4-allyloxy-2chloro-6,7-dihydro-5H-[1]pyrindine-1-oxide (Int. B7) (2.1 g, 1 equiv) in dimethylformamide (20 ml) at 0° C., stirring was continued at ambient temperature overnight. The solvent was evaporated and the residue partitioned between water and ethyl acetate, the organic phase was dried and evaporated. Chromatography (silica, 3% methanol in dichloromethane) gave the title compound as an off white solid (2.65 g). $^1$H-NMR (CDCl$_3$) δ 2.16 (2H, qn), 2.91 (2H, m), 3.18 (2H, t), 4.14 (2H, s), 4.43 (2H, m), 5.28 (2H, m), 5.84–5.97 (1H, m), 6.37 (1H, s), 7.00 (2H, m), 7.39 (2H, m); MS (APCI+) found (M+1)=332; $C_{18}H_{18}FNO_2S$ requires 331.

Intermediate B9—2-(4-Fluorobenzylthio)-1-oxy-6,7-dihydro-5H-[1]pyrindin-4-ol

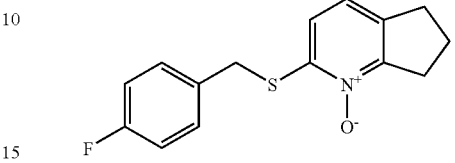

A mixture of 4-allyloxy-2-(4-fluorobenzylthio)-6,7-dihydro-5H-[1]pyrindine 1-oxide (Int. B8) (2.65 g) triphenylphosphine rhodium (I) chloride (0.740 g, 10 mol %) and 1,4-diazobicyclo[2,2,2]octane (0.27 g, 30 mol %) in ethanol (90 ml) and water (10 ml) was heated to reflux overnight. The solvent was removed and the residue chromatographed (silica, 4% methanol in dichloromethane) to yield the title compound as a brown solid (1.75 g). $^1$H-NMR (d$_6$-DMSO) δ 2.07 (2H, m), 2.80 (2H, t), 2.91 (2H, t), 4.14 (2H, s), 6.58 (1H, s), 7.15 (2H, m), 7.47 (2H, m); MS (APCI+) found (M+1)=292; $C_{15}H_{14}FNO_2S$ requires 291.

Intermediate B10—4-Chloro-2-(2-(2,3 difluorophenyl)ethyl)quinoline

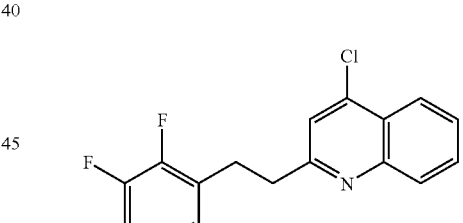

Butyllithium (4.76 ml, 2.5M in hexanes, 1 equiv) was added dropwise to a solution of 4-chloroquinaldine (2.4 ml, 1 equiv) in tetrahydrofuran (30 ml) at −78° C. and the reaction mixture stirred for 15 min. 2,3-Difluorobenzyl bromide (1.82 ml, 1.2 equiv) was added dropwise and stirring was continued for 1 h. After warming to room temperature the solution was diluted with water and ethyl acetate and the organic phase dried and evaporated. Chromatography (silica, 10:1 petrol/ethyl acetate) gave the title compound as a white solid (3.16 g). $^1$H-NMR (CDCl$_3$) δ 3.23 (4H, m), 6.89–6.99 (3H, m), 7.33 (1H, s), 7.59 (1H, m), 7.74 (1H, m), 8.04 (1H, d), 8.15 (1H, d); MS (APCI+) found (M+1)=304; $C_{17}H_{12}{}^{35}ClF_2N$ requires 303.

The following intermediates were prepared by the method of intermediate B10

| No. | Precursor | Structure | Name |
|---|---|---|---|
| B11 | 4-Fluorobenzyl bromide | 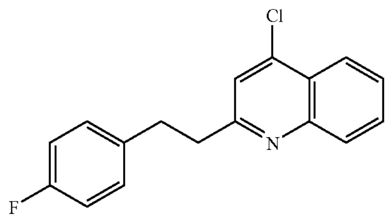 | 4-Chloro-2-(2-(4-fluorophenyl)ethyl)-quinoline |
| B12 | 3,4-Difluorobenzyl bromide | 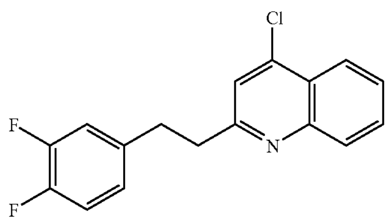 | 4-Chloro-2-(2-(3,4-difluorophenyl)-ethyl)quinoline |
| B13 | 2,4-Difluorobenzyl bromide | 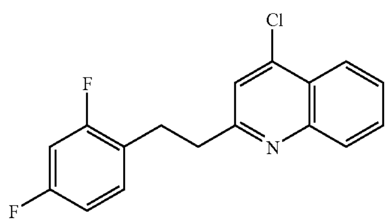 | 4-Chloro-2-(2-(2,4-difluorophenyl)-ethyl)quinoline |
| B14 | 2-Fluorobenzyl bromide | 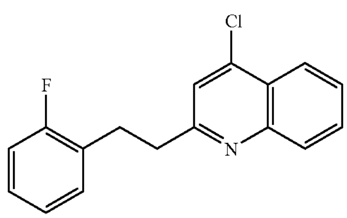 | 4-Chloro-2-(2-(2-fluorophenyl)-ethyl)quinoline |
| B15 | 3-Chlorobenzyl bromide | 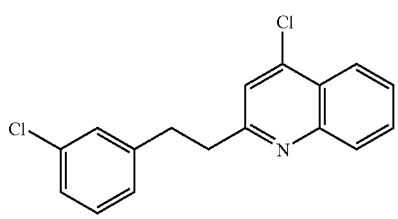 | 4-Chloro-2-(2-(3-chlorophenyl)-ethyl)quinoline |
| B16 | 2,3,4-Trifluoro-benzyl bromide | 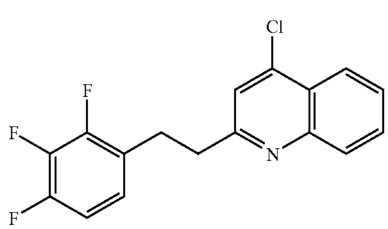 | 4-Chloro-2-(2-(2,3,4-trifluoro-phenyl)ethyl)quinoline |
| B17 | 3-Fluorobenzyl bromide | 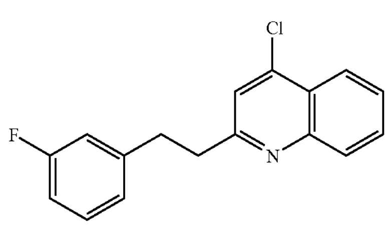 | 4-Chloro-2-(2-(3-fluorophenyl)-ethyl)quinoline |

Intermediate B20—2,4-Dichloroquinoline

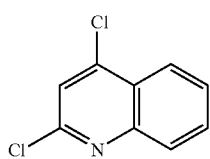

A mixture of 2,4-dihydroxyquinoline (14 g) and phosphorus oxychloride (40 ml) was heated to reflux overnight. The excess phosphorous oxychloride was evaporated off and the residue poured over ice. The resulting solid was filtered off and dried to give the title compound as a brown solid (13.86 g). $^1$H-NMR (CDCl$_3$) δ 7.82 (1H, m), 7.96 (2H, m), 8.03 (1H, d), 8.21 (1H, dd); MS (APCI+) found (M+1)=198; C$_9$H$_5$$^{35}$Cl$_2$N requires 197.

Intermediate B21—4-Allyloxy-2-chloroquinoline

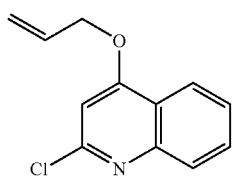

Allyl alcohol (7.1 ml, 1.2 equiv) was added dropwise to a suspension of sodium hydride (3.83 g, 1.1 equiv, 60% dispersion in mineral oil) in dimethylformamide (120 ml) under argon at 0° C. The reaction mixture was stirred for 20 min prior to adding dropwise to a solution of 2,4-dichloroquinoline (Int. B20) (17.26 g, 1 equiv) in dimethylformamide (80 ml) at 0° C., stirring was continued at ambient temperature overnight. The solvent was evaporated and the residue partitioned between water and ethyl acetate, the organic phase was dried and evaporated. Chromatography (silica, toluene) gave the title compound as an off white solid (13.56 g). $^1$H-NMR (CDCl$_3$) δ 4.77 (2H, m), 5.30–5.57 (2H, m), 6.08–6.20 (1H, m), 6.73 (1H, s), 7.52 (1H, m), 7.71 (1H, m), 7.92 (1H, d), 8.17 (1H, dd); MS (APCI+) found (M+1)=220; C$_{12}$H$_{10}$$^{35}$ClNO requires 219.

Intermediate B22—4-Allyloxy-2-(2,3-difluorobenzylthio)quinoline

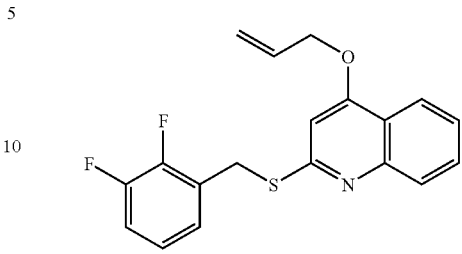

2,3-Difluorobenzyl mercaptan (Int. B2) (2 g, 1.1 equiv) was added dropwise to a suspension of sodium hydride (0.477 g, 1.05 equiv, 60% dispersion in mineral oil) in dimethylformamide (50 ml) under argon at 0° C. The reaction mixture was stirred for 20min, before adding dropwise to a solution of 4-allyloxy-2-chloroquinoline (Int. B21) (2.49 g, 1 equiv) in dimethylformamide (30 ml) at 0° C. and stirring was continued at ambient temperature overnight. The solvent was evaporated and the residue partitioned between water and ethyl acetate, the organic phase was dried and evaporated. Chromatography (silica, 2:1 petrol/toluene) gave the title compound as an off white solid (2.26 g). $^1$H-NMR (CDCl$_3$) δ 4.68 (4H, m), 5.34–5.53 (2H, m), 6.06–6.17 (1H, m), 6.54 (1H, s), 6.96 (2H, m), 7.41 (2H, m), 7.65 (1H, dt), 7.90 (1H, dd), 8.11 (1H, dd); MS (APCI+) found (M+1)=344; C$_{19}$H$_{15}$F$_2$NOS requires 343.

The following intermediate was prepared by the method of intermediate B22:

| No. | Precursors | Structure | Name |
| --- | --- | --- | --- |
| B23 | Int. B21, 4-Fluorobenzyl mercaptan | 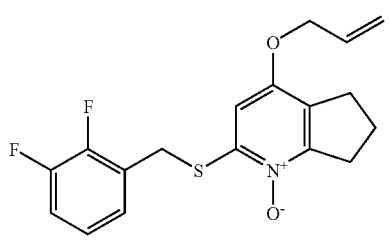 | 4-Allyloxy-2-(4-fluorobenzylthio)quinoline |

Intermediate B24—4-Allyloxy-2-(2,3-difluorobenzylthio)-6,7-dihydro-5H-[1]pyrindine-1-oxide The title compound was prepared from Intermediate B7 and 2,3-difluorobenzylthiol by the method of Intermediate B8.

Intermediate B25—2-(2,3-Difluorobenzylthio)-1-oxy-6,7-dihydro-5H-[1]pyrindin-4-ol

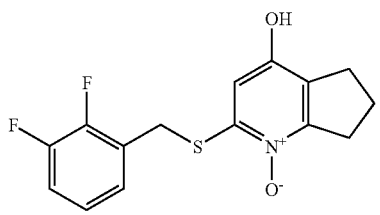

The title compound was prepared from Intermediate B24 by the method of Intermediate B9.

Intermediate B26—3-azaisatoic anhydride

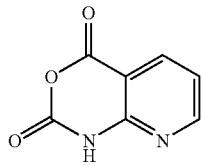

To a stirring solution of 2,3-pyridinedicarboxylic anhydride (100 g, 1 equiv) in anhydrous tetrahydrofuran (1 L) was added dropwise under argon at 38-46° C. over 1.25 h azidotrimethylsilane (97.9 ml, 1.1 equiv). The temperature was maintained at 45-50° C. for a further 2 h then the mixture refluxed for 30 min, cooled to ambient temperature and ethanol (43 ml, 1.1 equiv) added dropwise. On stirring for 16 h an off-white solid was obtained which was filtered, washed and dried, to give the title compound (90.7 g). $^1$H-NMR (d$_6$-DMSO) δ 7.25–7.35 (1H, m), 8.30–8.35 (1H, dd), 8.65–8.7 (1H, dd), 11.3 (1H, br s)

Intermediate B30—6-Methyl-1H-thieno[3,2-d][1,3]oxazine-2,4-dione

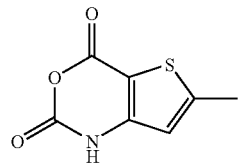

Methyl 3-amino-5-methylthiophene-2-carboxylate (2.0 g, 11.7 mmol) and sodium hydroxide (0.89 g, 22.2 mmol) in 1:1 dioxan/water (40 ml) was heated at reflux for 18 h, then the solvent was removed in vacuo. The crude solid was dissolved in water (30 ml) and phosgene (15 ml, 20% solution in toluene, 30 mmol) was added over 10 min with stirring. After a further 30 min the precipitate was filtered off, washed with water and dried to yield the title compound (0.44 g). $^1$H-NMR (CDCl$_3$) δ 2.5 (3H, s), 6.7 (1H, s), 12.5 (1H, s); MS (APCI+) found (M+H—CO$_2$)=140.

The following intermediates were prepared by the method of Intermediate B30:

| No. | Structure | Name |
|---|---|---|
| B31 | 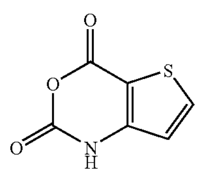 | 1H-thieno[3,2-d][1,3]oxazine-2,4-dione |
| B32 | 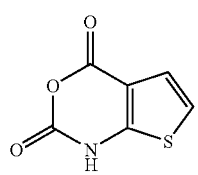 | 1H-thieno[2,3-d][1,3]oxazine-2,4-dione |
| B33 | 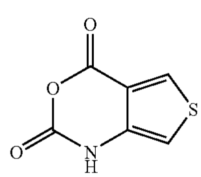 | 1H-thieno[3,4-d][1,3]oxazine-2,4-dione |
| B34 | 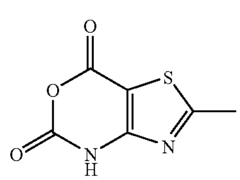 | 2-methylthiazolo[4,5-d][1,3]oxazine-5,7-dione |

-continued

| No. | Structure | Name |
|---|---|---|
| B35 | 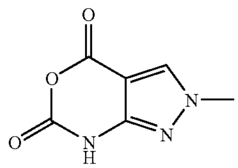 | 2-methyl-2,7-dihydropyrazolo[3,4-d][1,3]oxazine-4,6-dione |
| B36 | 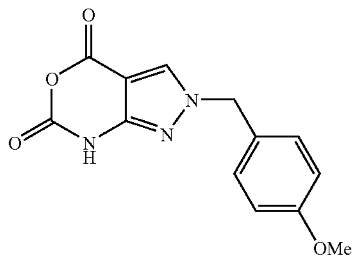 | 2-(4-methoxybenzyl)-2,7-dihydropyrazolo[3,4-d][1,3]oxazine-4,6-dione |
| B37 | 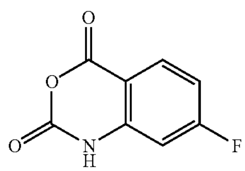 | 4-fluoroisatoic anhydride |

The following intermediates were prepared by the method of Washburne and Park, Tet Lett. 243 (1976):

| No. | Structure | Name |
|---|---|---|
| B40 | 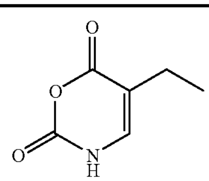 | 5-ethyl-3H-[1,3]oxazine-2,6-dione |
| B41 | 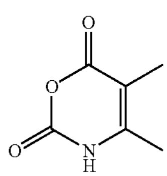 | 4,5-dimethyl-3H-[1,3]oxazine-2,6-dione |

Intermediate B45—1,5,6,7-tetrahydrocyclopental[d][1,3]oxazine-2-4-dione

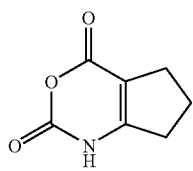

Tetramethylsilylazide (1.28 ml, 1 equiv) was added dropwise to a solution of 1-cyclopentene-1,2-dicarboxylic anhydride (1.33 g, 1 equiv) in dichloromethane (20 ml) and the mixture was warmed to 35° C. After ca. 4 h gas evolution had ceased. Ethanol (1 equiv) was added and stirring continued for 10 min, then the solvent was removed in vacuo and the residue triturated with ether to obtain the title compound (0.74 g). $^1$H-NMR (d$_6$-DMSO) δ 2.00 (2H, m), 2.47 (2H, m), 2.68 (2H, m), 11.8 (1H, br s); MS (APCI−) found (M−1)=152; $C_7H_7NO_3$ requires 153.

The following intermediate was prepared by the method of Int. B45

| No. | Structure | Name |
|---|---|---|
| B46 | 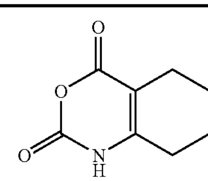 | 5,6,7,8-tetrahydro-1H-benzo[d][1,3]oxazine-2-4-dione |

Intermediate B50—Ethyl (2,4-dioxo-4H-pyrido[2,3-d][1,3]oxazin-1-yl)acetate

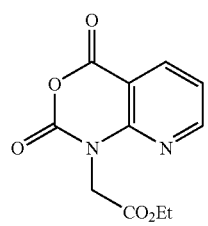

A 2:1 mixture of 3- and 6-azaisatoic anhydride (3.55 g, 21.6 mmol) (*Synthesis* 1982, 11, 972) was added portionwise to a suspension of sodium hydride (0.95 g, 60% in oil, 23.8 mmol) in DMF (40 ml). After stirring for 1 h, ethyl bromoacetate (2.64 ml, 23.8 mmol) was added. The reaction mixture was stirred overnight. The solvent was removed under reduced pressure. Ice/water was added to the residue and stirred for 1 h. The resulting pink solid was collected by filtration, washed with water and dried under vacuum at 40° C. The product was a 4:1 mixture of the [2,3-d] and the [3,2-d]isomers. $^1$H-NMR data of the title compound. $^1$H-NMR (d$_6$-DMSO) δ 1.21 (3H, t), 4.18 (2H, q), 4.92 (2H, s), 7.45 (1H, dd), 8.47 (1H, dd), 8.77 (1H, dd); MS (APCI+) found (M+1)=251; C$_{11}$H$_{10}$N$_2$O$_5$ requires 250.

The title compound could also be prepared by the following method:

To a stirring mixture of 3-azaisatoic anhydride (Int. B26) (84.36 g, 1 equiv) and N,N-diisopropylethylamine (94 ml, 1.05 equiv) in N-methylpyrrolidone (420 ml) was added dropwise under argon at 45–50° C., ethyl bromoacetate (57 ml, 1 equiv). After 16 h at 50° C. the mixture was cooled (ice bath) and water (560 ml) added with vigorous stirring. The solid which precipitated was filtered, washed with water and partitioned between ethyl acetate and saturated aqueous sodium bicarbonate. An insoluble solid was filtered off and discarded and the ethyl acetate layer washed again with saturated sodium bicarbonate, dried (Na$_2$SO$_4$) and evaporated. The residue was triturated with a 1:1 mixture of ether/light petrol, filtered, washed and dried to give the title compound as an off-white solid, yield (56.0 g).

The following intermediates were prepared by the method of Intermediate B50:

| No. | Precursor | Structure | Name |
|---|---|---|---|
| B51 | Int. B40 | 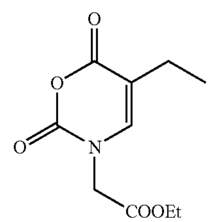 | ethyl (5-ethyl-2,6-dioxo-6H-[1,3]oxazin-3-yl) acetate |
| B52 | Int. B41 | 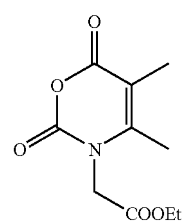 | ethyl (4,5-dimethyl-2,6-dioxo-6H-[1,3]oxazin-3-yl) acetate |
| B53 | Int. B37 | 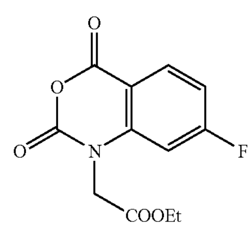 | ethyl 7-fluoro-2,4-dioxo-4H-benzo[d][1,3]-oxazin-1-yl) acetate |
| B54 | Int. B30 | 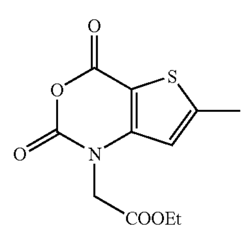 | ethyl (6-methyl-2,4-dioxo-4H-thieno[3,2-d][1,3]oxazin-1-yl) acetate |
| B55 | Int. B33 | 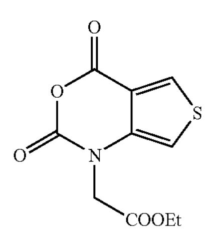 | ethyl (2,4-di-4H-thieno[3,4-d][1,3]oxazin-1-yl) acetate |

-continued

| No. | Precursor | Structure | Name |
|---|---|---|---|
| B56 | Int. B31 | 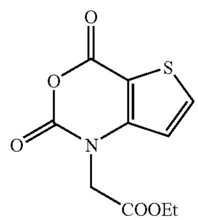 | ethyl (2,4-dioxo-4H-thieno[3,2-d]-[1,3]oxazin-1-yl) acetate |
| B57 | Int. B32 | 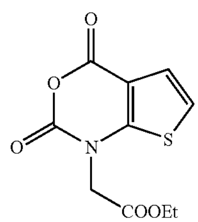 | ethyl (2,4-dioxo-4H-thieno[2,3-d]-[1,3]oxazin-1-yl) acetate |
| B58 | Int. B34 | 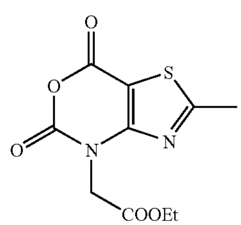 | ethyl (6-methyl-2,4-dioxo-4H-thiazolo[4,5-d][1,3]oxazin-1-yl) acetate |
| B59 | Int. B35 | 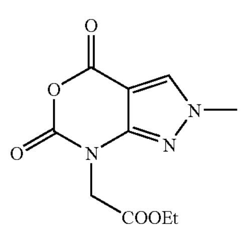 | ethyl (2-methyl-4,6-dioxo-2,4-dihydro-pyrazolo[3,4-d][1,3]oxazin-7-yl) acetate |
| B60 | Int. B36 | 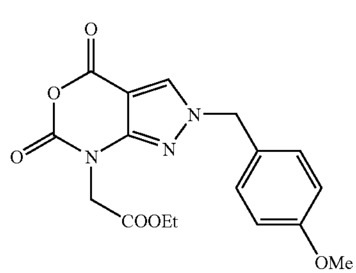 | ethyl (2-(4-methoxybenzyl)-4,6-dioxo-2,4-dihydropyrazolo[3,4-d][1,3]oxazin-7-yl)-acetate |

-continued

| No. | Precursor | Structure | Name |
|---|---|---|---|
| B61 | Int. B45 | 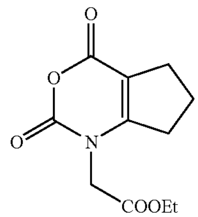 | ethyl (2,4-dioxo-1,5,6,7-tetrahydro-cyclopenta[d][1,3]oxazin-3-yl) acetate |
| B62 | Int. B46 | 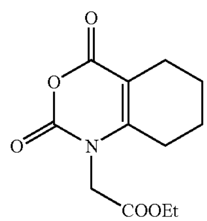 | ethyl (2,4-dioxo-5,6,7,8-tetrahydro-1H-benzo[d][1,3]oxazin-3-yl) acetate |

Intermediate
B70—5-(2,3-difluorophenyl)-3-oxopentanoic acid tert-butyl ester

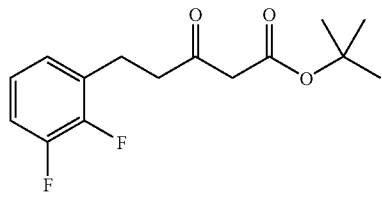

To an ice cooled stirring suspension of sodium hydride (1.96 g, 49.1 mmol, 60% dispersion in oil) in dry tetrahydrofuran (100 ml) was added dropwise under an argon atmosphere tert-butylacetoacetate (7.4 ml, 44.6 mmol). After a further 15 min, n-butyllithium (18.7 ml, 46.8 mmol, 2.5M in hexanes) was added dropwise maintaining the reaction temperature below 10° C. 2,3-Difluorobenzyl bromide (11.08 g, 53.5 mmol) was added dropwise 20 min later, then the mixture allowed to warm to ambient temperature. After a further 15 min the reaction mixture was poured onto a mixture of water (150 ml) and glacial acetic acid (10 ml), extracted 3 times with ethyl acetate and the combined extracts washed with saturated sodium hydrogen carbonate then brine, dried (MgSO$_4$) and evaporated to a yellow oil.

Chromatography (fine silica, ethyl acetate-light petrol) gave the title compound as a yellow oil, yield 9.05 g (71%). $^1$H-NMR (CDCl$_3$) δ 1.45 (9H, s), 2.84–2.91 (2H, m), 2.95–3.00 (2H, m), 3.35 (2H, s), 6.92–7.04 (3H, m).

Intermediate B71—(3-tert-butoxycarbonylmethyl-2-[2-(2,3-difluorophenyl)ethyl]-4-oxo-4H-[1,8]naphthyridin-1-yl)acetic acid ethyl ester

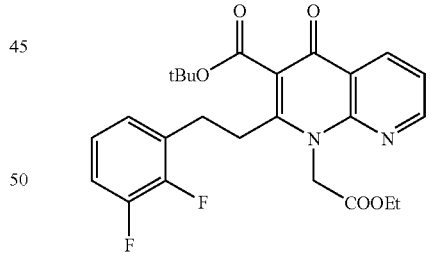

To a stirring suspension of sodium hydride (0.562 g, 14.06 mmol, 60% dispersion in oil) in dry DMF (50 ml) was added dropwise 5-(2,3-difluorophenyl)-3-oxopentanoic acid tert-butyl ester (Int. B70) (3.63 g, 12.78 mmol). After 10 min, (2,4-dioxo-4H-pyrido[2,3-d][1,3]oxazin-1-yl)acetic acid ethyl ester (Int. B50) (3.21 g, 12.78 mmol) was added and the mixture stirred for 16 h. The solvent was evaporated and the residue treated with saturated aq. ammonium chloride and extracted 3 times with ethyl acetate. The combined extracts were washed with brine, dried (MgSO$_4$) and concentrated. Chromatography (fine silica, ethyl acetate-light petrol) gave the title compound as a light brown solid, yield 1.88 g (31%). ¹H NMR (d6-DMSO) δ 1.31 (3H, t), 1.63 (9H, s), 2.95–3.03 (2H, m), 3.08–3.13 (2H, m), 4.27 (2H, q), 5.31 (2H, s), 7.01–7.11(3H, m), 7.35–7.38 (1H, m), 8.67–8.71 (2H, m).

The title compound was also made by the following method:

To an ice-cooled solution of intermediate B50 (55.9 g, 1 equiv) and intermediate B70 (63.5 g, 1 equiv) in dichloromethane (700 ml) was added dropwise under argon over 45 min 1,8-diazabicyclo[5.4.0]undec-7-ene (40 ml, 1.2 equiv). After 1 h the ice bath was removed and after a further 2.5 h the mixture was washed with saturated aqueous ammonium chloride, dried (Na₂SO₄) and evaporated. The crude product was chromatographed (fine silica, ethyl acetate-dichloromethane) then triturated with light petrol to give the title compound (80.27 g).

The following intermediates were prepared by the method of Intermediate B71:

| No. | Precursor | Structure | Name |
|-----|-----------|-----------|------|
| B72 | Int. B51 | 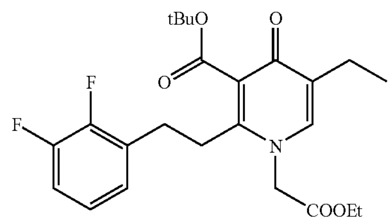 | 2-[2-(2,3-difluorophenyl)ethyl)-3-tert-butoxycarbonyl-5-ethyl-4-oxo-4H-pyridin-1-yl]acetic acid, ethyl ester |
| B73 | Int. B52 | 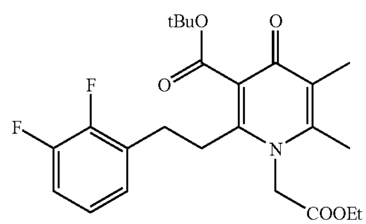 | 2-[2-(2,3-difluorophenyl)ethyl)-3-tert-butoxycarbonyl-5,6-dimethyl-4-oxo-4H-pyridin-1-yl]acetic acid, ethyl ester |
| B74 | Int. B54 | 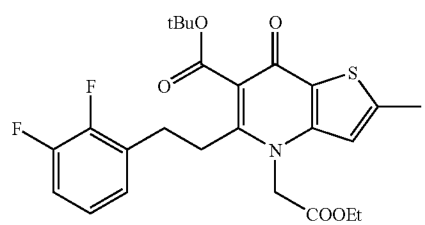 | 5-[2-(2,3-difluorophenyl)ethyl)-6-tert-butoxycarbonyl-2-methyl-7-oxo-7H-thieno[3,2-b]pyridin-4-yl]acetic acid, ethyl ester |
| B75 | Int. B55 | 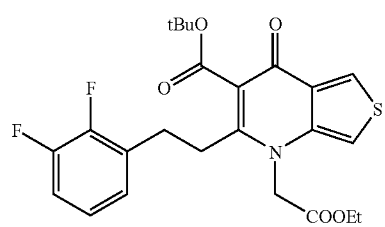 | 2-[2-(2,3-difluorophenyl)ethyl)-3-tert-butoxycarbonyl-4-oxo-4H-thieno[3,4-b]pyridin-1-yl]acetic acid, ethyl ester |
| B76 | Int. B58 | 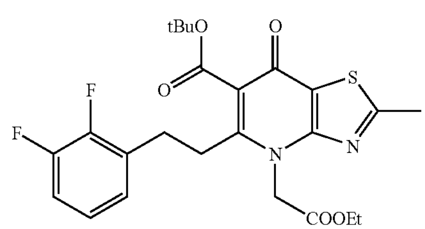 | 2-[5-(2,3-difluorophenyl)ethyl)-6-tert-butoxycarbonyl-2-methyl-7-oxo-7H-thiazolo[4,5-b]pyridin-4-yl]acetic acid, ethyl ester |

| No. | Precursor | Structure | Name |
|---|---|---|---|
| B77 | Int. B59 | 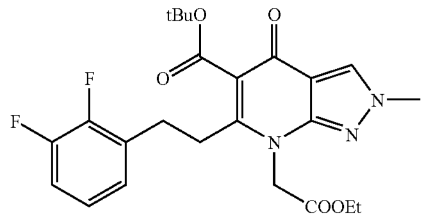 | 2-[6-(2,3-difluorophenyl)ethyl)-5-tert-butoxycarbonyl-2-methyl-4-oxo-4H-pyrazolo[3,4-b]pyridin-7-yl]acetic acid, ethyl ester |
| B78 | Int. B61 | 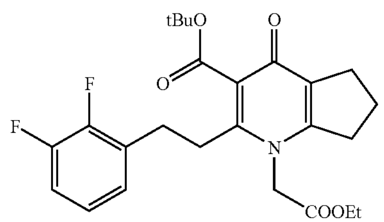 | 2-[2-(2,3-difluorophenyl)ethyl)-3-tert-butoxycarbonyl-4-oxo-5,6-trimethylenepyridin-1-yl]acetic acid, ethyl ester |
| B79 | Int. B62 | 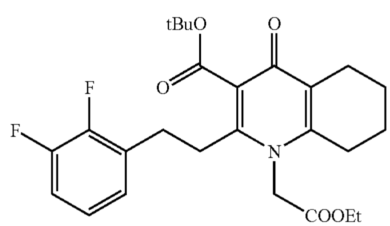 | 2-[2-(2,3-difluorophenyl)ethyl)-3-tert-butoxycarbonyl-4-oxo-5,6-tetramethylenepyridin-1-yl]acetic acid, ethyl ester |

Intermediate B80—5-(2,3-difluorophenyl)-3-oxopentanoic acid ethyl ester

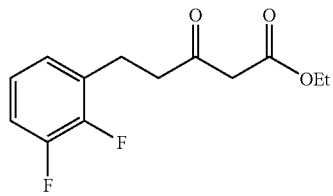

Prepared from ethyl acetoacetate by the method of Int. B70. $^1$H-NMR (CDCl$_3$) δ 1.27 (3H, t), 2.86–3.02 (4H, m), 3.43 (2H, s), 4.18 (2H, q), 6.92–7.07 (3H, m).

Intermediate B91—Ethyl 2-[6-(2-(2,3-difluorophenyl)ethyl)-2-(4-methoxybenzyl)-4-oxo-2,4-dihydropyrazolo[3,4-b]pyridin-7-yl]acetate

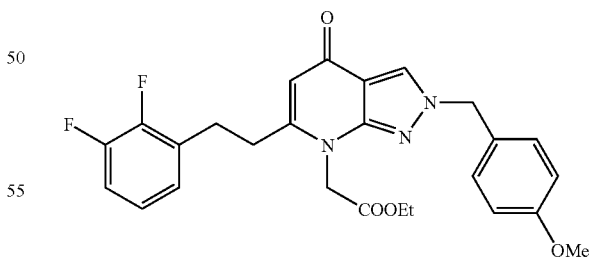

To sodium hydride (0.315 g) in dry DMF (8 ml) at 0° C. under argon was added a solution of intermediate B70 (2.23 g) in dry DMF (8 ml) dropwise. After stirring at 0° C. for 30 min, a solution of intermediate B60 (2.82 g) in dry DMF was added and the mixture allowed to warm to room temperature. After 4 h at room temperature, the mixture was poured into saturated ammonium chloride solution and extracted with ethyl acetate. The combined extracts were dried over MgSO₄ and evaporated under reduced pressure to give an oil that was chromatographed on silica gel. This gave a yellow oil (2.3 g). A portion of this material (0.50 g) in TFA (5 ml) was stirred at room temperature for 4 h, then evaporated to dryness. A portion of the residue was added to diphenyl ether (5 ml), heated to reflux for 40 min, then cooled and poured into hexane. The precipitate was filtered off and washed with hexane to obtain the title compound. ¹H-NMR (CDCl₃) δ 1.27 (3H, t), 2.81 (2H, m), 3.01 (2H, m), 3.81 (3H, s), 4.25 (2H, q), 4.93 (2H, s), 5.27 (2H, s), 5.96 (1H, s), 6.88–7.10 (5H, m), 7.23 (2H, d), 7.88 (1H, s).

Intermediate B92—Ethyl 2-[6-(2-(2,3-difluorophenyl)ethyl)-4oxo-2,4-dihydropyrazolo[3,4-b]-pyridin-7-yl]acetate

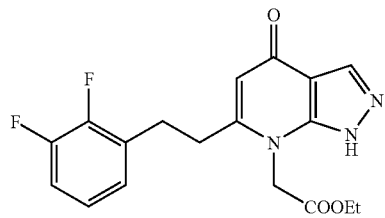

A mixture of Int. B91 (0.48 g) and TFA (50 ml) was heated at reflux for 17 h, then the TFA was removed in vacuo. The residue was extracted with dichloromethane, and the combined extracts were chromatographed (silica, 10% methanol in dichloromethane) to obtain the title compound as a dark solid (0.23 g, 64%). ¹H-NMR (CDCl₃) δ 1.27 (3H, t), 2.85 (2H, m), 3.02 (2H, m), 4.25 (2H, q), 4.97 (2H, s), 6.01 (1H, s), 6.95–7.09 (3H, m), 8.24 (1H, s).

Intermediate B93—5-(2-(2,3-Difluorophenyl)ethyl)-3-(pyrazol-4-ylamino)pent-2-enoic acid ethyl ester

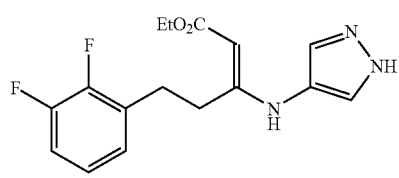

4-Nitropyrazole (3.55 g, 1 equiv) in ethanol (150 ml) was hydrogenated over 10% palladium on charcoal, then the catalyst was filtered off, Int. B80 (8.0 g, 1 equiv) was added and the solvent was removed in vacuo. Concentrated hydrochloric acid (0.5 ml) was added, and the mixture was heated to 100° C. under argon for 2 h. Ethyl acetate was added and the solution was washed with aq. sodium bicarbonate, dried and evaporated. Chromatography (silica, dichloromethane/ ethyl acetate) yielded the title compound as a pale solid (5.7 g, 56%). ¹H-NMR (CDCl₃) δ 1.29 (3H, t), 2.48 (2H, t), 2.80 (2H, t) 4.15 (2H, q), 4.74 (1H, s), 6.78 (1H, m), 6.95 (2H, m), 7.46 (2H, s), 9.75 (1H, s), 11.1 (1H, br s).

Intermediate B94—5-(2-(2,3-Difluorophenyl)ethyl)-2,4-dihydropyrazolo[4,3-b]pyridin-7-one

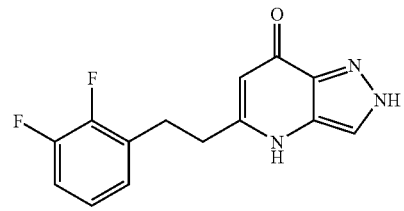

Intermediate B93 (6.7 g) was added portionwise to refluxing Dowtherm (100 ml) and heating was continued for 1 h. After cooling, the mixture was poured into hexane and the precipitate was filtered off, washed with hexane and dried; yield 4.5 g (78%). ¹H-NMR (d₆-DMSO) δ 2.89 (2H, m), 3.06 (2H, m), 5.81 (1H, s), 7.07–7.36 (3H, m), 7.76 (1H, s), 11.7 (1H, br s), 13.6 (1H, br s).

Intermediate B95—7-Chloro-5-(2-(2,3-difluorophenyl)ethyl)-2,4-dihydropyrazolo[4,3-b]pyridine

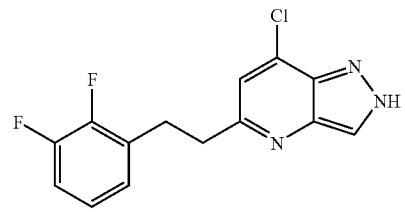

A mixture of Intermediate B94 (4.5 g) and phosphorus oxychloride (90 ml) was heated at reflux for 2 h, then excess phosphorus oxychloride was removed in vacuo and the residue was poured into water and basified with sodium bicarbonate. The product was extracted into ethyl acetate and the extracts dried and evaporated to obtain the title compound (4.6 g, 96%). ¹H-NMR (CDCl₃) δ 3.22 (4H, m), 6.89–7.06 (3H, m), 7.21 (1H, s), 8.34 (1H, s), 11.0 (1H, br s).

Intermediates B96 and B97—5-(2-(2,3-difluorophenyl)ethyl)-1-methyl-2,4-dihydropyrazolo[4,3-b]-pyridin-7-one and 5-(2-(2,3-difluorophenyl)ethyl)-2-methyl-2,4-dihydropyrazolo[4,3-b]pyridin-7-one

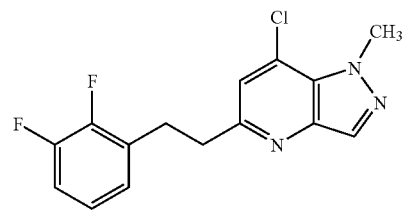

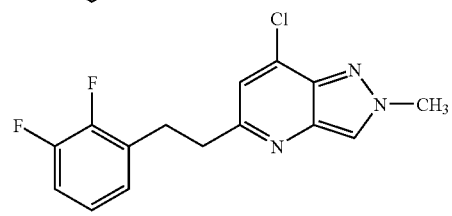

A mixture of Intermediate B95 (4.3 g, 1 equiv), sodium hydroxide (1.5 g, 2.5 equiv) and 90% aq. ethanol (15 ml) was heated to reflux and a solution of iodomethane (1.82 ml, 2 equiv) in diethyl ether (15 ml) was added dropwise (CARE). After 3 h at reflux a further 2 equivalents of iodomethane was added, and heating was continued for 2 h. The solvent was removed in vacuo, the residue was dissolved in ethyl acetate, and the solution washed with water, dried and evaporated to obtain a crude mixture of products in a ratio of ca. 3:2. These were separated by chromatography (silica, dichloromethane-ethyl acetate). Early fractions gave the 1-methyl isomer (Int. B96, 2.1 g); $^1$H-NMR (CDCl$_3$) δ 3.17 (4H, m), 4.36 (3H, s), 6.90–7.04 (3H, m), 7.12 (1H, s), 8.15 (1H, s). Later fractions gave the 2-methyl isomer (Int. B97, 1.2 g); $^1$H-NMR (CDCl$_3$) δ 3.16 (4H, m), 4.29 (3H, s), 6.90–7.04 (3H, m), 7.15 (1H, s), 8.14 (1H, s). The identity of the two isomers was confirmed by NOE experiments.

Intermediate B98—5-(2-(2,3-Difluorophenyl)ethyl)-1-methyl-2,4-dihydropyrazolo[4,3-b]pyridin-7-one

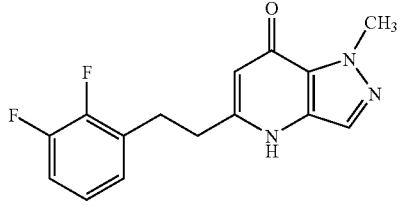

A mixture of Int. B96 (2.1 g), 2M hydrochloric acid (10 ml) and dioxan (3 ml) was heated at reflux for 4 days, then extracted with dichloromethane/methanol. Drying and evaporation of the extracts gave the title compound (1.7 g). $^1$H-NMR (d$_6$-DMSO) δ 2.98–3.14 (4H, m), 4.22 (3H, s), 6.22 (1H, s), 7.12–7.33 (3H, m), 7.89 (1H, s), 13 (1H, v br s); MS (APCI+) found (M+1)=290. C$_{15}$H$_{13}$F$_3$N$_2$O requires 289.

Intermediate B99—5-(2-(2,3-Difluorophenyl)ethyl)-2-methyl-2,4-dihydropyrazolo[4,3-b]pyridin-7-one

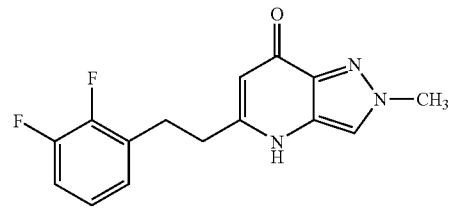

Hydrolysis of Int. B97 was carried out by the method of Int. B98. $^1$H-NMR (d$_6$-DMSO) δ 2.82 (2H, m), 3.03 (2H, m), 4.02 (3H, s), 5.66 (1H, s), 7.10 (2H, m), 7.25 (1H, m), 8.00 (1H, s), 11.5 (1H, v br s); MS (APCI+) found (M+1)= 290. C$_{15}$H$_{13}$F$_3$N$_2$O requires 289.

Intermediate B100—Dimethyloxosulphonium-2-(ethoxycarbonylmethylamino)benzoylmethylide

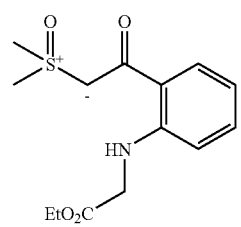

To a solution of trimethylsulphoxonium iodide (99 g, 0.45 mol) in DMSO (1 L) at 5° C. was added sodium hydride (19.4 g, 0.485 mol, 60% in oil) over 0.5 h and the solution stirred for a further 0.5 h until the reaction subsided. Ethyl 2-(2,4-dioxo-4H-benzo[d][1,3]oxazin-1-yl)acetate (110 g, 0.44 mol) was then added to the solution over 0.33 h and stirred for a further 3 h after which time the reaction mixture was heated at 50° C. for 1.5 h. After cooling to ambient the solution was poured onto ice and the precipitate filtered off and washed with water then pentane. The solids were dried in vacuo at 40° C. to provide the product (124.4 g, 94%). $^1$H-NMR (d$_6$-DMSO) δ 1.2 (3H, t), 3.5 (6H, s), 3.98 (2H, d), 4.15 (2H, q), 5.46 (1H, s), 6.44 (1H, d), 6.52 (1H, t), 7.17 (1H, t), 7.47 (1H, d), 8.93 (1H, br t).

The following intermediates were prepared by the method of intermediate B100

| No. | Precursor | Structure | Name |
|---|---|---|---|
| B101 | Int. B53 | ![structure] | Dimethyloxosulphonium-2-(ethoxycarbonylmethylamino)-4-fluorobenzoylmethylide |

-continued

| No. | Precursor | Structure | Name |
|---|---|---|---|
| B102 | Int. B56 | 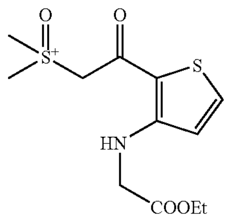 | Dimethyloxosulphonium-3-(ethoxycarbonyl-methylamino)thien-2-ylcarbonylmethylide |
| B103 | Int. B57 | 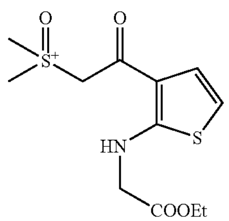 | Dimethyloxosulphonium-2-(ethoxycarbonyl-methylamino)thien-3-ylcarbonylmethylide |
| B104 | Int. B59 | 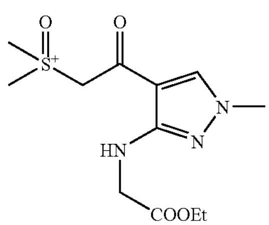 | Dimethyloxosulphonium-3-(ethoxycarbonyl-methylamino)-1-methylpyrazin-4-ylcarbonylmethylide |
| B105 | Int. B50 | 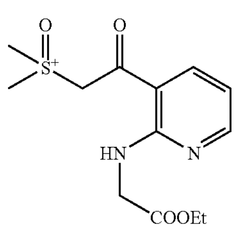 | Dimethyloxosulphonium-2-(ethoxycarbonyl-methylamino)pyridin-3-ylcarbonylmethylide |

Intermediate B110—5-(1-(2,3-Difluorobenzylthio)-1-phenylaminomethylene)-2,2-dimethyl-[1,3]dioxane-4,6-dione

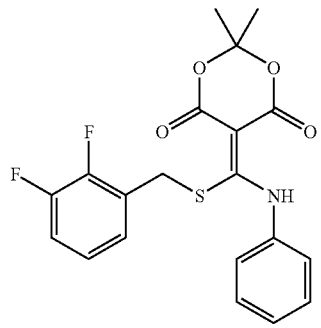

To hexane washed sodium hydride (7.45 g, 60% in oil) under argon, was added N-methylpyrrolidone (NMP) (270 ml) and the mixture cooled in an ice-salt bath. 2,2-Dimethyl-1,3-dioxane-4,6-dione (26.8 g) was added portionwise over 20 min keeping the temperature between 5–10° C. Effervescence was noted during the addition. The mixture was stirred at room temperature for 1 h and phenylisothiocyanate (25.2 g) added over 15 min. The mixture was stirred at room temperature for 2.5 h and cooled to 15° C. in a cold water bath. 2,3-Difluorobenzyl bromide (38.6 g) was added over 10 min and stirred at room temperature overnight. The solvent was removed under reduced pressure and the residue partitioned between ethyl acetate (1.2 L) and water. The organic layer was washed with further water and then brine and dried over MgSO$_4$. The solvent was removed under reduced pressure and the residue triturated with 40–60° C. petrol and the solid collected by filtration. Crystallisation from methyl t.butyl ether gave the title compound as a pale yellow solid (51.4 g). $^1$H-NMR (d$_6$-DMSO) δ 1.64 (6H, s), 4.16 (2H, d), 7.1–7.25 (2H, m), 7.25–7.5 (6H, m), 12.12 (1H, br s); MS (APCI−) found (M−1)=404. C$_{20}$H$_{17}$F$_2$NO$_4$S requires 405.

Intermediate B111—Ethyl 2-(1-(2,3-difluorobenzylthio)-1-(2,2-dimethyl-4,6-dioxo-[1,3]dioxan-5-ylidene)-methyl)phenylamino)acetate

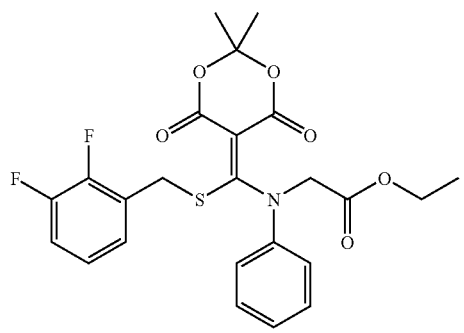

To hexane washed sodium hydride (1.0 g, 60% in oil) under argon, was added NMP (30 ml). A solution of 5-(1-(2,3-Difluorobenzylthio)-1-phenylaminomethylene)-2,2-dimethyl-[1,3]dioxane-4,6-dione (10.0 g) (intermediate B110) in NMP (20 ml) was added by syringe over 15 min at room temperature and stirred for 30 min. Ethyl bromoacetate (4.5 g) was added and the mixture heated at 60° C. for 6 h. The mixture was partitioned between ethyl acetate and water and the aqueous layer extracted with further ethyl acetate. The combined organic layers were washed with further water and brine, dried over MgSO$_4$, and the solvent removed under reduced pressure. The orange oil so obtained was triturated with diethyl ether/40–60° C. petrol to give a solid that was collected by filtration. This solid was recrystallised from methyl t-butyl ether to give the title compound (7.37 g). $^1$H-NMR (d$_6$-DMSO) δ 1.24 (3H, t), 1.55 (6H, br s), 4.19 (2H, q), 4.37 (2H, d), 4.81 (2H, br s), 6.85–7.5 (8H, 2×m).

Intermediate B112—2-(2-(2,3-Difluorophenyl)ethyl)-6-methylpyrido[1,2-a]pyrimid-4-one

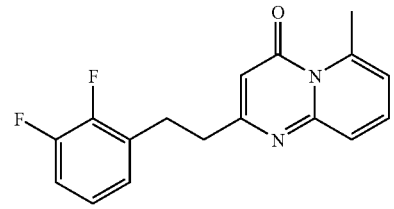

A mixture of 2-amino-6-methylpyridine (0.55 g, 1 equiv), Int. B80 (1.5 g, 1.15 equiv) and polyphosphoric acid (3 ml) was heated to 110° C. for 6 h, then ice/water was added and the solution adjusted to pH 7 with aq. sodium hydroxide. The precipitate was filtered off, washed with water and dried to obtain the title compound (1.3 g). $^1$H-NMR (d$_6$-DMSO) δ 2.89 (2H, m), 3.04 (3H, s), 3.12 (2H, m), 6.11 (1H, s), 6.62 (1H, d), 6.95–7.04 (3H, m), 7.35–7.44 (2H, m); MS (APCI+) found (M+1)=301. C$_{17}$H$_{14}$F$_2$N$_2$O requires 300.

Intermediate B113—2-(2-(2,3-Difluorophenyl)ethyl)-7-methyl-1H-[1,8]naphthyridin-4-one

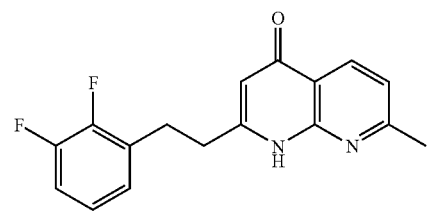

A mixture of Int. B112 (1.0 g) and diphenyl ether (10 ml) was heated to reflux for 4 h, then cooled to 0° C. The resulting solid was filtered off, washed thoroughly with hexane and dried to obtain the title compound (0.67 g). $^1$H-NMR (d$_6$-DMSO) δ 2.58 (3H, s), 2.91 (2H, m), 3.09 (2H, m), 5.90 (1H, s), 6.62 (1H, d), 7.10–7.30 (4H, m), 8.26 (1H, d); MS (APCI+) found (M+1)=301. C$_{17}$H$_{14}$F$_2$N$_2$O requires 300.

Intermediate C1—2-(2,3-Difluorobenzylthio)-1H-quinolin-4-one

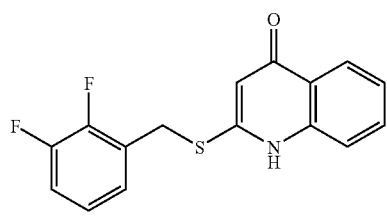

A mixture of 4-allyloxy-2-(2,3-difluorobenzylthio)quinoline (Int. B22) (2.24 g), triphenylphosphine rhodium (I) chloride (0.302 g, 5 mol %) and 1,4-diazobicyclo[2,2,2]octane (0.147 g, 20 mol %) in ethanol (30 ml) and water (1.5 ml) was heated to reflux for 4 h. The solvent was removed and the residue partitioned between water and dichloromethane, the organic phase dried and evaporated. Chromatography (silica, 4% methanol in dichloromethane) yielded the title compound as an off white solid (1.25 g). $^1$H-NMR (d$_6$-DMSO) δ 4.55 (2H, s), 6.37 (1H, br s), 7.15 (1H, m), 7.31 (3H, m), 7.65 (2H, m), 8.02 (1H, d), 11.75 (1H, br s); MS (APCI+) found (M+1)=304. $C_{16}H_{11}F_2NOS$ requires 303.

The following intermediate was prepared by the method of intermediate C1:

| No. | Precursor | Structure | Name |
|---|---|---|---|
| C2 | Int. B23 | 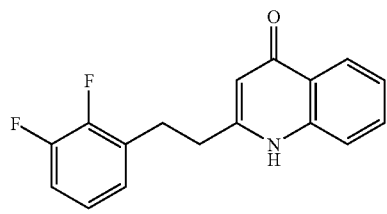 | 2-(4-Fluorobenzylthio)-1H-quinolin-4-one |

Intermediate C3—2-(2-(2,3-Difluorophenyl)ethyl)-1H-quinolin-4-one

4-Chloro-2-(2,3-difluorophenylethyl)quinoline (Int B10) (2.83 g) was heated to reflux in aqueous hydrochloric acid (2M, 15 ml) and dioxane (6 ml) for 72 h. The reaction mixture was extracted with dichloromethane (90 ml) and methanol (10 ml), and the organic phase dried and evaporated to give the title compound as a white solid (2.61 g). $^1$H-NMR (d$_6$-DMSO) δ 3.15 (4H, s), 6.46 (1H, s), 7.15 (2H, m), 7.27 (1H, m), 7.51 (1H, m), 7.82 (2H, m), 8.15 (1H, d); MS (APCI+) found (M+1)=286. $C_{17}H_{13}F_2NO$ requires 285.

The following intermediates were prepared by the method of intermediate C3:
| No. | Precursor | Structure | Name |
|-----|-----------|-----------|------|
| C4 | Int. B11 | 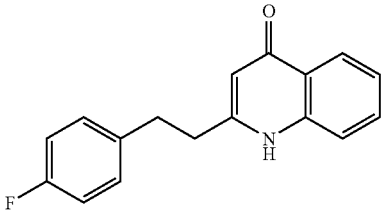 | 2-(2-(4-Fluorophenyl)ethyl)-1H-quinolin-4-one |
| C5 | Int. B12 | 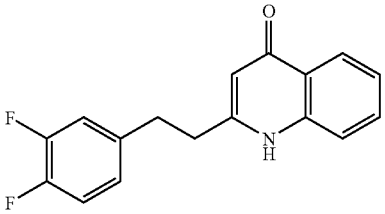 | 2-(2-(3,4-Difluorophenyl)ethyl)-1H-quinolin-4-one |
| C6 | Int. B13 | 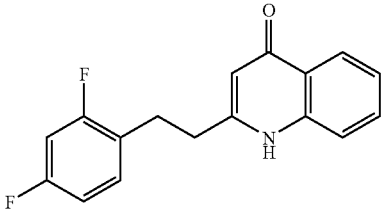 | 2-(2-(2,4-Difluorophenyl)ethyl)-1H-quinolin-4-one |
| C7 | Int. B14 | 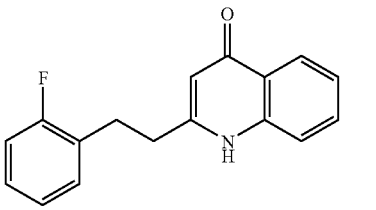 | 2-(2-(2-Fluorophenyl)ethyl)-1H-quinolin-4-one |
| C8 | Int. B15 | 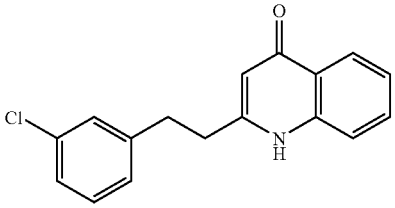 | 2-(2-(3-Chlorophenyl)ethyl)-1H-quinolin-4-one |

-continued

| No. | Precursor | Structure | Name |
|---|---|---|---|
| C9 | Int. B16 | 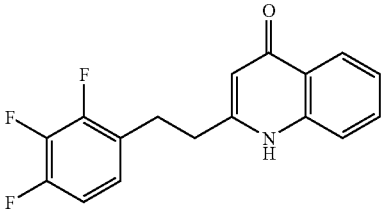 | 2-(2-(2,3,4-Trifluorophenyl)ethyl)-1H-quinolin-4-one |
| C10 | Int. B17 | 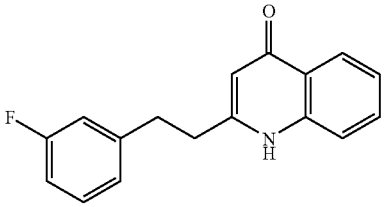 | 2-(2-(3-Fluorophenyl)ethyl)-1H-quinolin-4-one |

Intermediate C11—2-(4-Fluorobenzylthio)-1,5,6,7-tetrahydro-[1]pyrindin-4-one

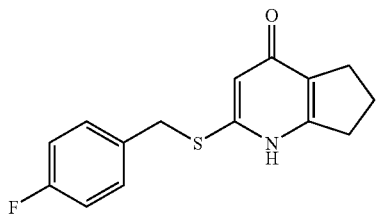

A mixture of 2-(4-fluorobenzylthio)-1-oxy-6,7-dihydro-5H-[1]pyrindin-4-ol (Int. B9) (1.54 g) and palladium/carbon (0.3 g, 20 wt %) in acetic acid (80 ml) was heated to 50° C. in an atmosphere of H$_2$ at 50 psi overnight. The catalyst was filtered off and solvent evaporated to give the title compound as a brown foam (1.21 g). $^1$H-NMR (CDCl$_3$) δ 2.03 (2H, m), 2.81 (4H, m), 4.14 (2H, s), 6.46 (1H, s), 6.89 (2H, m), 7.21 (2H, m); MS (APCI+) found (M+1)=276. C$_{15}$H$_{14}$FNOS requires 275.

The following intermediate was prepared by the method of Int. C11

Intermediate D1—[2-(2,3-Difluorobenzylthio)-4-oxo-4H-quinolin-1-yl]acetic acid tert butyl ester

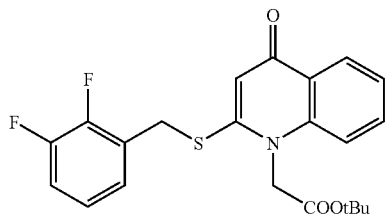

Butyllithium (2.5 M in hexanes, 1.52 ml, 1.05 equiv) was added dropwise to a solution of 2-(2,3-difluorobenzylthio)-1H-quinolin-4-one (Int. C1) (1.1 g, 1 equiv) in tetrahydrofuran (20 ml) at 0° C. under argon. The reaction mixture was stirred for 10 min prior to the addition of t-butyl bromoacetate (1.76 ml), 3 equiv) and stirring continued for 60 h at 45° C. The solution was diluted with dichloromethane (40 ml) and washed with aqueous ammonium chloride and aqueous sodium bicarbonate, dried and evaporated. Chromatography (silica, 5% [2M ammonia in methanol] in dichloromethane) yielded the title compound as a yellow

| No. | Precursor | Structure | Name |
|---|---|---|---|
| C12 | Int. B25 | 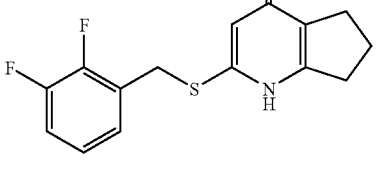 | 2-(2,3-Difluorobenzylthio)-1,5,6,7-tetrahydro-[1]pyrindin-4-one | foam (0.193 g). $^1$H-NMR (CDCl$_3$) δ 1.44 (9H, s), 4.29 (2H, s), 5.30 (2H, br s), 6.45 (1H, s), 7.06–7.24 (4H, m), 7.39 (1H, t), 7.63 (1H, dt), 8.41 (1H, dd); MS (APCI+) found (M+1) 418. C$_{22}$H$_{21}$F$_2$NO$_3$S requires 417.

The following intermediates were prepared by the method of Intermediate D1:

| No. | Precursor | Structure | Name |
|---|---|---|---|
| D2 | Int. C3 | 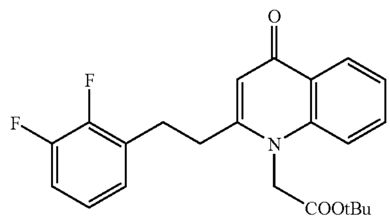 | [2-(2-(2,3-Difluorophenyl)ethyl)-4-oxo-4H-quinolin-1-yl]acetic acid tert butyl ester. |
| D3 | Int. C2 | 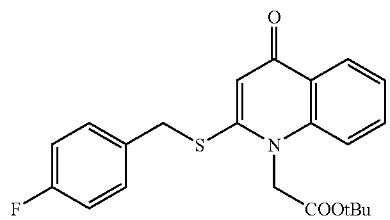 | [2-(4-Fluorobenzylthio)-4-oxo-4H-quinolin-1-yl]acetic acid tert butyl ester. |
| D4 | Int. C4 | 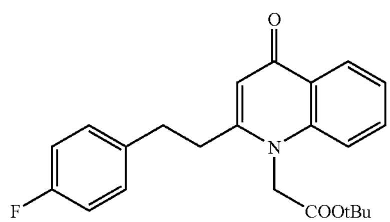 | [2-(2-(4-Fluorophenyl)ethyl)-4-oxo-4H-quinolin-1-yl]acetic acid tert butyl ester. |
| D5 | Int. C5 | 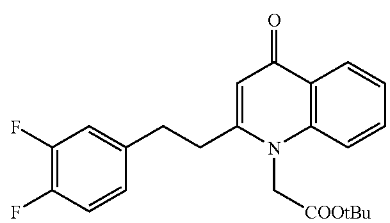 | [2-(2-(3,4-Difluorophenyl)ethyl)-4-oxo-4H-quinolin-1-yl]acetic acid tert butyl ester. |
| D6 | Int. C6 | 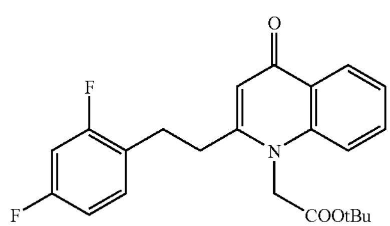 | [2-(2-(2,4-Difluorophenyl)ethyl)4-oxo-4H-quinolin-1-yl]acetic acid tert butyl ester. |
| D7 | Int. C7 | 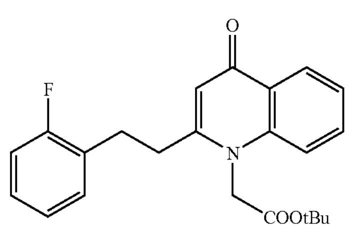 | [2-(2-(2-Fluorophenyl)ethyl)-4-oxo-4H-quinolin-1-yl]acetic acid tert butyl ester. |

-continued

| No. | Precursor | Structure | Name |
|---|---|---|---|
| D8 | Int. C8 | 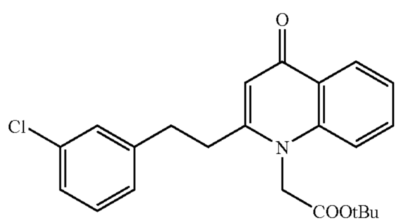 | [2-(2-(3-Chlorophenyl)ethyl)-4-oxo-4H-quinolin-1-yl]acetic acid tert butyl ester. |
| D9 | Int. C9 | 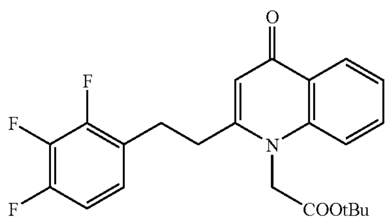 | [2-(2-(2,3,4-Trifluorophenyl)ethyl)-4-oxo-4H-quinolin-1-yl]acetic acid tert butyl ester. |
| D10 | Int. C10 | 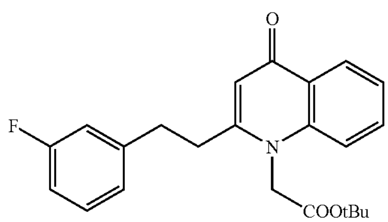 | [2-(2-(3-Fluorophenyl)ethyl)-4-oxo-4H-quinolin-1-yl]acetic acid tert butyl ester. |
| D11 | Int. B99 | 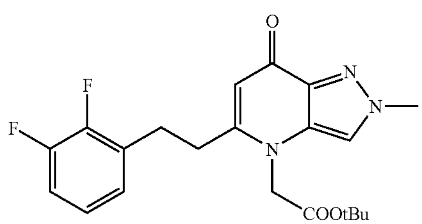 | t-Butyl [5-(2-(2,3-difluorophenyl)ethyl)-2-methyl-7-oxo-2,7-dihydropyrazolo[4,3-b]-pyridin-4-yl]acetate |
| D12 | Int. B98 | 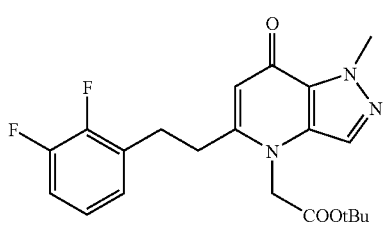 | t-Butyl [5-(2-(2,3-difluorophenyl)ethyl)1-methyl-7-oxo-1,7-dihydropyrazolo[4,3-b]-pyridin-4-yl]acetate |
| D13 | Int. C12 | 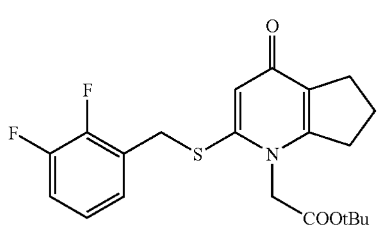 | t-Butyl [2-(2,3-difluorobenzylthio)-4-oxo-5,6-trimethylenepyridin-1-yl]acetate |
| D14 | Int. C3 | 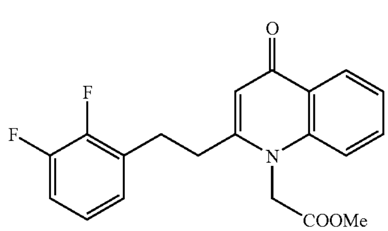 | Methyl 2-(2-(2-(2,3-difluorophenyl)ethyl)-4-oxo-4H-quinolin-1-yl)acetate |

| No. | Precursor | Structure | Name |
|---|---|---|---|
| D15 | Int. B113 | 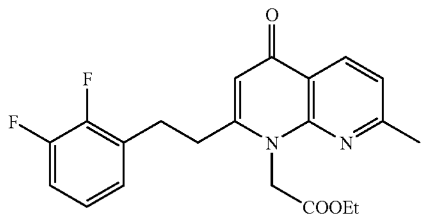 | Ethyl [2-(2-(2,3-difluorophenyl)ethyl)-7-methyl-4-oxo-4H-[1,8]naphthyridin-1-yl]-acetate |

Intermediate D20—[2-(4-Fluorobenzylthio)-4-oxo-4,5,6,7-tetrahydro-[1]pyrindin-1-yl]acetic acid tert butyl ester

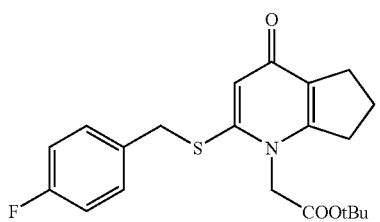

A mixture of 2-(4-fluorobenzylthio)-1,5,6,7-tetrahydro-[1]pyrindin-4-one (Int. C11) (1.21 g, 1 equiv), t-butyl iodoacetate (3.18 g, 3 equiv) and diisopropylethylamine (3.05 ml, 4 equiv) in dichloromethane (40 ml) was stirred at ambient temperature under argon for 48 h, then the solution was washed with aqueous ammonium chloride and aqueous sodium bicarbonate, dried and evaporated. Chromatography (silica, 5% methanol in dichloromethane) yielded the title compound as a off white foam (0.982 g). $^1$H-NMR (CDCl$_3$) δ 1.47 (9H, s), 2.09 (2H, m), 2.84 (4H, m), 4.07 (2H, s), 4.56 (2H, s), 6.45 (1H, s), 6.99 (2H, m), 7.25 (2H, m); MS (APCI+) found (M+1)=390. $C_{21}H_{24}FNO_3S$ requires 389.

Intermediate D25—Ethyl (2-(2,3-difluorobenzylthio)-4-oxo-4H-quinolin-1-yl)acetate

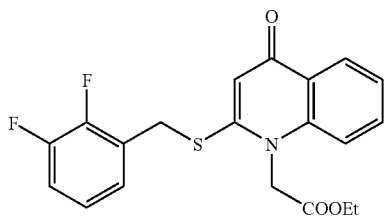

(a) A mixture of dimethyloxosulphonium-2-(ethoxycarbonylmethylamino)benzoylmethylide (0.30 g, 1.01 mmol) (intermediate B100), carbon disulphide (0.13 ml, 2.05 mmol) and diisopropylethylamine (0.35 ml, 2.02 mmol) in DMF (4 ml) was shaken under argon for 18 h then 2,3-difluorobenzyl bromide (0.42 g, 2.02 mmol) added and the reaction shaken for a further 7 h. The solution was concentrated and the residues separated between ethyl acetate and water. The organics were isolated, dried (MgSO$_4$) and concentrated. Purification by chromatography over silica eluting using a gradient from dichloromethane to dichloromethane/ether 3:1 yielded the title compound (0.14 g, 36%). $^1$H-NMR (d$_6$-DMSO) δ 1.2 (3H, t, J=7 Hz), 4.18 (2H, q, J=7 Hz), 4.5 (2H, s), 5.3 (2H, s), 6.3 (1H, s), 7.18 (1H, m), 7.3 (1H, m), 7.4 (2H, m), 7.6 (1H, d, J=8.5 Hz), 7.7 (1H, t, J=7 Hz), 8.1 (1H, d, J=8 Hz). MS (APCI+) found (M+1)= 390. $C_{20}H_{17}F_2NO_3S$ requires 389.

(b) Ethyl (1-(2,3-difluorobenzylthio)-1-(2,2-dimethyl-4,6-dioxo-[1,3]dioxan-5-ylidene)-methyl)-phenylamino)acetate (intermediate B111) (0.85 g) under argon was stirred with trifluoroacetic acid (10 ml) at room temperature overnight. The mixture was evaporated under reduced pressure, dissolved in dichloromethane, washed with sodium bicarbonate solution and dried over Na$_2$SO$_4$. The solvent was removed under reduced pressure and the residue triturated with diethyl ether to give the title compound (0.43 g). $^1$H-NMR (CDCl$_3$) δ 1.27 (3H, t), 4.26 (2H, q), 4.29 (2H, s), 5.1 (2H, br s), 6.45 (1H, s), 6.95–7.25 (4H, m), 7.39 (1H, t), 7.64 (1H, dt), 8.42 (1H, dd). Mass spectrum as above.

Intermediate D26—(2-(2-(2,3-difluorophenyl)ethyl)-4-oxo-4H-[1,8]naphthyridin-1-yl)acetic acid ethyl ester

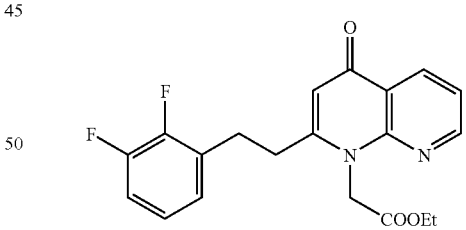

(3-tert-Butoxycarbonylmethyl-2-[2-(2,3-difluorophenyl)ethyl]-4-oxo-4H-[1,8]naphthyridin-1-yl)acetic acid ethyl ester (Int. B71) (1.35 g, 2.86 mmol) was added portionwise to boiling diphenyl ether (10 ml) with stirring. After 20 min, the dark solution was allowed to cool to ambient temperature. Petroleum ether (b.p. 60–80° C.) was added to the point of cloudiness to give the product as a crystalline solid (0.724 g). $^1$H NMR (d$_6$-DMSO) δ 1.19 (3H, t), 3.02–3.09 (4H, m), 4.16 (2H, q), 5.31 (2H, s), 6.10 (1H, s), 7.13–7.21 (2H, m), 7.26–7.33 (1H, m), 7.46–7.49 (1H, m), 8.49 (1H, m), 8.76 (1H, m). MS (APCI+), found (M+1)=373. $C_{20}H_{18}F_2N_2O_3$ requires 372.

The following intermediates were prepared by the method of Intermediate D26:

| No. | Precursor | Structure | Name |
|---|---|---|---|
| D27 | Int. B72 | 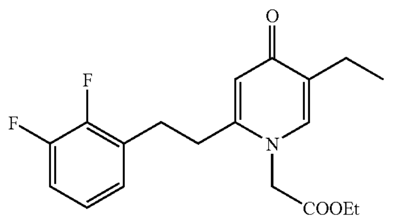 | Ethyl [2-(2-(2,3-difluorophenyl)ethyl)-5-ethyl-4-oxo-4H-pyridin-1-yl]acetate |
| D28 | Int. B73 | 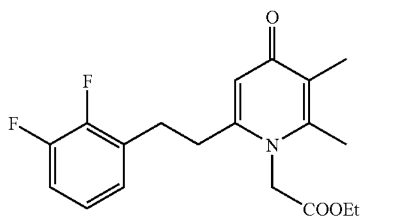 | Ethyl [2-(2-(2,3-difluorophenyl)ethyl)-5,6-dimethyl-4-oxo-4H-pyridin-1-yl]-acetate |
| D29 | Int. B74 | 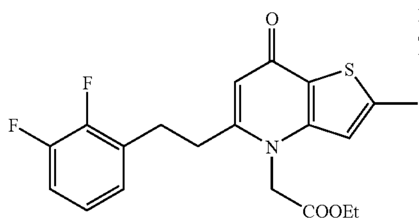 | Ethyl 5-[2-(2-(2,3-difluorophenyl)ethyl)-2-methyl-7-oxo-7H-thieno[3,2-b]pyridin-4-yl]acetate |
| D30 | Int. B75 | 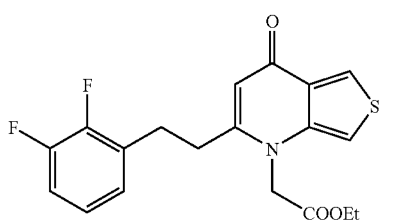 | Ethyl [2-(2-(2,3-difluorophenyl)ethyl)-4-oxo-4H-thieno[3,4-b]pyridin-1-yl)-acetate |
| D31 | Int. B76 | 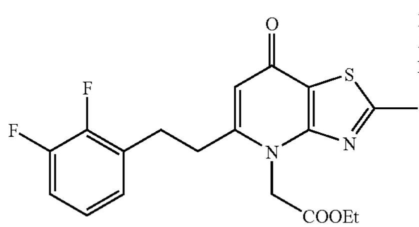 | Ethyl [5-(2-(2,3-difluorophenyl)ethyl)-2-methyl-7-oxo-7H-thiazolo[4,5-b]-pyridin-4-yl]acetate |
| D32 | Int. B77 | 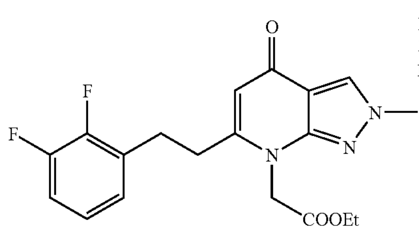 | Ethyl [6-(2-(2,3-difluorophenyl)ethyl)-2-methyl-4-oxo-4H-pyrazolo[3,4-b]-pyridin-7-yl]acetate |

-continued

| No. | Precursor | Structure | Name |
|---|---|---|---|
| D33 | Int. B78 | 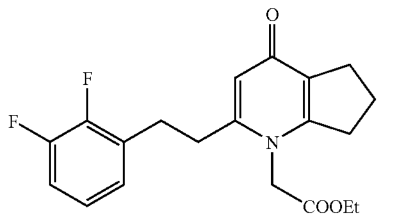 | Ethyl [2-(2-(2,3-difluorophenyl)ethyl)-4-oxo-5,6-trimethylenepyridin-1-yl]-acetate |
| D34 | Int. B79 | 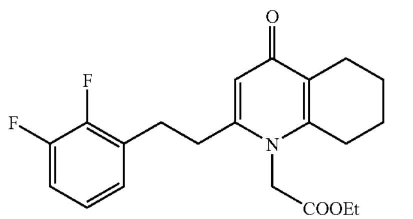 | Ethyl [2-(2-(2,3-difluorophenyl)ethyl)-4-oxo-5,6-tetramethylenepyridin-1-yl]-acetate |

The following intermediates were prepared by the method of Intermediate D25, method A:

| No. | Precursor | Structure | Name |
|---|---|---|---|
| D40 | Int. B101 | 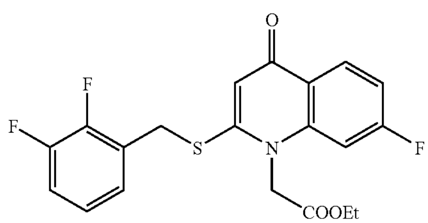 | Ethyl [2-(2,3-difluorobenzylthio)-7-fluoro-4-oxo-4H-quinolin-1-yl]acetate |
| D41 | Int. B102 | 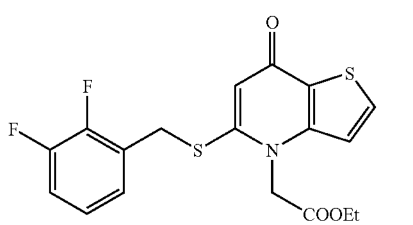 | Ethyl [5-(2,3-difluorobenzylthio)-7-oxo-7H-thieno[3,2-b]pyridin-4-yl]-acetate |
| D42 | Int. B103 | 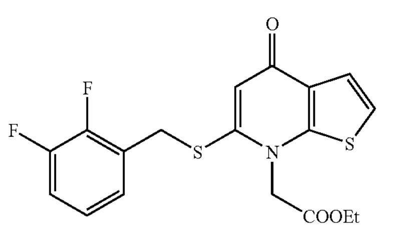 | Ethyl [5-(2,3-difluorobenzylthio)-7-oxo-7H-thieno[2,3-b]pyridin-4-yl]-acetate |
| D43 | Int. B104 | 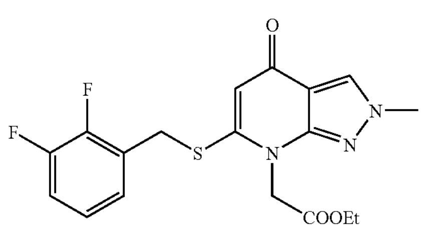 | Ethyl [6-(2,3-difluorobenzylthio)-2-methyl-4-oxo-2,4-dihydro-pyrazolo[3,4-b]pyridin-7-yl]acetate |

| No. | Precursor | Structure | Name |
|---|---|---|---|
| D44 | Int. B105 | 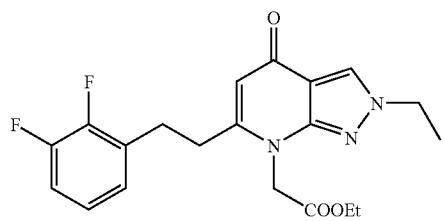 | Ethyl [2-(2,3-difluorobenzylthio)-4-oxo-4H-[1,8]naphthyridin-1-yl]acetate |

Intermediate D50—Ethyl [6-(2-(2,3-difluorophenyl)ethyl)-2-ethyl-4-oxo-2,4-dihydropyrazolo[3,4-b]pyridin-7-yl]acetate Intermediate E1—[2-(2,3-Difluorobenzylthio)-4-oxo-4H-quinolin-1-yl]acetic acid

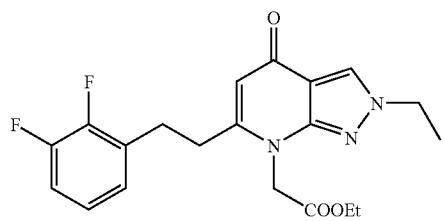

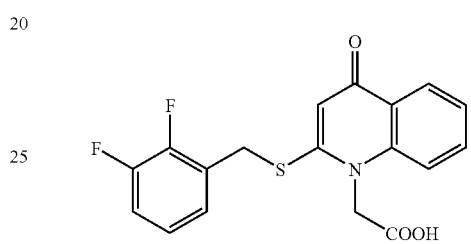

A mixture of Intermediate B92 (0.120 g, 1 equiv), potassium carbonate (0.070 g, 1.5 equiv) and iodoethane (1 equiv) in dry DMF (1.5 ml) was stirred at room temperature for 4 days. Ethyl acetate was added, the solution was washed with aq. sodium bicarbonate, then dried and evaporated. Chromatography (silica, 0–10% methanol in dichloromethane) gave the title compound as a brown solid (0.1 g, 77%). $^1$H-NMR (CDCl$_3$) δ 1.28 (3H, t), 1.54 (3H, t), 2.82 (2H, m), 3.02 (2H, m), 4.21–4.28 (4H, 2×q), 4.93 (2H, s), 5.96 (1H, s), 6.93–7.08 (3H, m), 8.01 (1H, s); MS (APCI+) found (M+1)=390. C$_{20}$H$_{21}$F$_2$N$_3$O$_3$ requires 389.

The following intermediate was prepared by the method of Intermediate 50:

(a) Trifluoroacetic acid (0.5 ml) was added to a solution of Int. D1 (0.193 g) in dichloromethane (5 ml) under argon, and stirred overnight at room temperature. Evaporation of the solvent and trituration with ether gave the title compound as a white solid (0.153 g).

(b) To a solution of Int. D25 (21.56 g, 0.055 mol) in dioxan (200 ml) was added sodium hydroxide (6.0 g, 0.15 mol) in water (200 ml) and the solution stirred for 2.5 h then concentrated. The residues were dissolved in water and acidified to pH 2 with 2M hydrochloric acid and the precipitate collected and washed sequentially with water, ether and then hexane. The solids were dried in vacuo at 40° C. to provide the title compound (20.0 g, 100%). $^1$H-NMR (d$_6$-DMSO) δ 4.5 (2H, s), 5.2 (2H, br s), 6.3 (1H, s), 7.18 (1H,

| No. | Precursor | Structure | Name |
|---|---|---|---|
| D51 | Int. B92, 2-iodo-propane | 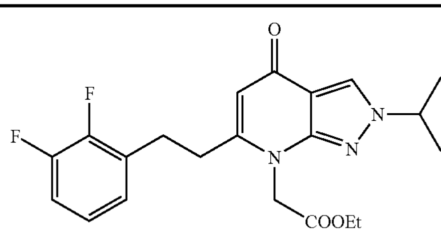 | Ethyl [6-(2-(2,3-difluorophenyl)ethyl)-2-isopropyl-4-oxo-2,4-dihydropyrazolo-[3,4-b]pyridin-7-yl]acetate |
| D52 | Int. B92, 1-bromo-2-methoxy-ethane | | Ethyl [6-(2-(2,3-difluorophenyl)ethyl)-2-(2-methoxyethyl)-4-oxo-2,4-dihydro-pyrazolo[3,4-b]pyridin-7-yl]acetate | m), 7.3 (1H, m), 7.4 (2H, m), 7.6 (1H, d, J=8.5 Hz), 7.7 (1H, t, J=8 Hz), 8.1 (1H, d, J=8 Hz). MS (APCI+) found (M+1)= 362. $C_{18}H_{13}F_2NO_3S$ requires 361.

The following intermediates were prepared by the method of Intermediate E1(a):

| No. | Precursor | Structure | Name |
| --- | --- | --- | --- |
| E2 | Int. D2 | 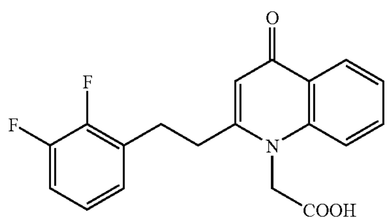 | [2-(2-(2,3-Difluorophenyl)ethyl)-4-oxo-4H-quinolin-1-yl]-acetic acid |
| E3 | Int. D3 | 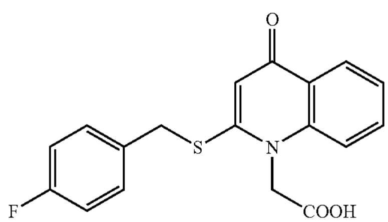 | [2-(4-Fluorobenzylthio)-4-oxo-4H-quinolin-1-yl]-acetic acid |
| E4 | Int. D20 | 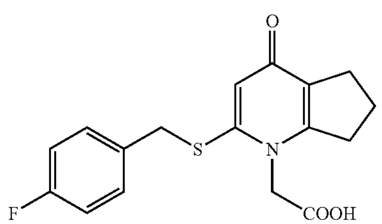 | [2-(4-Fluorobenzylthio)-4-oxo-4,5,6,7-tetrahydro-[1]pyridin-1-yl]-acetic acid |
| E5 | Int. D4 | 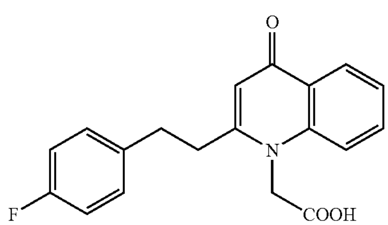 | [2-(2-(4-Fluorophenyl)ethyl)-4-oxo-4H-quinolin-1-yl]-acetic acid |
| E6 | Int. D5 | 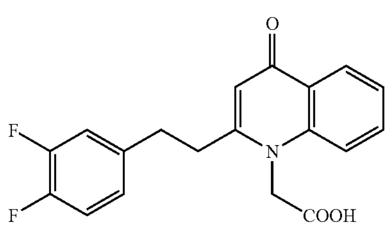 | [2-(2-(3,4-Difluorophenyl)ethyl)-4-oxo-4H-quinolin-1-yl]-acetic acid |
| E7 | Int. D6 | 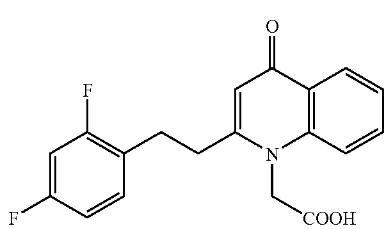 | [2-(2-(2,4-Difluorophenyl)ethyl)-4-oxo-4H-quinolin-1-yl]-acetic acid |

-continued

| No. | Precursor | Structure | Name |
|---|---|---|---|
| E8 | Int. D7 | 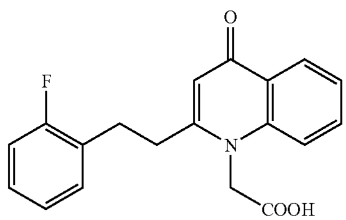 | [2-(2-(2-Fluorophenyl)ethyl)-4-oxo-4H-quinolin-1-yl]-acetic acid |
| E9 | Int. D8 | 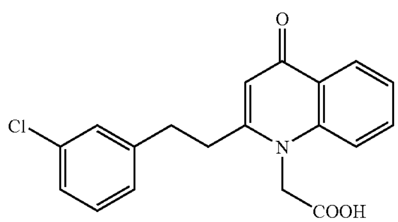 | [2-(2-(3-Chlorophenyl)ethyl)-4-oxo-4H-quinolin-1-yl]-acetic acid |
| E10 | Int. D9 | 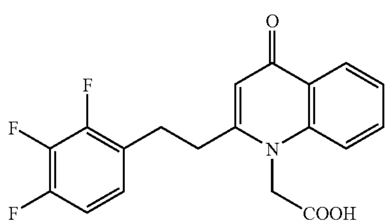 | [2-(2-(2,3,4-Trifluorophenyl)ethyl)-4-oxo-4H-quinolin-1-yl]-acetic acid |
| E11 | Int. D10 | 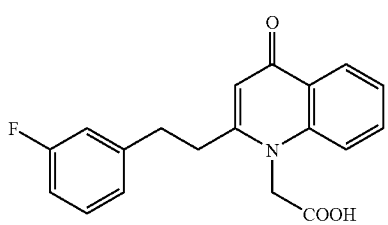 | [2-(2-(3-Fluorophenyl)ethyl)-4-oxo-4H-quinolin-1-yl]-acetic acid |
| E12 | Int. D13 | 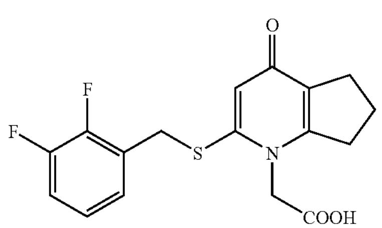 | [2-(2,3-difluorobenzylthio)-4-oxo-5,6-trimethylenepyridin-1-yl]acetic acid |
| E13 | Int. D11 | 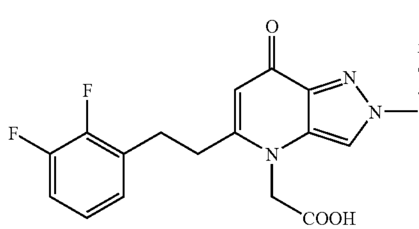 | [5-(2-(2,3-difluorophenyl)ethyl)-2-methyl-7-oxo-2,7-dihydropyrazolo[4,3-b]pyridin-4-yl]-acetic acid |

-continued

| No. | Precursor | Structure | Name |
|---|---|---|---|
| E14 | Int. D12 | 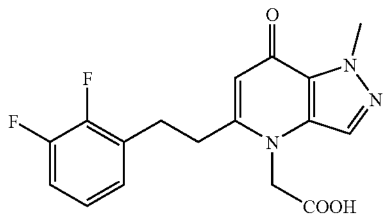 | [5-(2-(2,3-difluorophenyl)ethyl)-1-methyl-7-oxo-1,7-dihydropyrazolo[4,3-b]pyridin-4-yl]-acetic acid |

The following intermediates were prepared by the method of Intermediate E1(b):

| No. | Precursor | Structure | Name |
|---|---|---|---|
| E2 | Int. D14 | 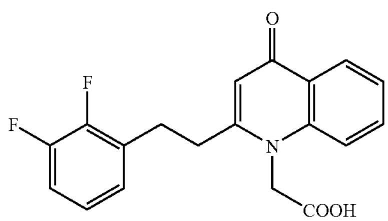 | (2-(2-(2,3-difluorophenyl)ethyl)-4-oxo-4H-quinolin-1-yl)acetic acid |
| E21 | Int. D26 | 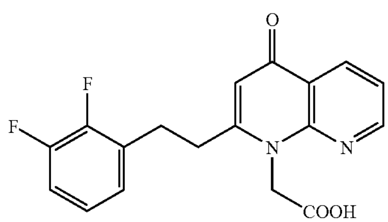 | (2-[2-(2,3-difluorophenyl)ethyl]-4-oxo-4H-[1,8]naphthyridin-1-yl)acetic acid |
| E22 | Int. D40 | 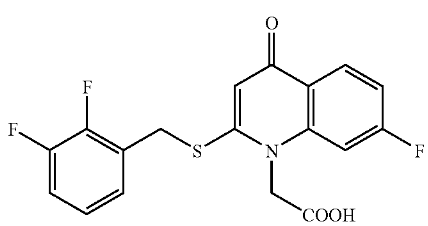 | [2-(2,3-difluorobenzylthio)-7-fluoro-4-oxo-4H-quinolin-1-yl]acetic acid |
| E23 | Int. D27 | 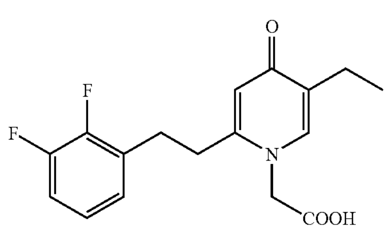 | [2-(2-(2,3-difluorophenyl)ethyl)-5-ethyl-4-oxo-4H-pyridin-1-yl]acetic acid |
| E24 | Int. D28 | 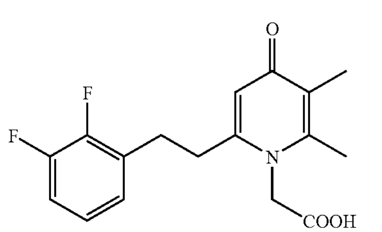 | [2-(2-(2,3-difluorophenyl)ethyl)-5,6-dimethyl-4-oxo-4H-pyridin-1-yl]acetic acid |

-continued

| No. | Precursor | Structure | Name |
|---|---|---|---|
| E25 | Int. D41 | 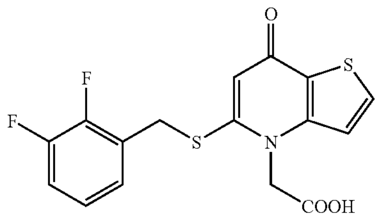 | [5-(2,3-difluorobenzylthio)-7-oxo-7H-thieno[3,2-b]pyridin-4-yl]acetic acid |
| E26 | Int. D29 | 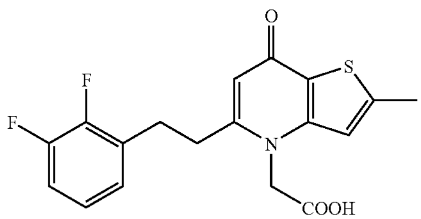 | 5-[2-(2-(2,3-difluorophenyl)ethyl)-2-methyl-7-oxo-7H-thieno[3,2-b]pyridin-4-yl]acetic acid |
| E27 | Int. D30 | 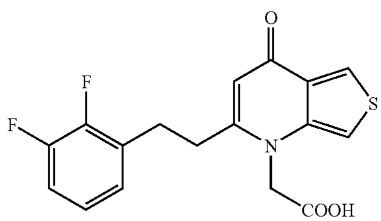 | [2-(2-(2,3-difluorophenyl)ethyl)-4-oxo-4H-thieno[3,4-b]pyridin-1-yl]-acetic acid |
| E28 | Int. D31 | 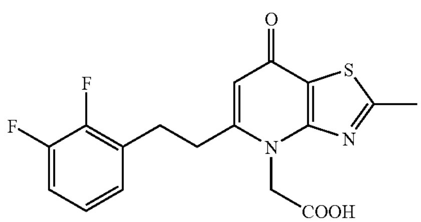 | [5-(2-(2,3-difluorophenyl)ethyl)-2-methyl-7-oxo-7H-thiazolo[4,5-b]-pyridin-4-yl]acetic acid |
| E29 | Int. D43 | 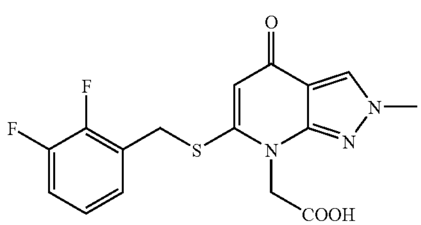 | [6-(2,3-difluorobenzylthio)-2-methyl-4-oxo-2,4-dihydropyrazolo[3,4-b]-pyridin-7-yl]acetic acid |
| E30 | Int. D32 | 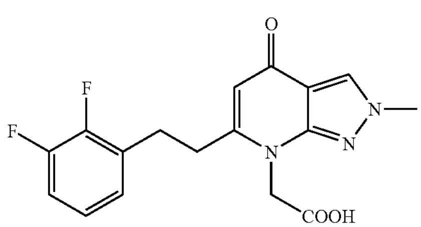 | [6-(2-(2,3-difluorophenyl)ethyl)-2-methyl-4-oxo-4H-pyrazolo[3,4-b]-pyridin-7-yl]acetic acid |
| E31 | Int. D50 | 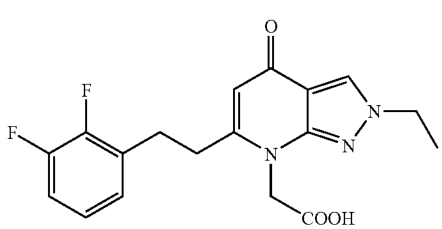 | [6-(2-(2,3-difluorophenyl)ethyl)-2-ethyl-4-oxo-2,4-dihydropyrazolo[3,4-b]pyridin-7-yl]-acetic acid |

| No. | Precursor | Structure | Name |
|---|---|---|---|
| E32 | Int. D51 | 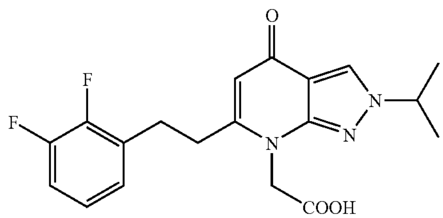 | [6-(2-(2,3-difluorophenyl)ethyl)-2-isopropyl-4-oxo-2,4-dihydropyrazolo-[3,4-b]pyridin-7-yl]acetic acid |
| E33 | Int. D15 | 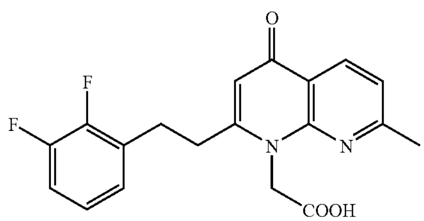 | [2-(2-(2,3-difluorophenyl)ethyl)-7-methyl-4-oxo-4H-[1,8]naphthyridin-1-yl]acetic acid |
| E34 | Int. D44 | 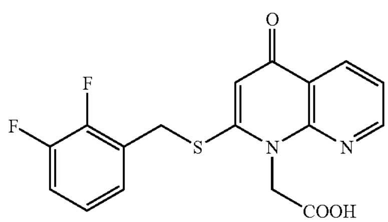 | [2-(2,3-difluorobenzylthio)-4-oxo-4H-[1,8]naphthyridin-1-yl]acetic acid |
| E35 | Int. D42 | 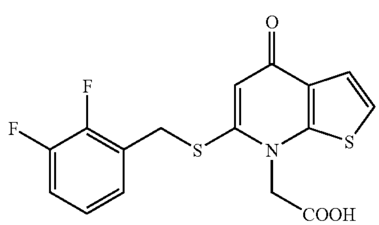 | [5-(2,3-difluorobenzylthio)-7-oxo-7H-thieno[2,3-b]pyridin-4-yl]acetic acid |
| E36 | Int. D33 | 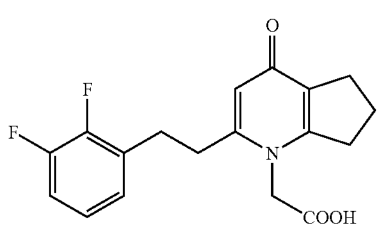 | [2-(2-(2,3-difluorophenyl)ethyl)-4-oxo-5,6-trimethylenepyridin-1-yl]-acetic acid |
| E37 | Int. D34 | 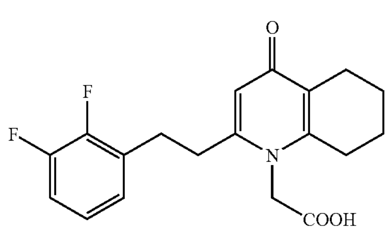 | [2-(2-(2,3-difluorophenyl)ethyl)-4-oxo-5,6-tetramethylenepyridin-1-yl]-acetic acid |

| No. | Precursor | Structure | Name |
|---|---|---|---|
| E38 | Int. D52 | 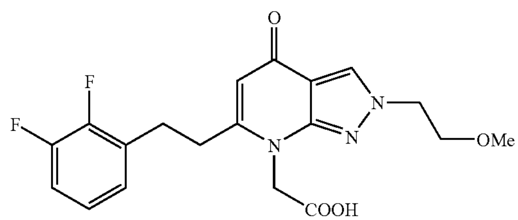 | [6-(2-(2,3-difluorophenyl)ethyl)-2-(2-methoxyethyl)-4-oxo-2,4-dihydropyrazolo[3,4-b]pyridin-7-yl]acetic acid |

Example 1

N-(2-Diethylaminoethyl)-2-[2-(2,3-difluorobenzylthio)-4-oxo-4H-quinolin-1-yl]-N-(4'-trifluoromethylbiphenyl-4-ylmethyl)acetamide bitartrate

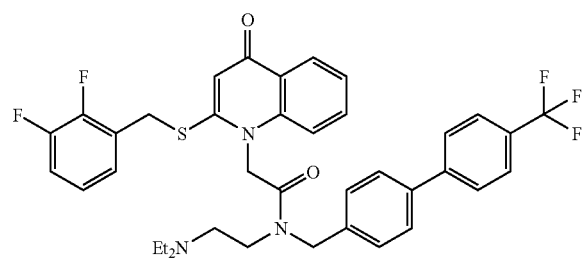

A mixture of 2-(2-(2,3-difluorobenzylthio)-4-oxo-4H-quinolin-1-yl)acetic acid (Int. E1) (0.15 g, 1 equiv), N,N-diethyl-N'-(4'-trifluoromethylbiphenyl-4-ylmethyl)ethane-1,2-diamine (Int. A2) (0.145 g, 1 equiv), O-(7-azabenzotriazol-1-yl)-N,N,N',N'-tetramethyluronium hexafluorophosphate (HATU) (0.154 g, 1.2 equiv) and diisopropylamine (0.174 ml, 2.4 equiv) in dichloromethane (10 ml) was stirred at room temperature overnight, then washed with aqueous ammonium chloride and aqueous sodium bicarbonate. The organic layer was dried and evaporated, and the product purified by column chromatography (silica, 4% [2M ammonia in methanol] in dichloromethane). Product fractions were evaporated to an off-white foam (0.201 g). This free base (0.201 g) was dissolved in methanol (10 ml), tartaric acid (0.044 g) was added, the mixture stirred for 5 min then evaporated. Trituration with ether gave the bitartrate salt as an off-white solid (0.209 g). $^1$H-NMR (d$_6$-DMSO, ca 2:1 rotamer mixture) δ 1.03 (6H, m), 2.59 (6H, m), 3.41–3.62 (2H, m), 4.26 (2H, 2×s), 4.65–4.83 (2H, m), 5.12–5.56 (2H, m), 6.44 (1H, 2×s), 6.93–7.12 (3H, m), 7.30–7.75 (11H, m), 8.41 (1H, 2×d); MS (APCI+) found (M+1)=694. $C_{38}H_{36}F_5N_3O_2S$ requires 693.

Example 2

N-(2-Diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide

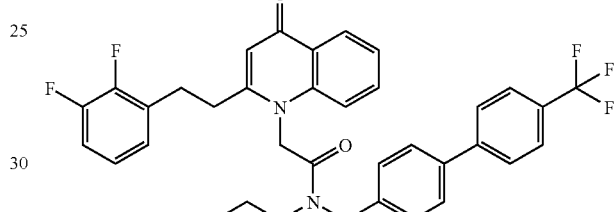

A mixture of 2-[2-(2-(2,3-difluorophenyl)ethyl)-4-oxo-4H-quinolin-1-yl]-acetic acid (Int. E2) (0.26 g, 1 equiv), N,N-diethyl-N'-(4'-trifluoromethylbiphenyl-4-ylmethyl)ethane-1,2-diamine (Int. A2) (0.265 g, 1 equiv), HATU (0.28 g, 1.2 equiv) and diisopropylamine (0.32 ml, 2.4 equiv) in dichloromethane (15 ml) was stirred at room temperature overnight, then washed with aqueous ammonium chloride and aqueous sodium bicarbonate. The organic layer was dried and evaporated, and the product purified by column chromatography (silica, 2% [2M ammonia in methanol] in dichloromethane). Product fractions were evaporated to an off-white foam (0.201 g). Trituration with ether gave the title compound as a white solid (0.476 g). $^1$H-NMR (d$_6$-DMSO, ca 2:1 rotamer mixture) δ 0.93 (6H, 2×t), 2.38–2.80 (4H, m), 2.90–3.05 (4H, m), 3.45 (2H, m), 4.30–4.95 (4H, m), 5.23–5.58 (2H, m), 6.06 (1H, 2×s), 7.14–7.38 (7H, m), 7.50–7.95 (7H, m), 8.16 (1H, m); MS (APCI+) found (M+1)=676. $C_{39}H_{38}F_5N_3O_2$ requires 675.

Example 3

N-(2-Diethylaminoethyl)-2-[2-(2-(2,3-difluorophenyl)ethyl-4-oxo-4H-quinolin-1-yl]-N-(4'-trifluoromethylbiphenyl-4-ylmethyl)acetamide bitartrate Treatment of N-(2-Diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide (Ex 2) with d-tartaric acid as for Example 1 gave the title compound as the bitartrate salt.

Example 4

N-(2-Diethylaminoethyl)-2-[2-(2,3-difluorobenzylthio)-4-oxo-5,6-trimethylenepyridin-1-yl]-N-(4'-trifluoromethylbiphenyl-4-ylmethyl)acetamide bitartrate

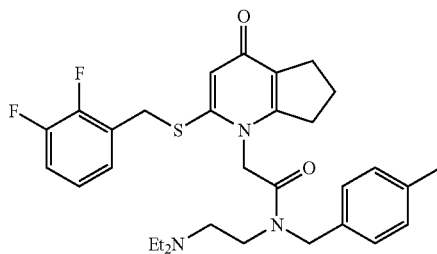

The free base was prepared from Int. E12 and Int. A2 by the method of Example 1. The bitartrate was formed as in example 1. $^1$H NMR (d$_6$-DMSO) δ 0.93, 0.99 (6H, 2×t), 1.95 (2H, m), 2.57–2.88 (8H, m), 3.21–3.60 (4H, m), 4.21 (2H, s), 4.23, 4.29 (2H, 2×s), 4.64, 4.75 (2H, 2×s), 5.01, 5.22 (2H, 2×s), 6.15, 6.17 (1H, 2×s), 7.12–7.21 (2H, m), 7.34–7.45 (3H, m), 7.67 (1H, d), 7.71 (1H, d), 7.85 (4H, m); MS (APCI) found (M+1)=684. $C_{37}H_{38}F_5N_3O_2S$ requires 683.

Example 5

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide

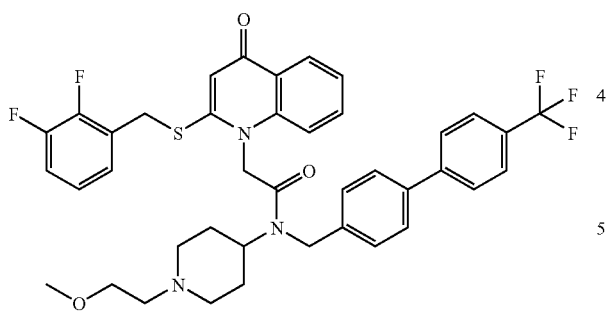

The free base was prepared from Int. E1 and Int. A42 by the method of Example 1, except using DMF as solvent in place of dichloromethane. 1.97 g of this material was crystallised from n.butyl acetate (10 ml) to give the title compound (1.35 g). $^1$H-NMR (CD$_3$OD) δ 1.7–2.05 (4H, m), 2.05–2.3 (2H, 2×t), 2.5–2.65 (2H, m), 2.95–3.1 (2H, m), 3.3 (3H, s), 3.45–3.55 (2H, m), 3.9–4.05+4.4–4.5 (1H, 2×m), 4.37+4.48 (2H, 2×s), 4.71+4.87 (2H, 2×br s), 5.31+5.68 (2H, 2×s), 6.44+6.52 (1H, 2×s), 6.95–7.3 (3H, m), 7.35–7.85 (11H, m), 8.2–8.35 (1H, m); MS (APCI+) found (M+1) 736. $C_{40}H_{38}F_5N_3O_3S$ requires 735.

Example 6

N-(1-Methylpiperdin-4-yl)-2-[2-(2,3-difluorobenzylthio)-4-oxo-4H-quinolin-1-yl]-N-(4'-trifluoromethylbiphenyl-4-ylmethyl)acetamide bitartrate

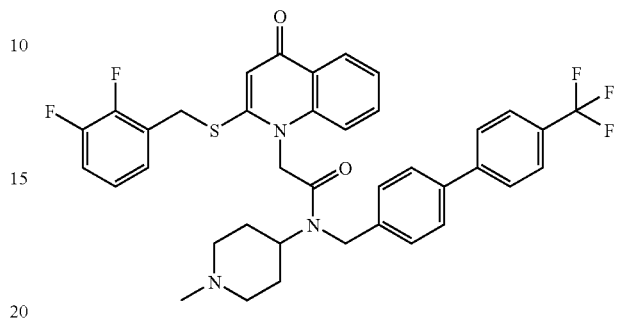

The free base was prepared from Int. E1 and Int. A5 by the method of Example 1, except using DMF as solvent in place of dichloromethane. Chromatography (acetone to acetone/MeOH 4:1) yielded the free base (~7:3 rotomer mixture); $^1$H-NMR (CDCl$_3$) δ 1.7–1.8 (3.7H, m), 1.9–2.15 (2.3H, m), 2.26 (2.1H, s), 2.3 (0.9H, s), 2.9 (1.4H, d, J=11.5 Hz), 2.98 (0.6H, d, J=10 Hz), 3.7 (0.3H, m), 4.2 (1.4H, s), 4.27 (0.6H, s), 4.62 (0.7H, m), 4.69 (0.6H, s), 4.73 (1.4H, s), 5.01 (1.4H, br s), 5.35 (0.6H, br s), 6.41 (0.7H, s), 6.49 (0.3H, s), 6.9–7.2 (4H, m), 7.29–7.75 (10H, m), 8.38 (0.7H, d, J=8 Hz), 8.4 (0.3H, d, J=8 Hz); MS (APCI+) found (M+1)=692. $C_{38}H_{34}F_5N_3O_2S$ requires 691 Conversion to bitartrate salt was carried out as in Example 1.

Example 7

N-(1-Methylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate

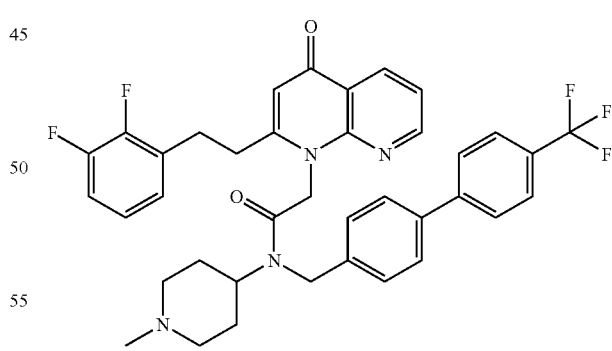

To a stirring mixture of intermediate A5 (12.53 g, 1 equiv) and diisopropylethylamine (18.82 ml, 3 equiv) in dry THF (125 ml) under an argon atmosphere was added in one portion O-(7-azabenzotriazol-1-yl)-N,N,N',N'-tetramethyluronium hexafluorophosphate (HATU) (16.65 g, 1.5 equiv). A solution of Int. E21 (12.4 g, 1 equiv), in dry N-methylpyrrolidone (25 ml) and dry THF (100 ml) was then added dropwise over 1.5 h. After 72 h the solvents were evaporated under reduced pressure and the residue treated with aqueous sodium bicarbonate and extracted 3 times with ethyl acetate. The combined extracts were washed with aqueous sodium bicarbonate, aqueous ammonium chloride then aqueous sodium bicarbonate, dried (Na$_2$SO$_4$) and evaporated. The residue was chromatographed (fine silica, 2M ammonia in methanol/dichloromethane) and the product obtained dissolved in dichloromethane and washed twice with 0.5M aqueous sodium hydroxide then brine, dried (Na$_2$SO$_4$) and the solvent evaporated. Crystallisation then recrystallisation from acetonitrile gave the free base, 10.75 g. This material (10.69 g, 1 equiv) together with L-tartaric acid (2.39 g, 1 equiv) was dissolved in methanol (50 ml) and evaporated to a thick syrup which was triturated with ether to give the bitartrate salt as an off-white solid (12.4 g). $^1$H NMR (d$_6$-DMSO), δ 1.58–1.66 and 1.80–2.05 (4H, m), 2.40–2.65 (5H, m), 2.93–3.19 (6H, m), 4.15 (2H, s), 4.16–4.38 (1H, m), 4.62, 4.88, 5.42, 5.68 (4H, 4×s), 6.00, 6.03 (1H, 2×s), 7.10–7.97 (12H, m), 8.48 (1H, m), 8.82–8.90 (1H, m); MS (APCI+) found (M+1)=675; C$_{38}$H$_{35}$F$_5$N$_4$O$_2$ requires 674.

Example 8

N-(1-(2-Methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide

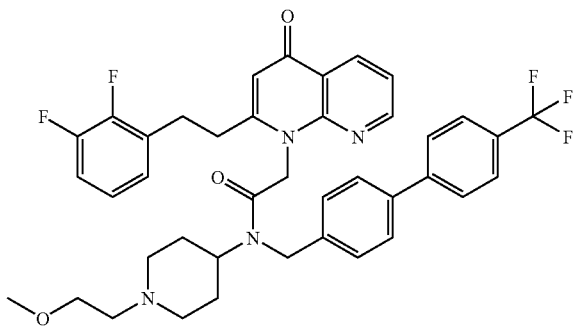

To a stirring mixture of Int. A42 (14.12 g, 1 equiv) and diisopropylethylamine (18.82 ml, 3 equiv) in dry THF (125 ml) under an argon atmosphere was added in one portion O-(7-azabenzotriazol-1-yl)-N,N,N',N'-tetramethyluronium hexafluorophosphate (HATU) (16.65 g, 1.5 equiv). A solution of Int. E21 (12.4 g, 1 equiv), in dry N-methylpyrrolidone (25 ml) and dry THF (100 ml) was then added dropwise over 1.5 h. After 16 h the solvents were evaporated under reduced pressure and the residue treated with 1M hydrochloric acid (200 ml) and extracted 3 times with ethyl acetate. The combined extracts were washed with 1M hydrochloric acid (200 ml), brine, 2M sodium hydroxide ×2, dried (Na$_2$SO$_4$) and evaporated. The residue was chromatographed (fine silica, 2M ammonia in methanol/dichloromethane) and the oil obtained dissolved in ether and allowed to crystallise then recrystallised from dichloromethane/ether, yield 11.98 g (free base). 13.64 g of title compound formed in the same manner as above was recrystallised from hot n.butyl acetate (70 ml) to give crystalline title compound (11.5 g). $^1$H NMR (CD$_3$OD), δ 1.6–2.35 (6H, m), 2.45–2.65 (2H, 2×m), 2.9–3.12 (4H, m), 3.12–3.35 (5H), 3.4–3.55 (2H, 2×t), 4.17+4.40 (1H, 2×m), 4.71+4.93 (2H, s), 5.3–6.0 (2H, br), 6.26+6.31 (1H, 2×s), 7.0–7.35 (3H, m), 7.3–7.4 (1H, d), 7.45–7.6 (2H, m), 7.6–7.9 (6H, m), 8.61 (1H, br t), 8.87 (1H, m); MS (APCI+) found (M+1)=719. C$_{40}$H$_{39}$F$_5$N$_4$O$_3$ requires 718.

Example 9

N-(1-(2-Methoxyethyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate

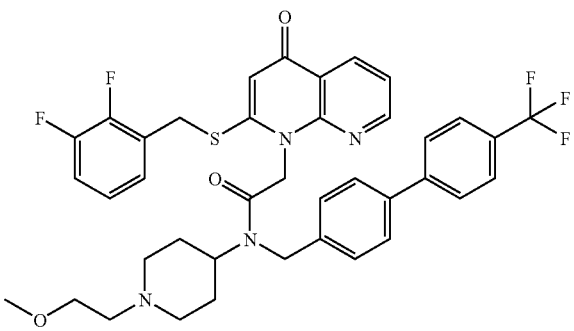

The free base was prepared from Int. E34 and Int. A42 by the method of Example 7. Chromatography (EtOAc/acetone/MeOH 9:1) yielded the free base. $^1$H-NMR (d$_6$-DMSO) (~1:1 rotomer mixture): δ 1.55 (1H, br d, 11 Hz), 1.75–1.9 (4H, m), 2.15 (0.5H, t, J=8 Hz), 2.3 (1H, br t, J=12 Hz), 2.4 (1H, br t, J=11 Hz), 2.66 (2H, m), 3.06 (2H, br t, 12 Hz), 3.2 (1.5H, s), 3.25 (1.5H, s), 3.3 (0.5H, t, J=7 Hz), 3.45 (2H, m), 4.1 (0.5H, m), 4.2 (2H, s), 4.25 (0.5H, m), 4.5 (1H, s), 4.59 (2H, br s), 4.8 (1H, s), 5.45 (1H, br), 5.75 (1H, br), 6.35 (0.5H, s), 6.38 (0.5H, s), 7.16 (1H, m), 7.2–7.4 (4H, m), 7.6 (2H, d, J=8 Hz), 7.7 (5H, m), 8.5 (1H, m), 8.7 (2H, br), 8.82 (1H, m); MS (APCI+) found (M+1)=737. C$_{39}$H$_{37}$F$_5$N$_4$O$_3$S requires 736.

Example 10

N-(1-Ethylpiperidin-4-yl)-2-[2-(2,3-difluorobenzylthio)-4-oxo-4H-quinolin-1-yl]-N-(4'-ethylbiphenyl-4-ylmethyl)acetamide bitartrate

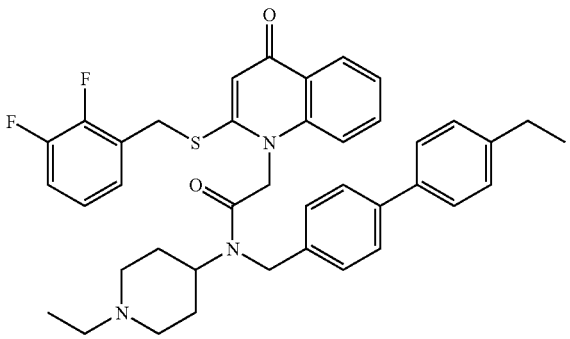

The free base was prepared from Int. E1 and lift A29 by the method of Example 1, except using DMF as solvent in place of dichloromethane. The bitartrate salt was formed as in example 1. $^1$H NMR (d$_6$-DMSO) δ 1.07 (3H, t), 1.22 (3H, t), 1.70–1.91 (4H, m), 2.37 (2H, m), 2.66 (4H, m), 3.20 (2H, m), 4.12 (2H, s), 4.44 (3H, m), 4.70 (2H, m), 5.34 (2H, m), 6.27, 6.33 (1H, 2×s), 7.11–7.76 (14H, m), 8.14 (1H, m); MS (APCI+) found (M+1)=666. C$_{40}$H$_{41}$F$_2$N$_3$O$_2$S requires 665.

Example 11

N-(1-Ethylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate

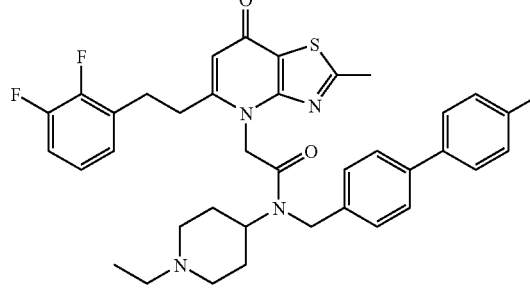

Prepared from intermediate E28 (0.15 g) and intermediate A40 (0.149 g) using HATU (0.188 g) and diisopropylamine (0.172 ml) followed by bitartrate salt formation as in example 1. $^1$H-NMR (d$_6$-DMSO) δ 0.95–1.15 (3H, m), 1.6–2.1 (4H, m), 2.84 (3H, 2×s), 2.3–3.25 (10H, m), 4.14 (2H, s), 4.05–4.4 (1H, 2×m), 4.62+4.83 (2H, 2×br s), 5.37+5.62 (2H, 2×br s), 6.02+6.05 (1H 2×s), 7.05–7.4 (4H, m), 7.5–7.7 (2H, m), 7.7–8.0 (5H, m); MS (APCI+) found (M+1)=709. $C_{38}H_{37}F_5N_4O_2S$ requires 708.

Example 12

(±)N-(1-Ethylpyrrolidin-3-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate

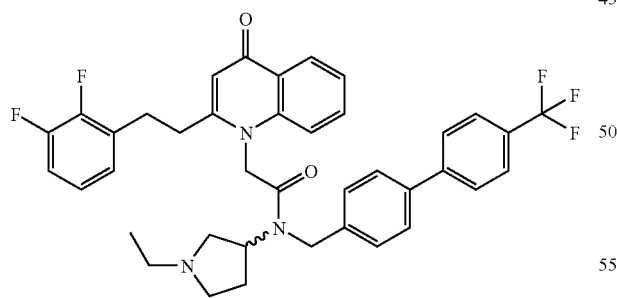

Prepared from intermediate E2 (0.295 g) and A23 (0.30 g) using HATU (0.395 g) and diisopropylamine (0.3 ml) followed by bitartrate salt formation as in example 1. Spectral details of the free base are quoted below. $^1$H-NMR (CDCl$_3$) δ 1.0–1.2 (3H, m), 1.8–2.15 (1H, m), 2.15–3.15 (11H, m), 4.6–5.2 (5H, m), 6.14+6.24 (1H, 2×s), 6.8–7.8 (14H, m), 8.25–8.45 (1H, m); MS (APCI+) found (M+1)=6.74. $C_{39}H_{36}F_5N_3O_2$ requires 673.

Example 13

(±)N-(1-Ethylpyrrolidin-3-yl)-2-[2-(2,3-difluorobenzylthio)-4-oxo-4H-quinolin-1-yl]-N-(4'-trifluoromethylbiphenyl-4-ylmethyl)acetamide bitartrate

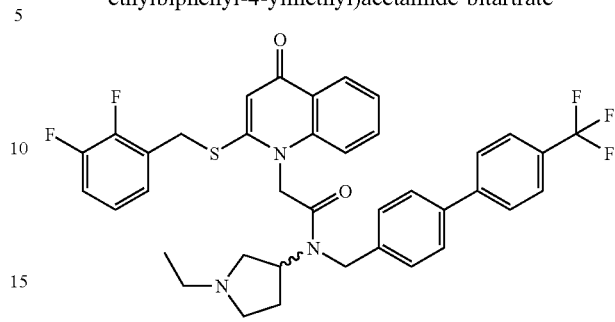

Prepared from intermediate E1 (0.312 g) and A23 (0.30 g) using HATU (0.395 g) and diisopropylamine (0.3 ml) followed by bitartrate salt formation as in example 1. Spectral details of the free base are quoted below. $^1$H-NMR (CDCl$_3$) δ 0.95–1.35 (3H, m), 1.8–2.8 (6H, m), 2.8–3.1 (2H, m), 4.19+4.25 (2H, 2×s), 4.5–5.5 (5H, m), 6.36+6.43 (1H, 2×s), 6.85–7.2 (4H, m), 7.2–7.85 (10H, m), 8.25–8.5 (1H, m).

Example 14

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide bitartrate

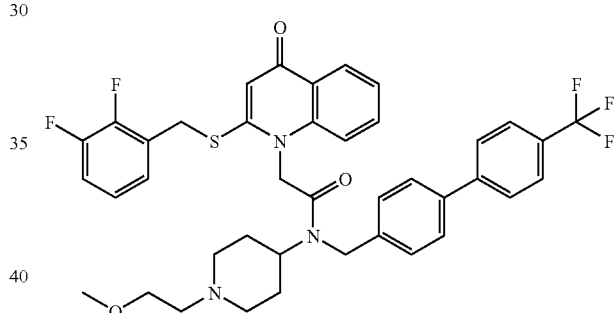

·C$_4$H$_6$O$_6$

Example 5 was converted to the bitartrate by the method of example 1.

Example 15

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide dihydrochloride

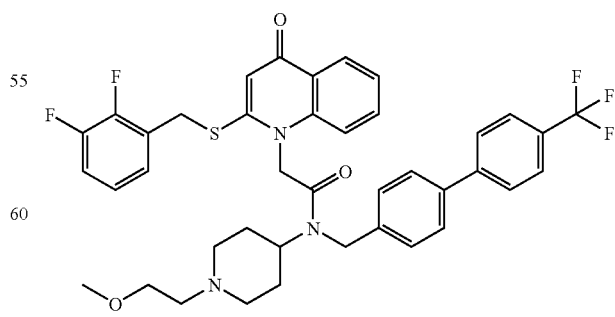

·2HCl

Example 5 (1.0 g) was dissolved in isopropanol (10 ml) and 1M HCl in diethyl ether (4 ml) added. A thick precipitate formed. The mixture was evaporated under reduced pressure and the residue dissolved in isopropanol (10 ml) with heating. On cooling a thick precipitate formed that was filtered and dried. 0.2 g of this material was recrystallised from further isopropanol (10 ml) to give the title compound (0.132 g). $^1$H-NMR (CD$_3$OD) δ 1.9–2.6 (4H, m), 3.0–3.5 (4H, m), 3.36+3.41 (3H, 2×s), 3.5–3.8 (4H, m), 7.0–7.5 (4H, m), 7.5–7.65 (3H, m), 7.65–7.85 (5H, m), 7.9–8.2 (2H, m), 8.4–8.55 (1H, m).

Example 16

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide mono paratoluenesulphonate

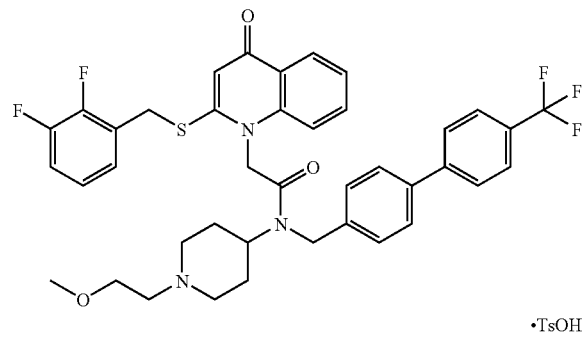

·TsOH

To a solution of example 5 (1.0 g) in tetrahydrofuran (THF) (10 ml) was added a solution of paratoluenesulphonic acid monohydrate (1 equiv) in THF (5 ml) and the mixture stirred at 0° C. After 18 h, further THF was added and the mixture filtered and dried to give a solid (0.87 g). 0.7 g of this material was dissolved in THF (9 ml) and left at 0° C. for 18 h. The solid formed was filtered and washed with further THF (2 ml) and dried to give the title compound as a crystalline salt (0.67 g). $^1$H-NMR (CD$_3$OD) δ 1.9–2.4 (4H, m), 2.31 (3H, s), 3.0–3.45 (7H, m's), 3.5–3.75 (4H, m), 4.3–4.55 (3H, m), 4.6–5.0 (2H, m), 5.40+5.73 (2H, 2×s), 6.47 (1H, s), 6.95–7.3 (5H, m), 7.3–7.85 (13H, m) 8.2–8.35 (1H, m).

Example 17

N-(1-(2-Methoxyethyl)piperidin-4-yl)-2-[2-(2-(2,3-difluorophenyl)ethyl)-4-oxo-4H[1,8]naphthyridin-1-yl]-N-(4'-trifluoromethylbiphenyl-4-ylmethyl)acetamide bitartrate

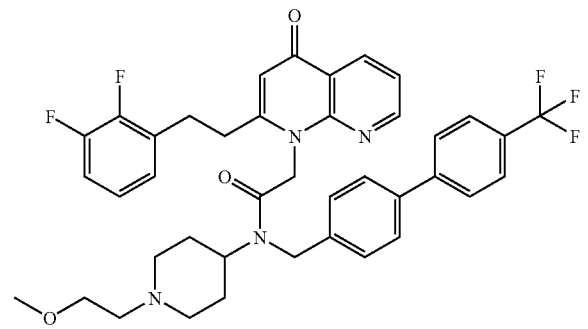

Example 8 (8 g, 1 equiv) together with L-tartaric acid (1.67 g, 1 equiv) was dissolved in methanol (50 ml) and evaporated to a thick syrup which was triturated with ether to give the bitartrate salt as an off-white solid (9.54 g). $^1$H NMR (CD$_3$OD), δ 1.53–1.64 and 1.70–1.87 (4H, m), 2.15–2.43 and 2.55–2.69 (4H, m), 2.93–3.50 (11H, m), 4.05–4.32 (1H, m), 4.19 (2H, s), 4.61, 4.87, 5.42, 5.67 (4H, 4×s), 6.08, 6.11 (1H, 2×s), 7.09–7.94 (12H, m), 8.49 (1H, m), 8.82–8.90 (1H, m); MS (APCI+) found (M+1)=719. C$_{40}$H$_{39}$F$_5$N$_4$O$_3$ requires 718.

Example 18

N-(1-(2-Methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl) acetamide monohydrochloride

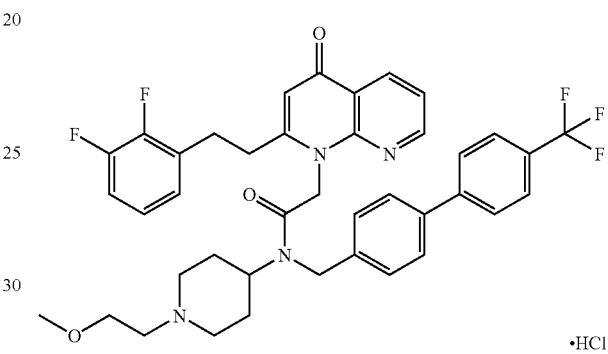

·HCl

Example 8 (0.5 g) in methylethylketone (4 ml) was mixed with 4M HCl in dioxane (0.174 ml). After 18 h at 0° C., a small amount of solid was filtered off. The mother liquors were evaporated under reduced pressure and the residue crystallised from acetone (4 ml). The solid so formed was recrystallised from acetone to give the title compound (0.336 g). $^1$H NMR (CD$_3$OD), δ 1.85–2.5 (4H, m), 2.95–3.15 (4H, br), 3.15–3.5 (7H, ss+m), 3.8 (4H, m), 4.38+4.61 (1H, br m), 4.74+4.97 (2H, 2×s), 5.4–6.0 (2H, br), 6.29 (1H, s), 7.0–7.25 (3H, m), 7.3–7.65 (2H, m), 7.65–7.9 (7H, m), 8.6–8.7 (1H, m), 8.8–8.9 (1H, m).

Example 19

N-(1-(2-Methoxyethyl)piperidin-4-yl)-2-[2-(2-(2,3difluorophenyl)ethyl)-4-oxo-4H-[1,8]naphthyridin-1-yl]-N-(4'-trifluoromethylbiphenyl-4-ylmethyl) acetamide dihydrochloride

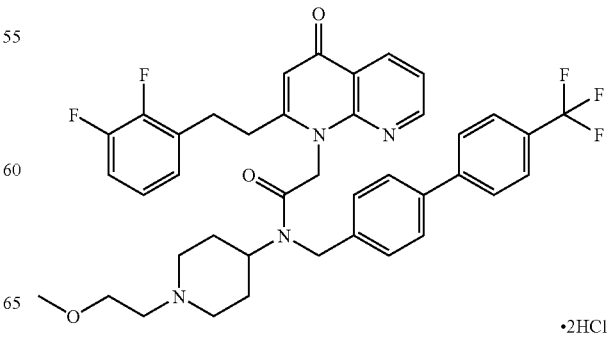

·2HCl

Example 8 (0.321 g) in ethanol (3 ml) was stirred overnight with 4M HCl in dioxan (0.25 ml). The solid was collected by filtration, washed with ethanol and dried to give the title compound (0.31 g). $^1$H NMR (CD$_3$OD), δ 1.8–2.55 (4H, m), 3.0–3.8 (15H, m), 4.15–5.1 (3H, m), 5.6–6.6 (2H, br), 6.94+6.97 (1H, 2×s), 7.0–7.25 (3H, m), 7.3–7.95 (9H, m), 8.8–8.95 (1H, m), 9.15–9.25 (1H, m).

The following Examples were made by the general method of Example 1, using an appropriate solvent such as dimethylformamide or dichloromethane:

| Ex. No. | Precursors | Structure | Name |
|---------|------------|-----------|------|
| 20 | Int. E3<br>Int. A2 | 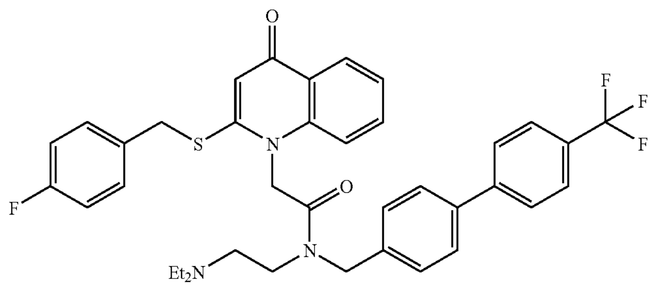 | N-(2-Diethylaminoethyl)-2-[2-(4-fluorobenzylthio)-4-oxo-4H-quinolin-1-yl]-N-(4'-trifluoromethylbiphenyl-4-ylmethyl)-acetamide bitartrate |
| 21 | Int. E4<br>Int. A2 | 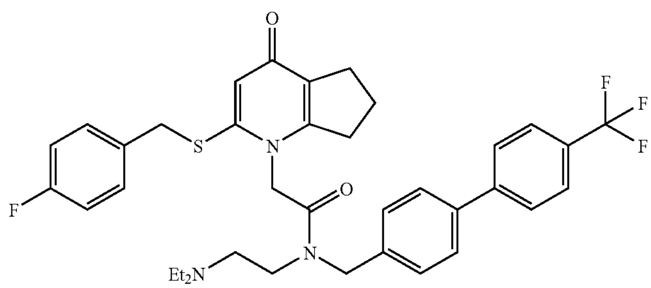 | N-(2-Diethylaminoethyl)-2-[2-(4-fluorobenzylthio)-4-oxo-5,6-trimethylenepyridin-1-yl]-N-(4'-trifluoromethyl-biphenyl-4-ylmethyl)acetamide bitartrate |
| 22 | Int. E12<br>Int. A2 | 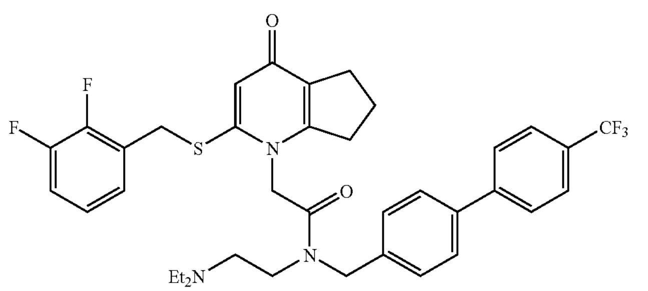 | N-(2-Diethylaminoethyl)-2-[2-(2,3-difluorobenzylthio)-4-oxo-5,6-trimethylenepyridin-1-yl]-N-(4'-trifluoromethyl-biphenyl-4-ylmethyl)acetamide bitartrate |
| 23 | Int. E5<br>Int. A2 | 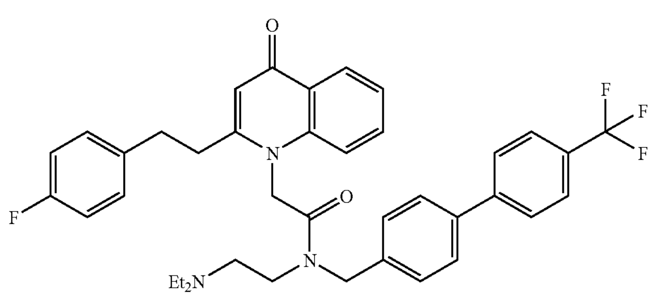 | N-(2-Diethylaminoethyl)2-[2-(4-fluorophenyl)ethyl)-4-oxo-4H-quinolin-1-yl]-N-(4'-trifluoromethylbiphenyl-4-ylmethyl)-acetamide |

-continued

| Ex. No. | Precursors | Structure | Name |
|---|---|---|---|
| 24 | Int. E6<br>Int. A2 | 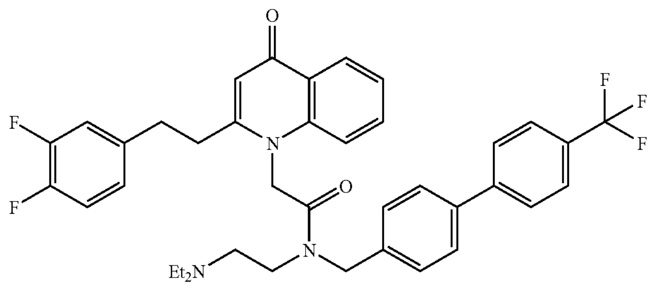 | N-(2-Diethylaminoethyl)2-[2-(2-(3,4-difluorophenyl)ethyl)-4-oxo-4H-quinolin-1-yl]-N-(4'-trifluoro-methylbiphenyl-4-ylmethyl)-acetamide bitartrate |
| 25 | Int. E8<br>Int. A2 | 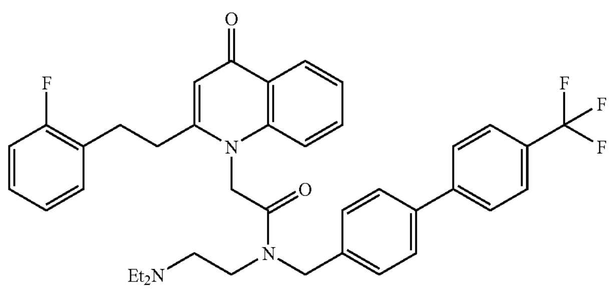 | N-(2-Diethylaminoethyl)-2-[2-(2-(2-fluorophenyl)ethyl)-4-oxo-4H-quinolin-1-yl]-N-(4'-trifluoro-methylbiphenyl-4-ylmethyl)-acetamide bitartrate |
| 26 | Int. E9<br>Int. A2 | 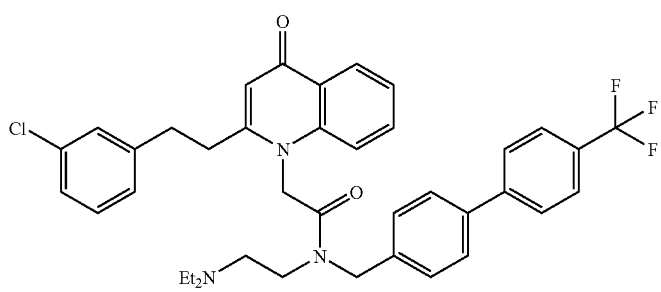 | N-(2-Diethylaminoethyl)-2-[2-(2-(3-chlorophenyl)ethyl)-4-oxo-4H-quinolin-1-yl]-N-(4'-trifluoro-methylbiphenyl-4-ylmethyl)-acetamide bitartrate |
| 27 | Int. E21<br>Int. A2 | 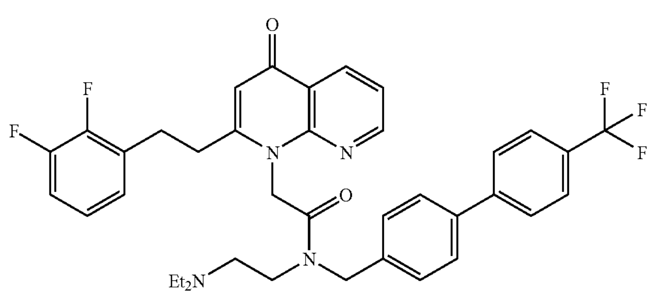 | N-(2-Diethylaminoethyl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide bitartrate |
| 28 | Int. E21<br>Int. A40 | 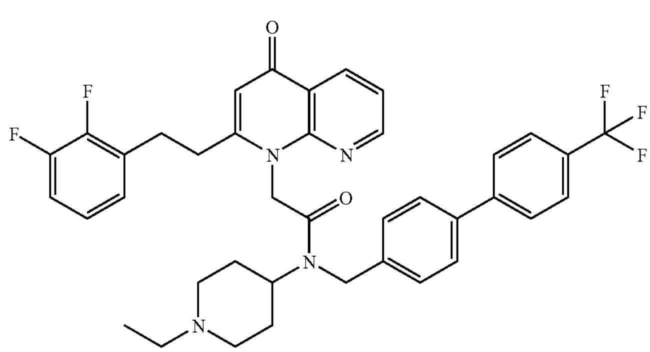 | N-(1-Ethylpiperidin-4-yl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide |

| Ex. No. | Precursors | Structure | Name |
|---|---|---|---|
| 29 | Int. E2<br>Int. A40 | 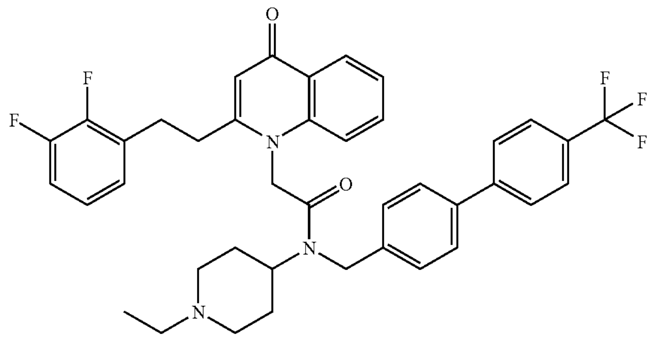 | N-(1-Ethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |
| 30 | Int. E2<br>Int. A22 | 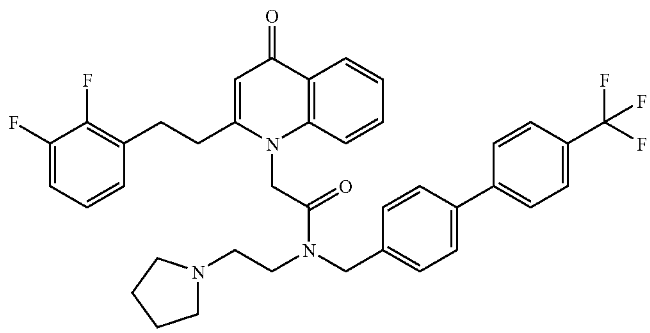 | N-(2-Pyrrolidin-1-ylethyl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |
| 31 | Int. E2<br>Int. A41 | 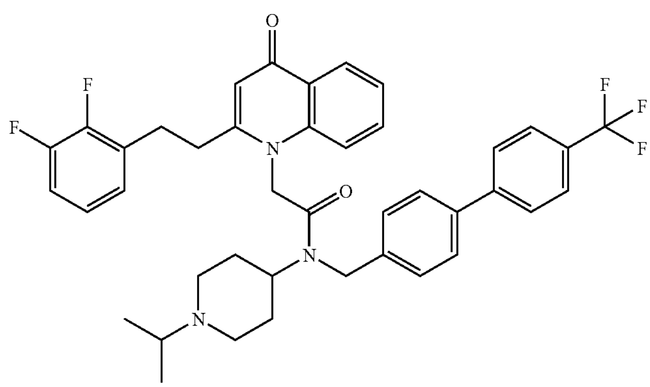 | N-(1-Isopropylpiperidin-4-yl)-2-[2-(2-(2,3-difluorophenyl)ethyl)-4-oxo-4H-quinolin-1-yl]-N-4'-trifluoromethylbiphenyl-4-ylmethyl)acetamide bitartrate |
| 32 | Int. E2<br>Int. A20 | 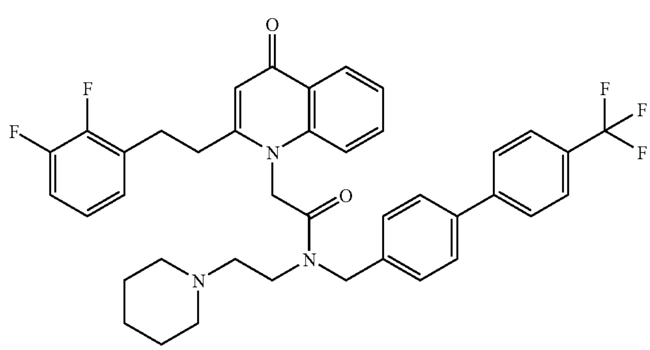 | N-(2-piperidin-1-ylethyl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |

| Ex. No. | Precursors | Structure | Name |
|---|---|---|---|
| 33 | Int. E22<br>Int. A2 | 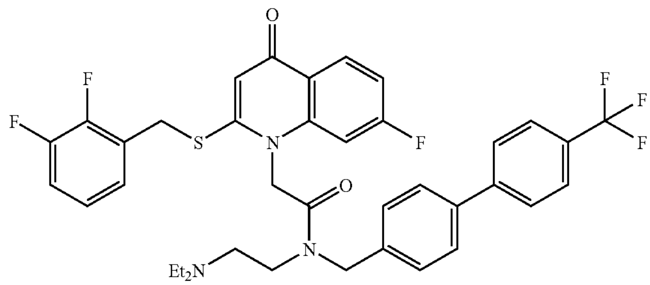 | N-(2-Diethylaminoethyl)-2-[2-(2,3-difluorobenzylthio)7-fluoro-4-oxo-4H-quinolin-1-yl]-N-(4'-trifluoromethylbiphenyl-4-ylmethyl)-acetamide bitartrate |
| 34 | Int. E26<br>Int. A2 | 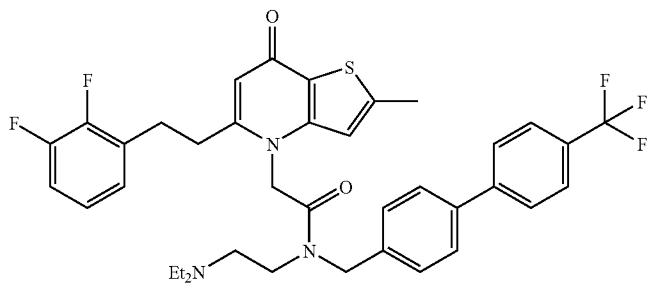 | N-(2-Diethylaminoethyl)-5-[2-(2-(2,3-difluorophenyl)ethyl)-2-methyl-7-oxo-7H-thieno[3,2-b]pyridin-4-yl]-N-(4'-trifluoromethylbiphenyl-4-ylmethyl)-acetamide bitartrate |
| 35 | Int. E24<br>Int. A2 | 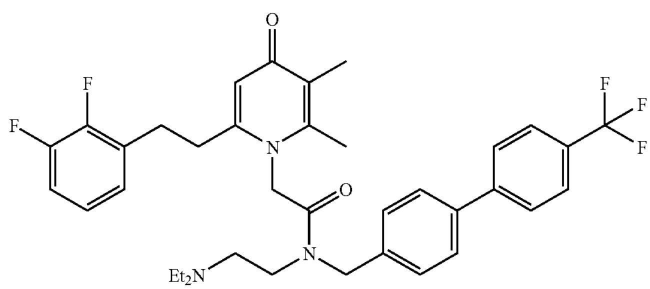 | N-(2-Diethylaminoetbyl)-2-[2-(2-(2,3-difluorophenyl)ethyl)-5,6-dimethyl-4-oxo-4H-pyridin-1-yl]-N-(4'-trifluoromethylbiphenyl-4-ylmethyl)acetamide bitartrate |
| 36 | Int. E23<br>Int. A2 | 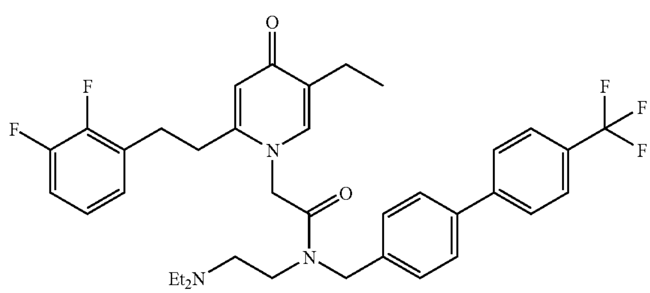 | N-(2-Diethylaminoethyl)-2-[2-(2-(2,3-difluorophenyl)ethyl)-5-ethyl-4-oxo-4H-pyridin-1-yl]-N-(4'-trifluoromethylbiphenyl-4-ylmethyl)acetamide bitartrate |
| 37 | Int. E2<br>Int. A42 | 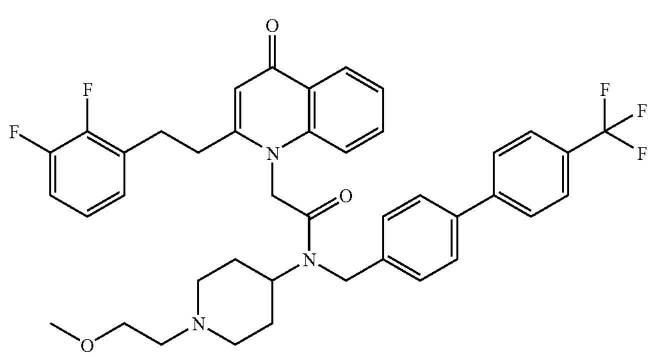 | N-(1-(2-methoxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |

| Ex. No. | Precursors | Structure | Name |
|---|---|---|---|
| 38 | Int. E2<br>Int. A5 | 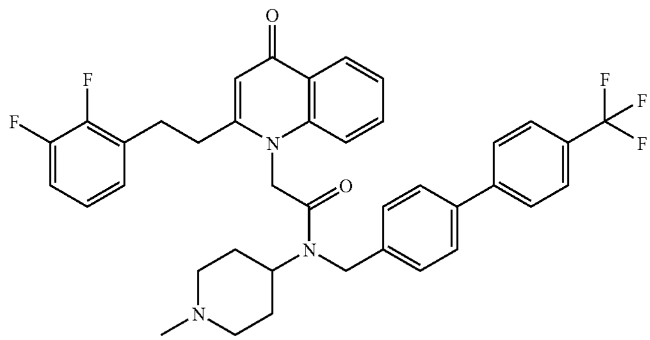 | N-(1-methylpiperidin-4-yl)-2-[2-(2-(2,3-difluorophenyl)ethyl)-4-oxo-4H-quinolin-1-yl]-N-(4'-trifluoro-methylbiphenyl-4-ylmethyl)-acetamide bitartrate |
| 39 | Int. E27<br>Int. A2 | 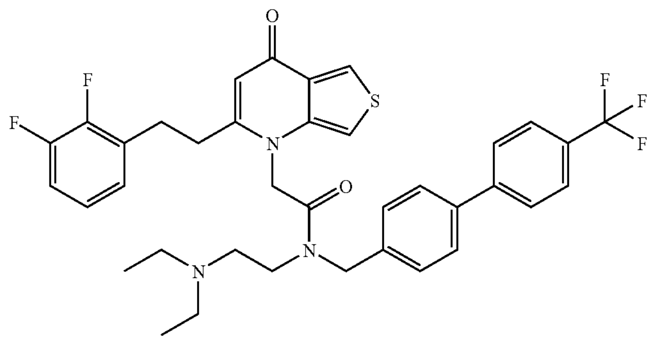 | N-(2-Diethylaminoethyl)-2-[2-(2-(2,3-difluorophenyl)ethyl)-4-oxo-4H-thieno[3,4-b]pyridin-1-yl]-N-(4'-trifluoromethylbiphenyl-4-ylmethyl)acetamide bitartrate |
| 40 | Int. E1<br>Int. A40 | 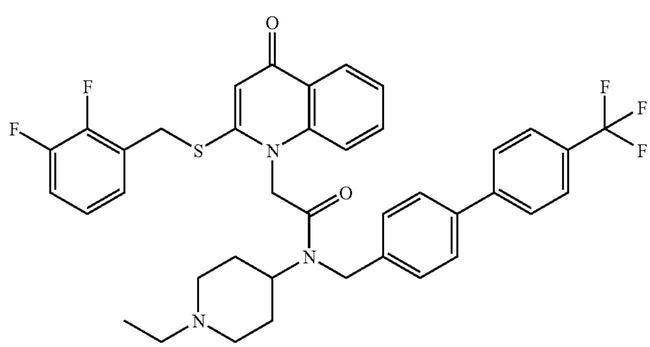 | N-(1-Ethylpiperidin-4-yl)-2-[2-(2,3-difluorobenzylthio)-4-oxo-4H-quinolin-1-yl]-N-(4'-trifluoro-methylbiphenyl-4-ylmethyl)-acetamide bitartrate |
| 41 | Int. E1<br>Int. A22 | 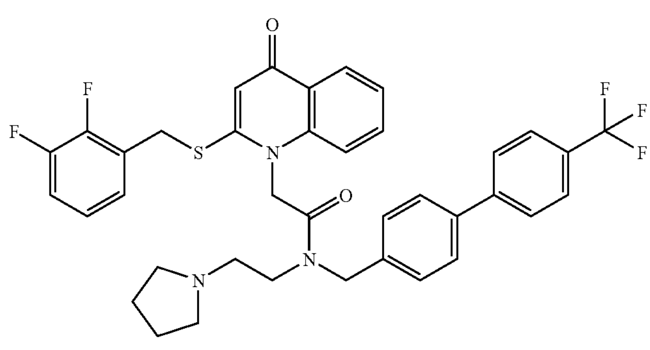 | N-(2-pyrrolidin-1-ylethyl)-2-[2-(2,3-difluorobenzylthio)-4-oxo-4H-quinolin-1-yl]-N-(4'-trifluoro-methylbiphenyl-4-methyl)-acetamide bitartrate |

-continued

| Ex. No. | Precursors | Structure | Name |
|---|---|---|---|
| 42 | Int. E30<br>Int. A40 | 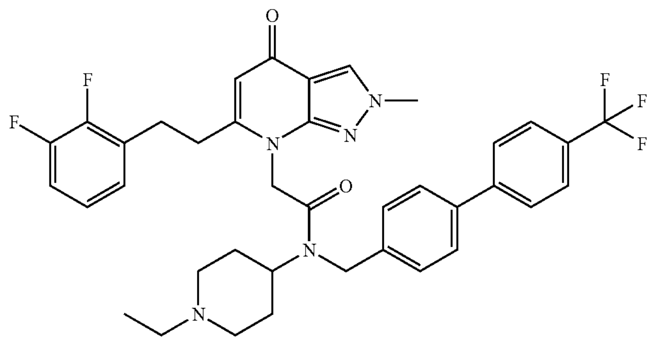 | N-(1-Ethylpiperidin-4-yl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)-acetamide bitartrate |
| 43 | Int. E1<br>Int. A41 | 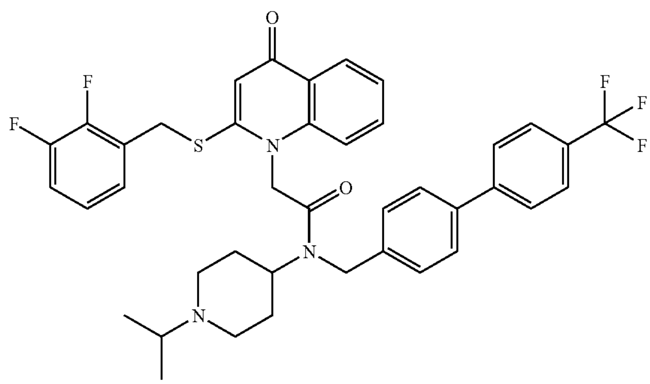 | N-(1-isopropylpiperidin-4-yl)-2-[2-(2,3-difluorobenzylthio)-4-oxo-4H-quinolin-1-yl]-N-4'-trifluoromethylbiphenyl-4-ylmethyl)-acetamide bitartrate |
| 44 | Int. E2<br>Int. A25 | 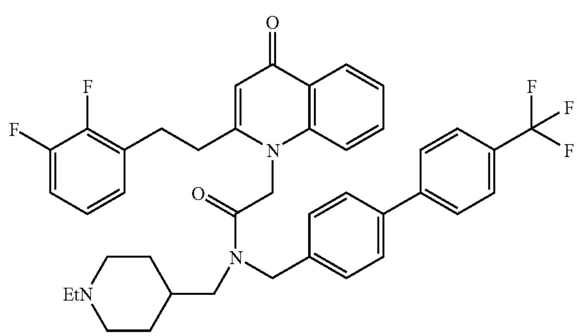 | N-(1-ethylpiperidin-4-ylmethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate |
| 45 | Int. E1<br>Int. A24 | 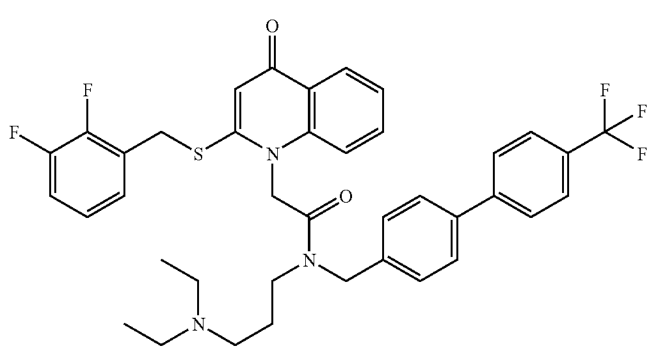 | N-(3-Diethylaminopropyl)-2-[2-(2,3-difluorobenzylthio)-4-oxo-4H-quinolin-1-yl]-N-(4'-trifluoromethylbiphenyl-4-ylmethyl)-acetamide bitartrate |

-continued

| Ex. No. | Precursors | Structure | Name |
|---|---|---|---|
| 46 | Int. E2<br>Int. A32 | 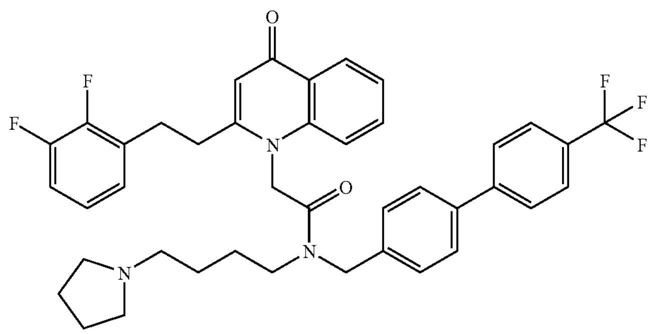 | N-(4-pyrrolidin-1-ylbutyl)-2-[2-(2-(2,3-difluorophenyl)ethyl-4-oxo-4H-quinolin-1-yl]-N-(4'-trifluoromethylbiphenyl-4-ylmethyl)-acetamide bitartrate |
| 47 | Int. E2<br>Int. A24 | 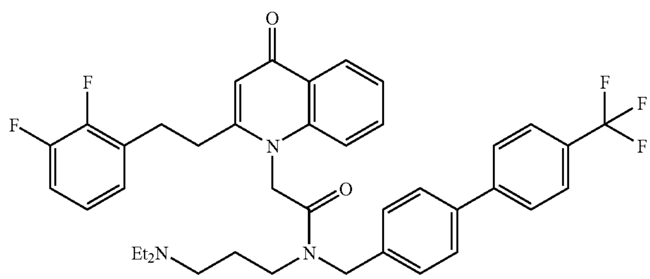 | N-(3-Diethylaminopropyl)-2-[2-(2-(2,3-difluorophenyl)ethyl)4-oxo-4H-quinolin-1-yl]-N-(4'-trifluoromethylbiphenyl-4-ylmethyl)-acetamide bitartrate |
| 48 | Int. E1<br>Int. A32 | 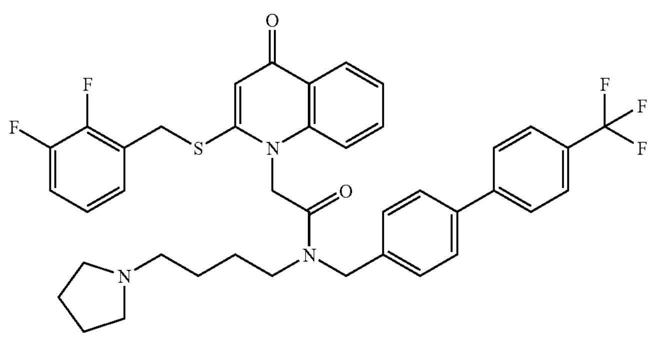 | N-(4-pyrrolidin-1-ylbutyl)-2-[2-(2,3-difluorobenzylthio)-4-oxo-4H-quinolin-1-yl]-N-(4'-trifluoromethylbiphenyl-4-ylmethyl)-acetamide bitartrate |
| 49 | Int. E25<br>Int. A40 | 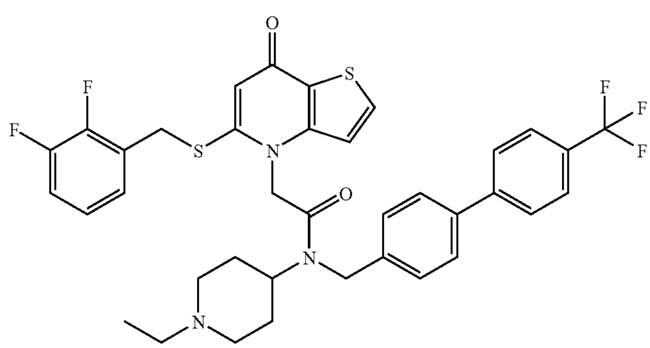 | N-(1-Ethylpiperidin-4-yl)-2-[5-(2,3-difluorobenzylthio)-7-oxo-7H-thieno[3,2-b]pyridin-4-yl]-N-(4'-trifluoromethylbiphenyl-4-ylmethyl)acetamide bitartrate |
| 50 | Int. E28<br>Int. A2 | 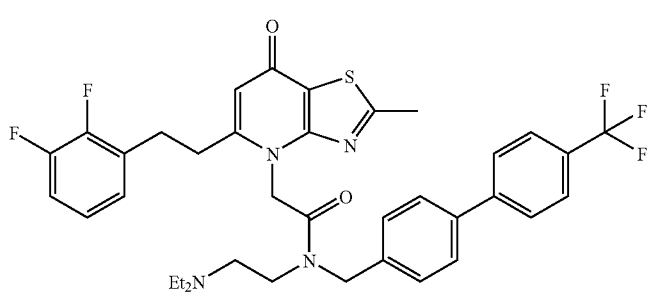 | N-(2-Diethylaxninoethyl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)-acetamide bitartrate |

-continued

| Ex. No. | Precursors | Structure | Name |
|---|---|---|---|
| 51 | Int. E1<br>Int. A27 | 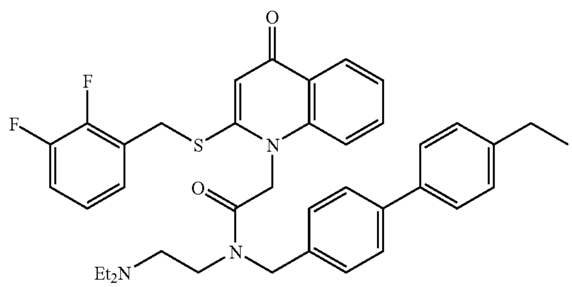 | N-(2-Diethylaminoethyl)-2-[2-(2,3-difluorobenzylthio)-4-oxo-4H-quinolin-1-yl]-N-(4'-ethylbiphenyl-4-ylmethyl)acetamide bitartrate |
| 52 | Int. E2<br>Int. A27 | 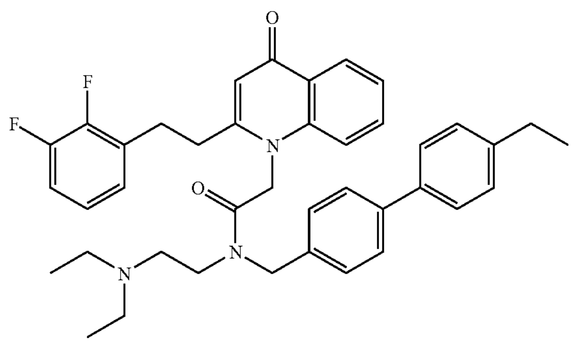 | N-(2-Diethylaminoethyl)-2-[2-(2-(2,3-difluorophenyl)ethyl)-4-oxo-4H-quinolin-1-yl]-N-(4'-ethylbiphenyl-4-ylmethyl)-acetamide bitartrate |
| 53 | Int. E1<br>Int. A28 | 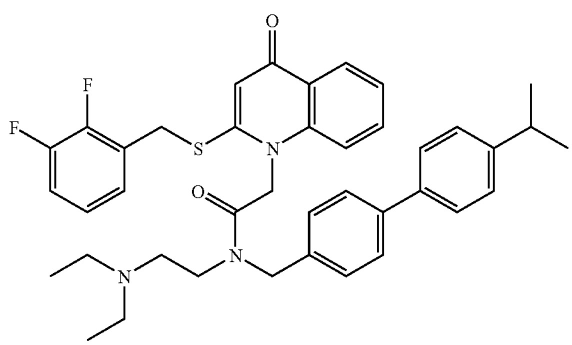 | N-(2-Diethylaminoethyl)-2-[2-(2,3-difluorobenzylthio)-4-oxo-4H-quinolin-1-yl]-N-(4'-isopropylbiphenyl-4-ylmethyl)-acetamide bitartrate |
| 54 | Int. E2<br>Int. A28 | 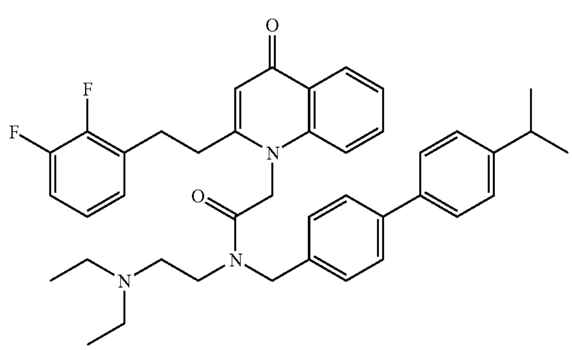 | N-(2-Diethylaminoethyl)-2-[2-(2-(2,3-difluorophenyl)ethyl)-4-oxo-4H-quinolin-1-yl]-N-(4'-isopropylbiphenyl-4-ylmethyl)-acetamide bitartrate |

-continued

| Ex. No. | Precursors | Structure | Name |
|---|---|---|---|
| 55 | Int. E34<br>Int. A2 | 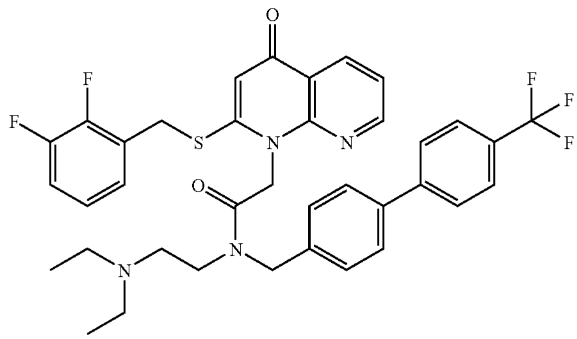 | N-(2-Diethylaminoethyl)-2-[2-(2,3-difluorobenzylthio)-4-oxo-4H-[1,8]naphthyridin-1-yl]-N-(4'-trifluoromethylbiphenyl-4-ylmethyl)acetamide bitartrate |
| 56 | Int. E34<br>Int. A40 | 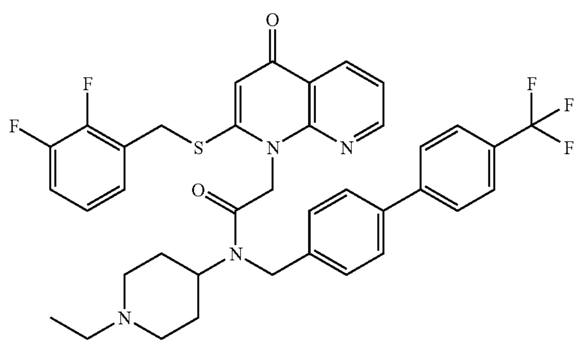 | N-(1-Ethylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate |
| 57 | Int. E2<br>Int. A26 | 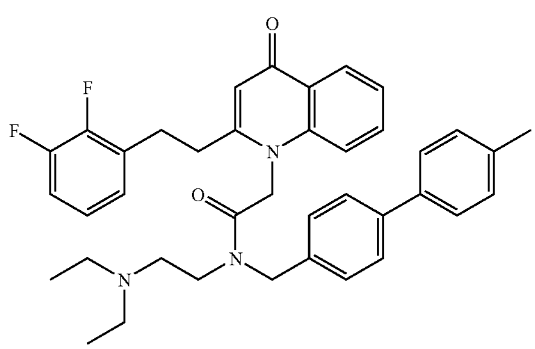 | N-(2-Diethylaminoethyl)-2-[2-(2-(2,3-difluorophenyl)ethyl)-4-oxo-4H-quinolin-1-yl]-N-(4'-methylbiphenyl-4-ylmethyl)-acetamide bitartrate |
| 58 | Int. E1<br>Int. A26 | 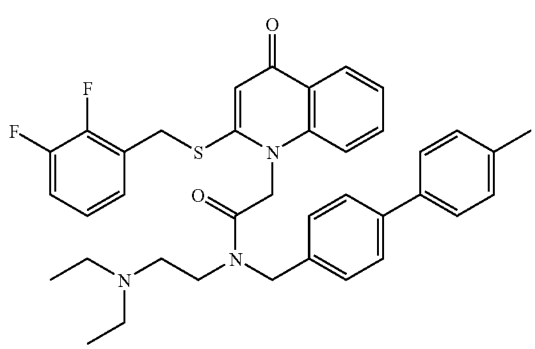 | N-(2-Diethylaminoethyl)-2-[2-(2,3-difluorobenzylthio)-4-oxo-4H-quinolin-1-yl]-N-(4'-methylbiphenyl-4-ylmethyl)-acetamide bitartrate |

| Ex. No. | Precursors | Structure | Name |
|---|---|---|---|
| 59 | Int. E2<br>Int. A43 | 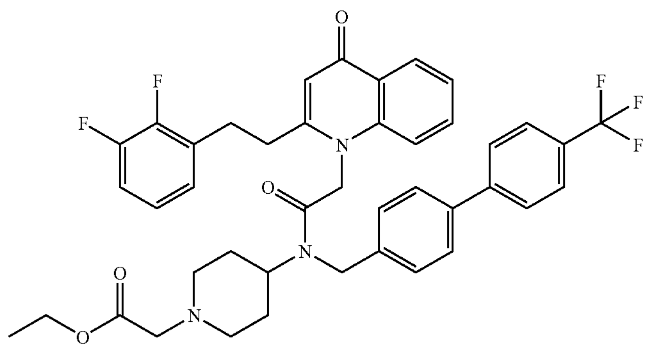 | N-(1-Ethoxycarbonylmethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |
| 60 | Int. E21<br>Int. A41 | 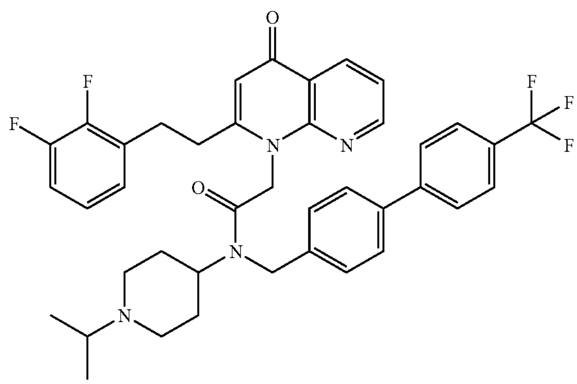 | N-(1-isopropylpiperidin-4-yl)-2-[2-(2-(2,3-difluorophenyl)ethyl)-4-oxo-4H-[1,8]naphthyridin-yl]-N-(4'-trifluoromethylbiphenyl-4-ylmethyl)acetamide bitartrate |
| 61 | Int. E1<br>Int. A30 | 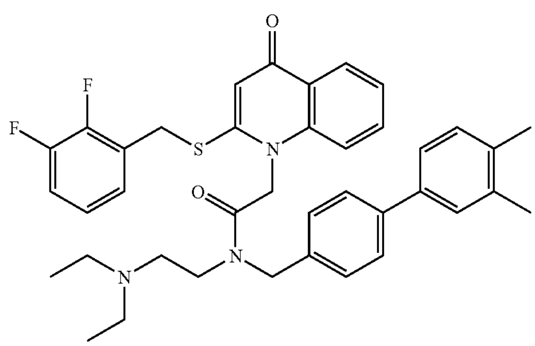 | N-(2-Diethylaminoethyl)-2-[2-(2,3-difluorobenzylthio)-4-oxo-4H-quinolin-1-yl]-N-(3',4'-dimethylbiphenyl-4-ylmethyl)-acetamide bitartrate |
| 62 | Int. E21<br>Int. A48 | 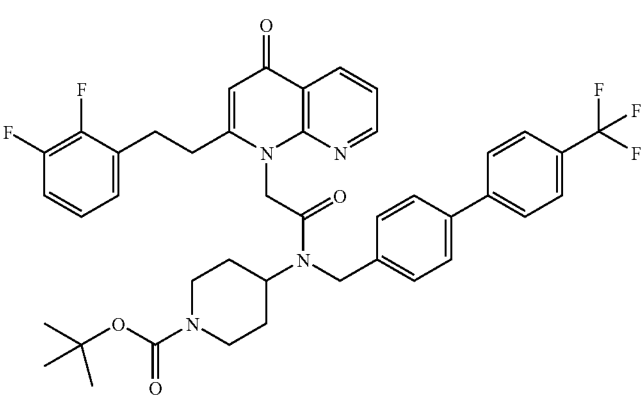 | N-(1-(t-butoxycarbonyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate |

-continued

| Ex. No. | Precursors | Structure | Name |
| --- | --- | --- | --- |
| 63 | Int. E1<br>Int. A31 | 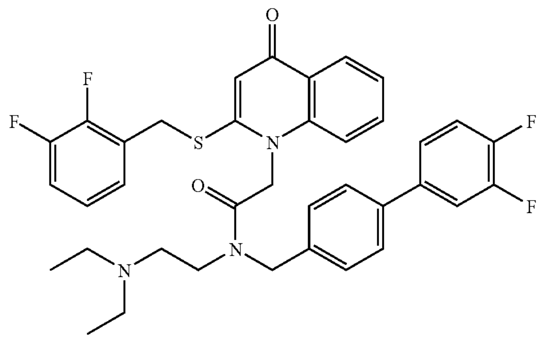 | N-(2-Diethylaminoethyl)-2-[2-(2,3-difluorobenzylthio)-4-oxo-4H-quinolin-1-yl]-N-(3',4'-difluorobiphenyl-4-ylmethyl)-acetamide bitartrate |
| 64 | Int. E35<br>Int. A2 | 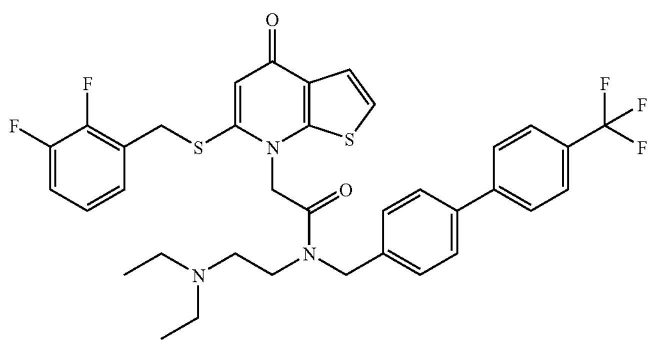 | N-(2-Diethylaminoethyl)-2-[6-(2,3-difluorobenzylthio)-4-oxo-4H-thieno[2,3-b]pyridin-7-yl]-N-(4'-trifluoromethylbiphenyl-4-ylmethyl)acetamide bitartrate |
| 65 | Int. E34<br>Int. A5 | 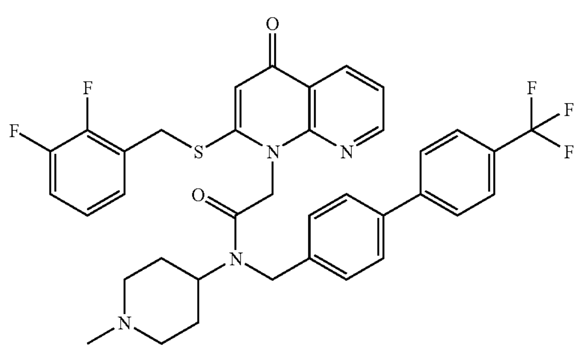 | N-(1-methylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate |
| 66 | Int. E2<br>Int. A40 | 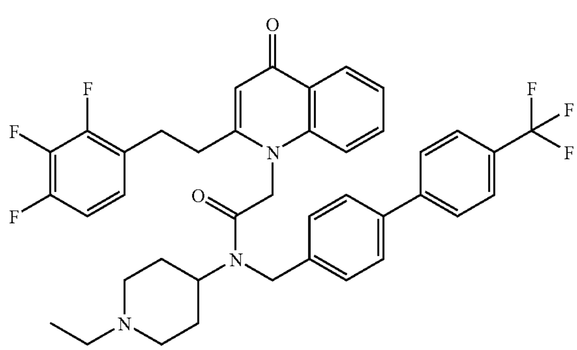 | N-(1-Ethylpiperidin-4-yl)-2-[2-(2-(2,3,4-trifluorophenylethyl)-4-oxo-4H-quinolin-1-yl]-N-(4'-trifluoromethylbiphenyl-4-ylmethyl)-acetamide bitartrate |

-continued

| Ex. No. | Precursors | Structure | Name |
|---|---|---|---|
| 67 | Int. E29<br>Int. A2 | 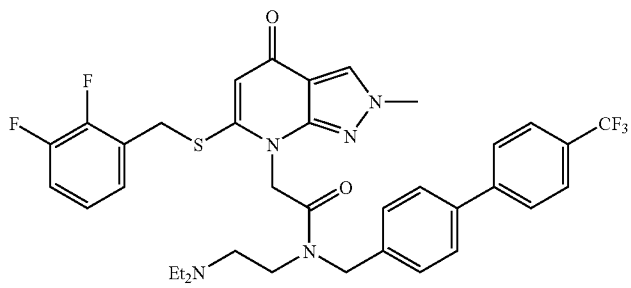 | N-(2-diethylaminoethyl)-2-[6-(2,3-difluorobenzylthio)-2-methyl-4-oxo-2,4-dihydro-pyrazolo[3,4-b]pyridin-7-yl]-N-(4'-trifluoromethylbiphenyl-4-ylmethyl)acetamide bitartrate |
| 68 | Int. E31<br>Int. A40 | 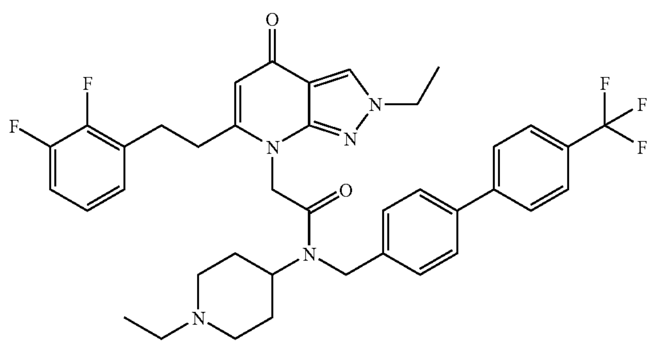 | N-(1-Ethylpiperidin-4-yl)-2-[6-(2-(2,3-difluorophenyl)ethyl)-2-ethyl-4-oxo-2,4-dihydropyrazolo[3,4-b]pyridin-7-yl]-N-(4'-trifluoromethylbiphenyl-4-ylmethyl)acetamide bitartrate |
| 69 | Int. E32<br>Int. A40 | 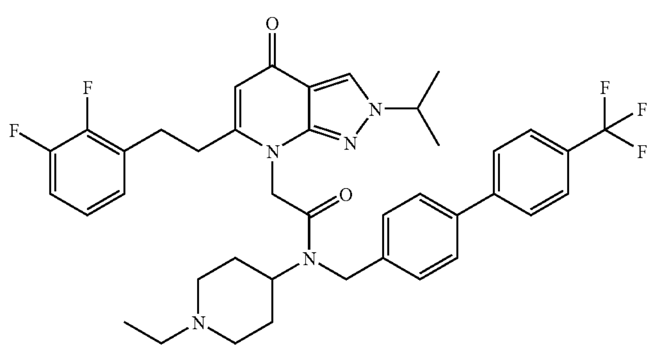 | N-(1-Ethylpiperidin-4-yl)-2-[6-(2-(2,3-difluorophenyl)ethyl)-2-isopropyl-4-oxo-2,4-dihydropyrazolo[3,4-b]pyridin-7-yl]-N-(4'-trifluoromethylbiphenyl-4-ylmethyl)acetamide bitartrate |
| 70 | Int. E2<br>Int. A29 | 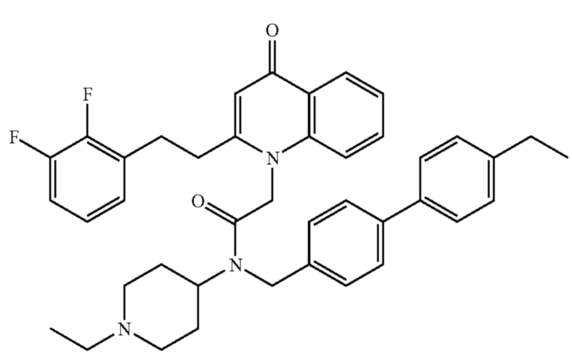 | N-(1-Ethylpiperidin-4-yl)-2-[2-(2-(2,3-difluorophenyl)ethyl)-4-oxo-4H-quinolin-1-yl]-N-(4'-ethyl-biphenyl-4-ylmethyl)acetamide bitartrate |

-continued

| Ex. No. | Precursors | Structure | Name |
|---|---|---|---|
| 71 | Int. E28<br>Int. A41 | 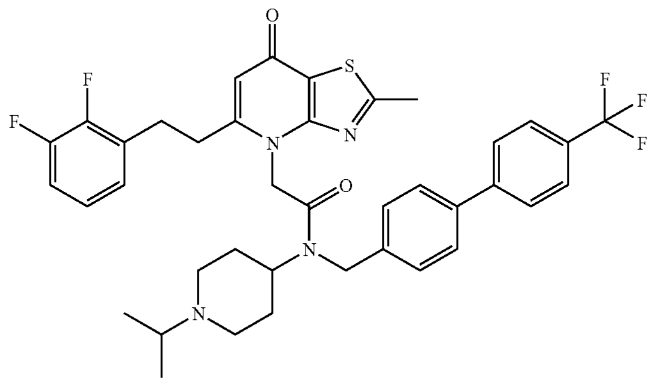 | N-(1-isopropylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)-acetamide bitartrate |
| 72 | Int. E28<br>Int. A42 | 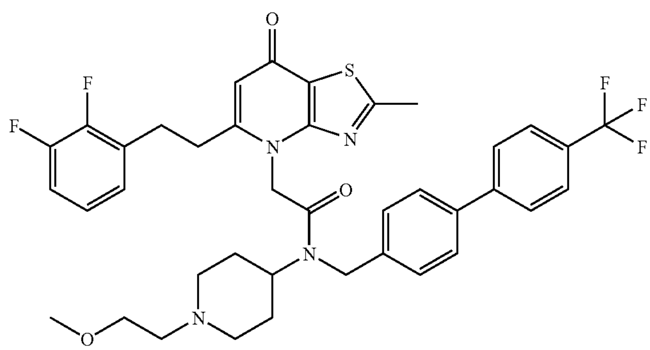 | N-(1-(2-methoxyethyl)piperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate |
| 73 | Int. E36<br>Int. A40 | 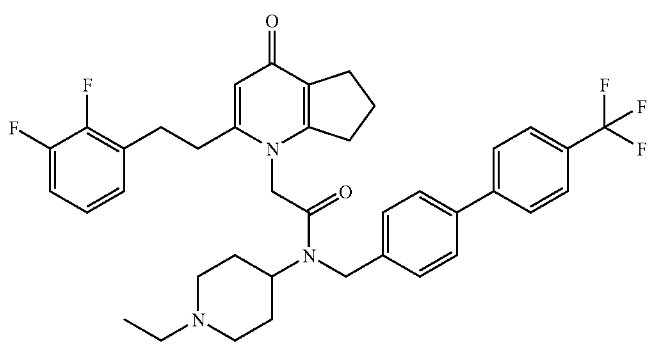 | N-(1-Ethylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |
| 74 | Int. E36<br>Int. A5 | 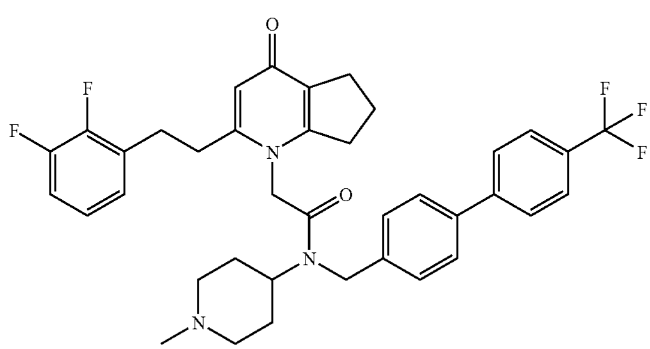 | N-(1-methylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |

-continued

| Ex. No. | Precursors | Structure | Name |
|---|---|---|---|
| 75 | Int. E36<br>Int. A42 | 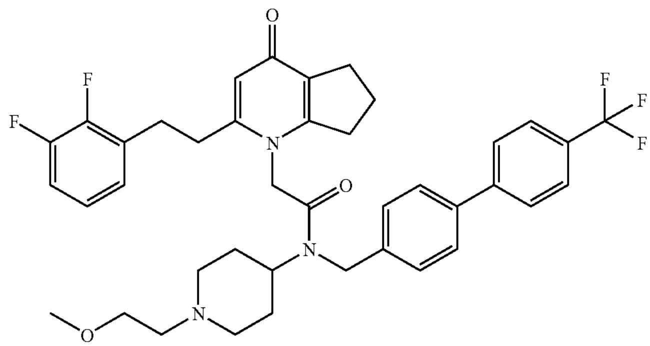 | N-(1-(2-methoxyethyl)piperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |
| 76 | Int. E36<br>Int. A41 | 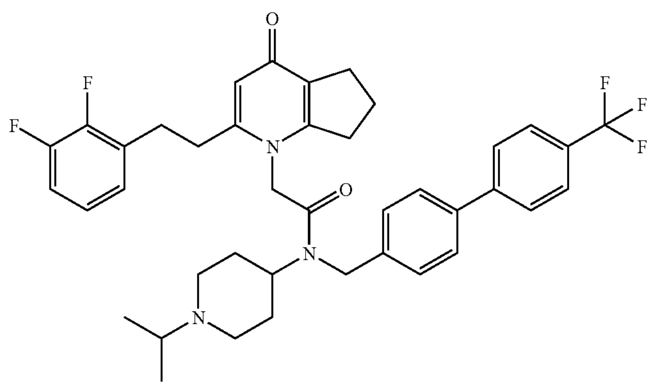 | N-(1-isopropylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |
| 77 | Int. E13<br>Int. A40 | 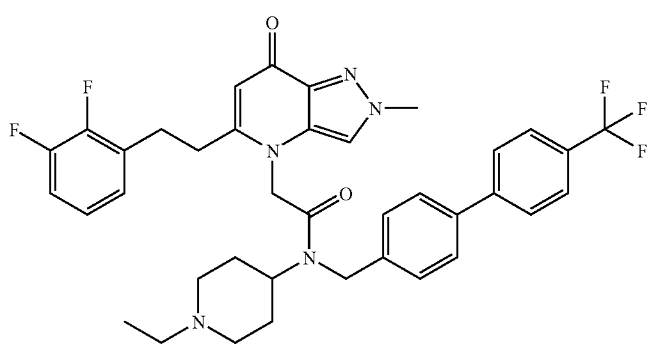 | N-(1-Ethylpiperidin-4-yl)-2-[5-(2-(2,3-difluorophenyl)ethyl)-2-methyl-7-oxo-2,7-dihydropyrazolo'4,3-b]pyridin-4-yl]-N-(4'-trifluoromethylbiphenyl-4-ylmethyl)acetamide bitartrate |
| 78 | Int. E14<br>Int. A40 | 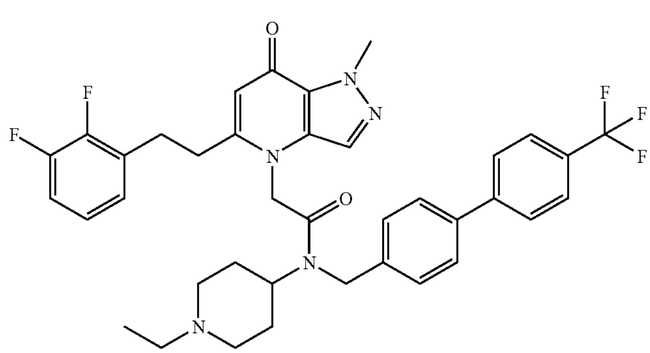 | N-(1-Ethylpiperidin-4-yl)-2-[5-(2-(2,3-difluorophenyl)ethyl)-1-methyl-7-oxo-1,7-dihydropyrazolo[4,3-b]pyridin-4-yl]-N-(4'-trifluoromethylbiphenyl-4-ylmethyl)acetamide bitartrate |

-continued

| Ex. No. | Precursors | Structure | Name |
|---|---|---|---|
| 79 | Int. E36<br>Int. A2 | 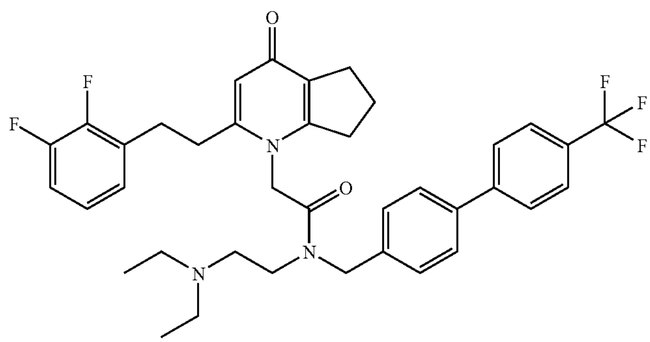 | N-(1-Ethylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |
| 80 | Int. E33<br>Int. A40 | 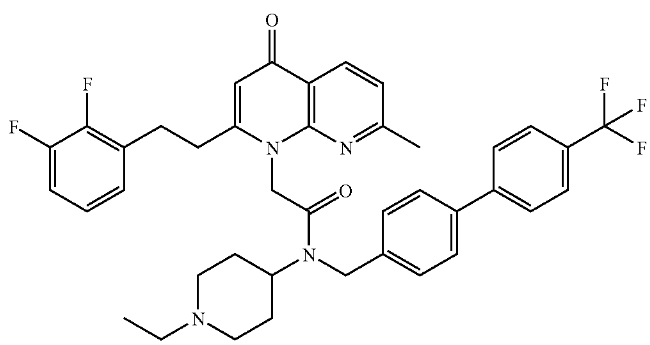 | N-(1-Ethylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate |
| 81 | Int. E33<br>Int. A2 | 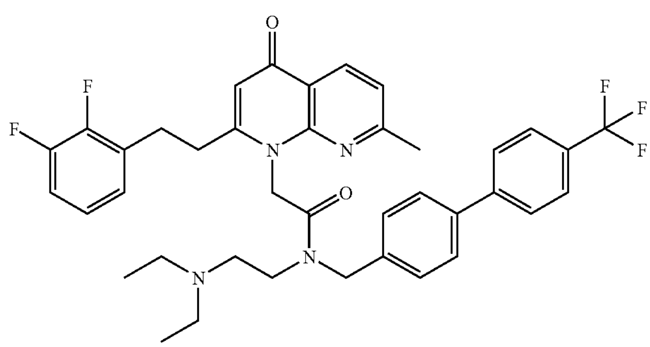 | N-(2-Diethylaminoethyl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate |
| 82 | Int. E33<br>Int. A5 | 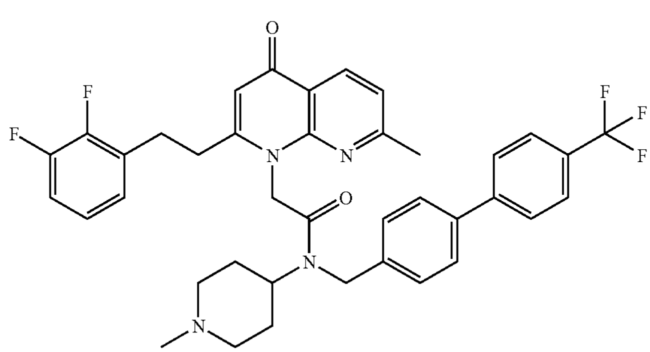 | N-(1-methylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate |

-continued

| Ex. No. | Precursors | Structure | Name |
|---|---|---|---|
| 83 | Int. E33<br>Int. A41 | 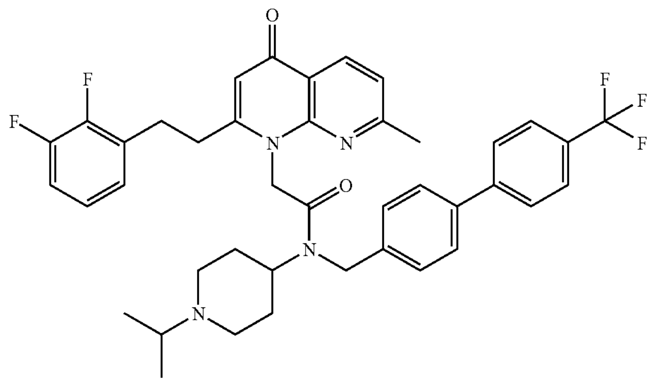 | N-(1-isopropylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate |
| 84 | Int. E33<br>Int. A42 | 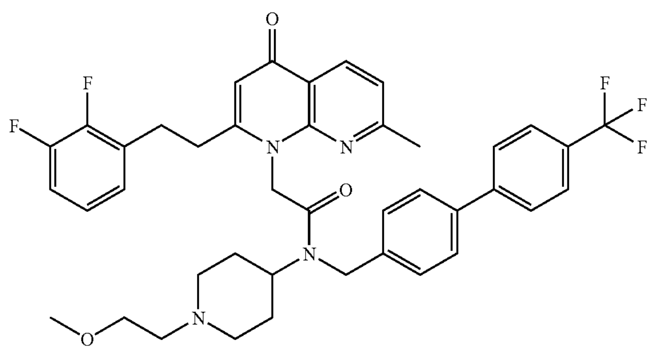 | N-(1-(2-methoxyethyl)piperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate |
| 85 | Int. E12<br>Int. A5 | 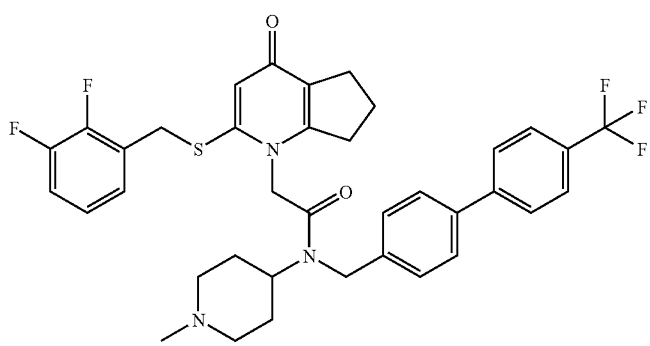 | N-(1-methylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate |
| 86 | Int. E12<br>Int. A40 | 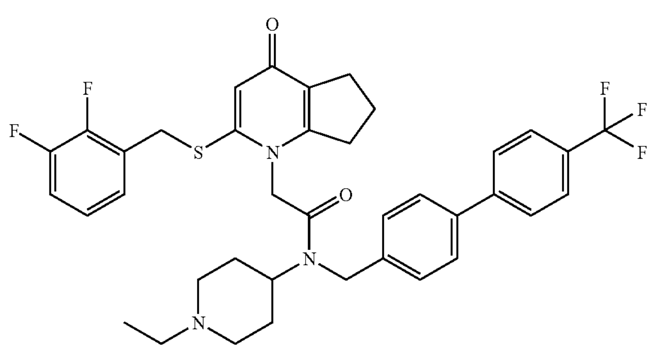 | N-(1-Ethylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate |

-continued

| Ex. No. | Precursors | Structure | Name |
|---|---|---|---|
| 87 | Int. E12<br>Int. A41 | 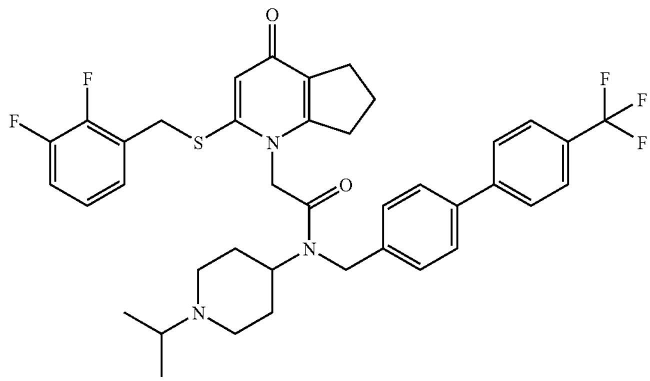 | N-(1-isopropylpiperidin-4-yl)-2-[2-(2,3-difluorobenzylthio)-4-oxo-5,6-trimethylenepyridin-1-yl[-N-(4'-trifluoromethylbiphenyl-4-ylmethyl)acetamide bitartrate |
| 88 | Int. E12<br>Int. A42 | 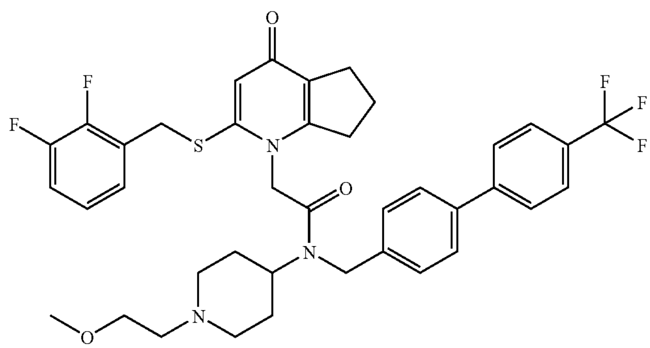 | N-(1-(2-methoxyethyl)piperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate |
| 89 | Int. E37<br>Int. A2 | 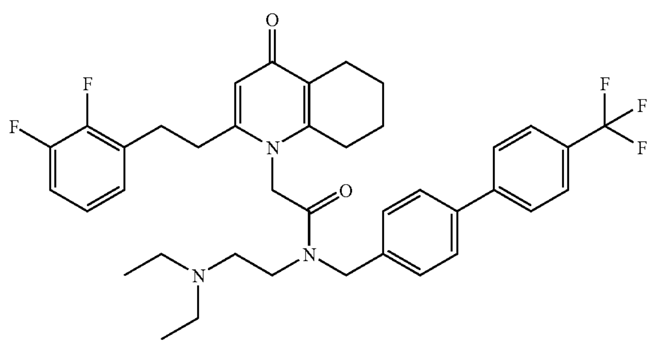 | N-(2-Diethylaminoethyl)-2-[2-(2,3-difluorophenyl)ethyl)-4-oxo-5,6-tetramethylenepyridin-1-yl]-N-(4'-trifluoromethylbiphenyl-4-ylmethyl)acetamide bitartrate |
| 90 | Int. E1<br>Int. A45 | 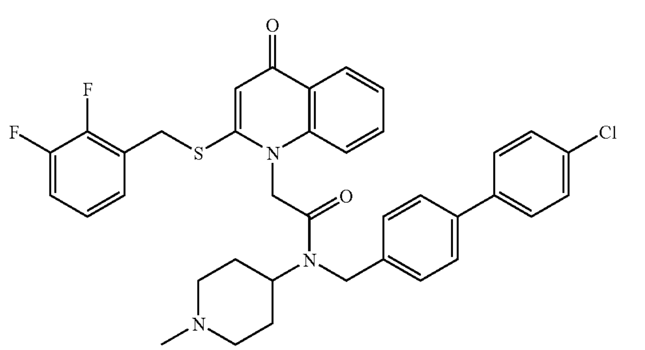 | N-(1-methylpiperidin-4-yl)-2-[2-(2,3-difluorobenzylthio)-4-oxo-4H-quinolin-1-yl]-N-(4'-chlorobiphenyl-4-ylmethyl)-acetamide bitartrate |

-continued

| Ex. No. | Precursors | Structure | Name |
|---|---|---|---|
| 91 | Int. E2<br>Int. A45 | 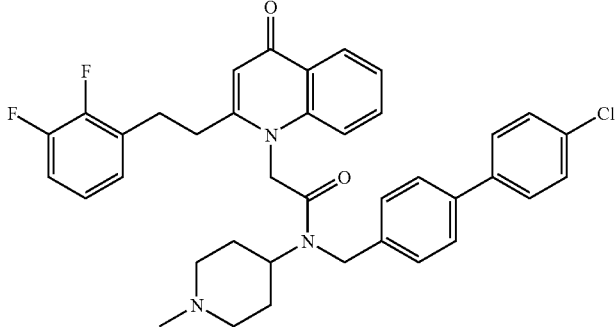 | N-(1-methylpiperidin-4-yl)-2-[2-(2-(2,3-difluorophenyl)ethyl)-4-oxo-4H-quinolin-1-yl]-N-(4'-chlorobiphenyl-4-ylmethyl)-acetamide bitartrate |
| 92 | Int. E2<br>Int. A44 | 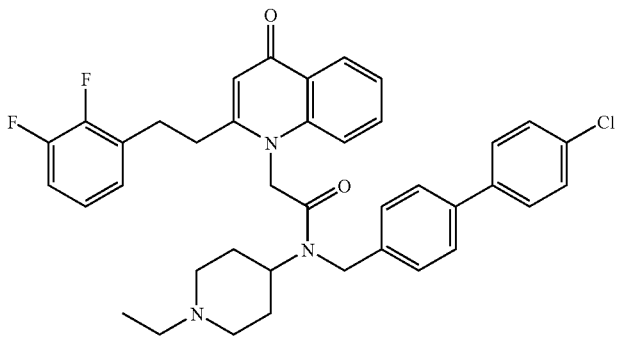 | N-(1-Ethylpiperidin-4-yl)-2-[2-(2-(2,3-difluorophenyl)ethyl)-4-oxo-4H-quinolin-1-yl]-N-(4'-chlorobiphenyl-4-ylmethyl)-acetamide bitartrate |
| 93 | Int. E2<br>Int. A47 | 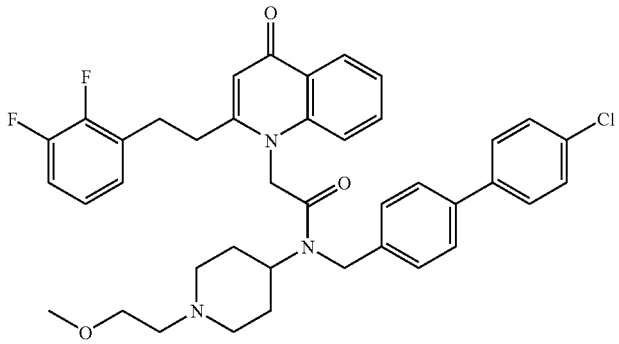 | N-(1-(2-methoxyethyl)piperidin-4-yl)-2-[2-(2-(2,3-difluorophenyl)ethyl)-4-oxo-4H-quinolin-1-yl]-N-(4'-chlorobiphenyl-4-ylmethyl)-acetamide bitartrate |
| 94 | Int. E2<br>Int. A46 | 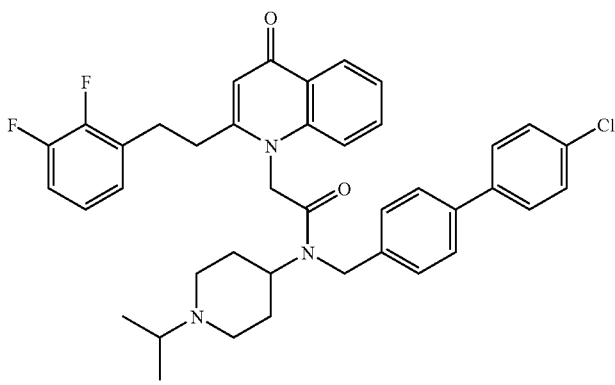 | N-(1-isopropylpiperidin-4-yl)-2-[2-(2-(2,3-difluorophenyl)ethyl)-4-oxo-4H-quinolin-1-yl]-N-(4'-chlorobiphenyl-4-ylmethyl)-acetamide bitartrate |

-continued

| Ex. No. | Precursors | Structure | Name |
|---|---|---|---|
| 95 | Int. E30<br>Int. A2 | 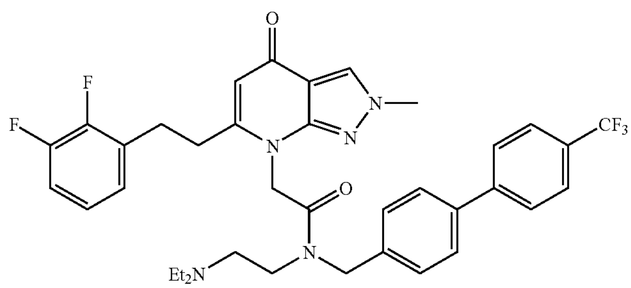 | N-(2-diethylaminoethyl)-2-[6-(2-(2,3-difluorophenyl)ethyl)-2-methyl-4-oxo-4H-pyrazolo[3,4-b]pyridin-7-yl]-N-(4'-trifluoro-methylbiphenyl-4-ylmethyl)-acetamide bitartrate |
| 96 | Int. E34<br>Int. A48 | 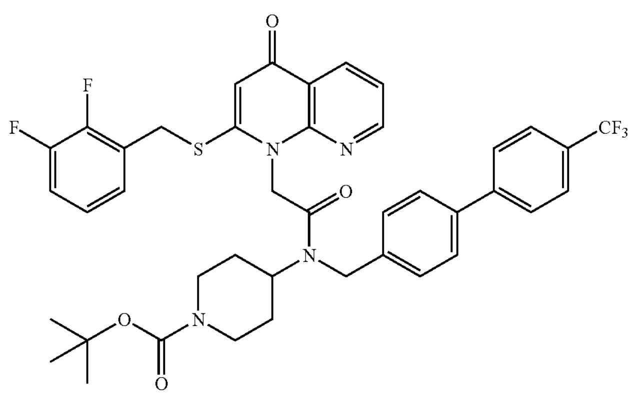 | N-(1-(t-butoxycarbonyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide |
| 97 | Int. E38<br>Int. A40 | 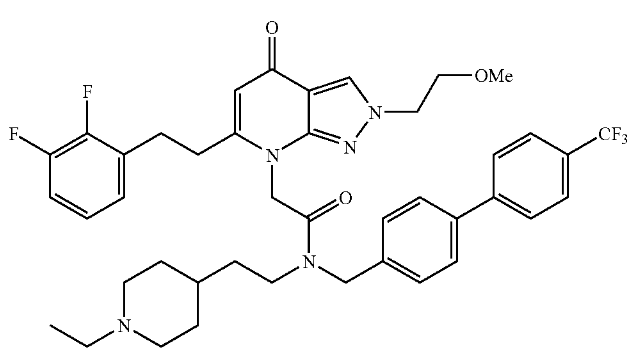 | N-(1-ethylpiperidin-4-yl)-2-[6-(2-(2,3-difluorophenyl)ethyl)-2-(2-methoxyethyl)-4-oxo-4H-pyrazolo-[3,4-b]pyridin-7-yl]-N-(4'-trifluoro-methylbiphenyl-4-ylmethyl)-acetamide bitartrate |

The following intermediates were prepared by the method of Example 1, but were not included in biological testing:

| No. | Precursors | Structure | Name |
|---|---|---|---|
| F1 | Int. E1<br>Int. A48 | 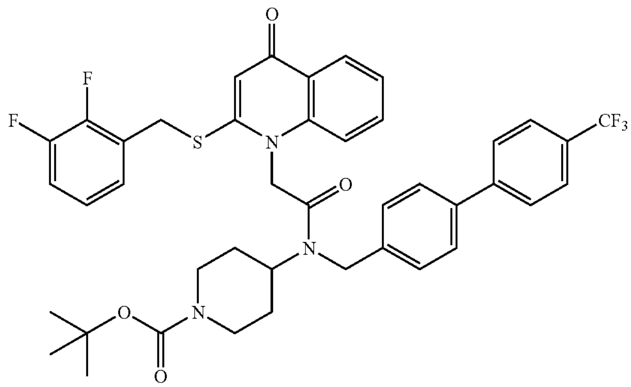 | N-(1-(t-butoxycarbonyl)piperidin-4-yl)-2-[2-(2,3-difluorobenzylthio)-4-oxo-4H-quinolin-1-yl]-N-(4'-trifluoromethylbiphenyl-4-ylmethyl)acetamide |
| F2 | Int. E2<br>Int. A48 | 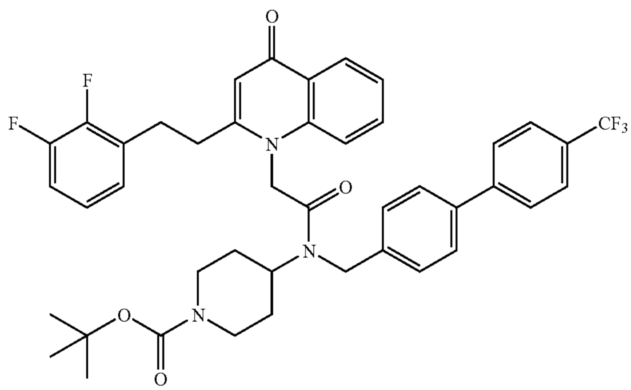 | N-(1-(t-butoxycarbonyl)piperidin-4-yl)-2-[2-(2-(2,3-difluorophenyl)ethyl]-4-oxo-4H-quinolin-1-yl]-N-(4'-trifluoromethylbiphenyl-4-ylmethyl)-acetamide |
| F3 | Int. E36<br>Int. A48 | 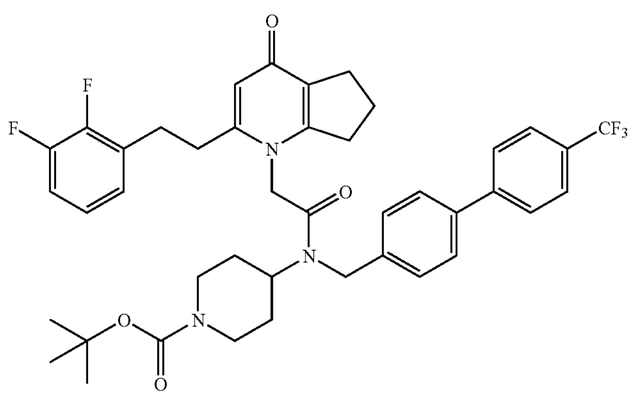 | N-(1-(t-butoxycarbonyl)piperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide |
| F4 | Int. E1<br>Int. A33 | 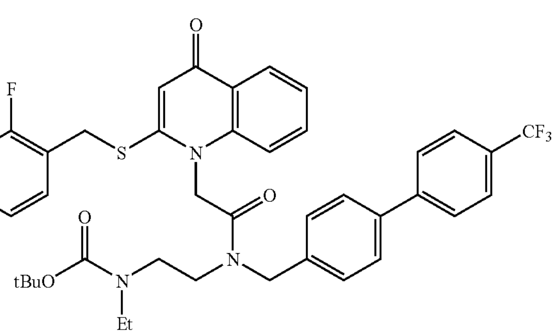 | N-(2-(N'-ethyl-N'-(t-butoxycarbonyl)aminoethyl)-2-[2-(2,3-difluorobenzylthio)-4-oxo-4H-quinolin-1-yl]-N-(4'-trifluoromethylbiphenyl-4-ylmethyl)-acetamide |

| No. | Precursors | Structure | Name |
|---|---|---|---|
| F5 | Int. E2<br>Int. A33 | 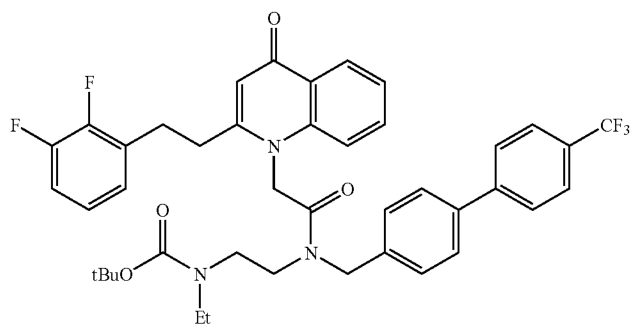 | N-(2-(N'-ethyl-N'-(t-butoxycarbonyl)aminoethyl)-2-(2-(2-(2,3-difluorophenyl)ethyl)-4-oxo-4H-quinolin-1-yl]-N-(4'-trifluoromethylbiphenyl-4-ylmethyl)acetamide |

Example 99

N-(2-Diethylaminoethyl)-2-[4-oxo-2-(2-(2,3,4-trifluorophenyl)ethyl)-4H-quinolin-1-yl]-N-(4'-trifluoromethyl-biphenyl-4-ylmethyl)acetamide bitartrate

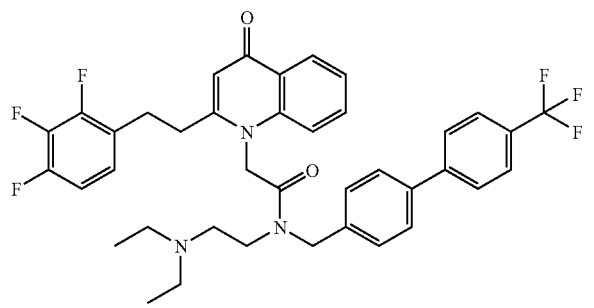

A solution of N,N-diethyl-N'-(4'-trifluoromethyl-biphenyl-4-ylmethyl)ethane-1,2-diamine (0.242 g, 0.69 mmol) (Int. A2), 1-(3-dimethylaminopropyl)3-ethylcarbodiimide (0.265 g, 1.39 mmol), 1-hydroxybenzotriazole hydrate (0.02 g), 2-(4-oxo-2-[2-(2,3,4-trifluorophenyl)ethyl]-4H-quinolin-1-yl)-acetic acid (Int. E10) (0.25, 0.69 mmol) and N,N-diisopropylethylamine (0.15 ml, 0.86 mmmol) in dichloromethane (5 ml) was stirred at ambient temperature overnight then washed with aqueous sodium bicarbonate and evaporated. The residue was purified by chromatography (10 g silica cartridge, dichloromethane-50% acetone/dichloromethane) and triturated with hexane to give the title compound as a white solid (0.23 g, 47%). $^1$H-NMR (d6 DMSO, rotamer mixture) δ 0.89–0.98 (6H, m), 2.33–2.67 (6H, m), 2.84–3.00 (4H, m), 3.45–3.61 (2H, m), 4.67/4.92 (2H, 2×s), 5.24/5.50 (2H, 2×s), 6.02/6.05 (1H, 2×s), 7.19–7.20 (4H, m), 7.51–7.88 (9H, m), 8.16 (1H, t); MS (APCI+) found (M+1)=694. $C_{39}H_{37}F_6N_3O_2$ requires 693.

d-Tartaric acid (0.028 g, 0.19 mmol) was added to a solution of the free base (0.13 g, 0.19 mmol) in methanol (5 ml) with stirring. The resulting solution was evaporated to yield the salt (0.158 g). $^1$H-NMR (d6 DMSO, rotamer mixture) δ 1.00 (6H, br s), 2.51–2.97 (10H, m), 3.64 (2H, br s), 4.23 (2H, br s), 4.67/4.93 (2H, 2×s), 5.28/5.50 (2H, 2×s), 6.05 (1H, br s) 7.23–7.83 (13H, m), 8.17 (1H, s); MS (APCI+) found (M+1)=694. $C_{39}H_{37}F_6N_3O_2$ requires 693.

The following compounds were prepared by the method of Example 99

| Ex. No. | Precursors | Structure | Name |
|---|---|---|---|
| 100 | Int. E7<br>Int. A2 | 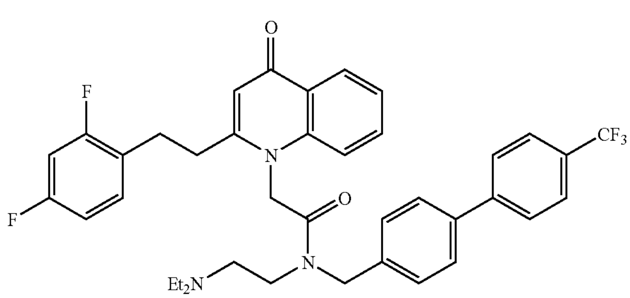 | N-(2-Diethylaminoethyl)-2-[2-(2-(2,4-difluorophenyl)ethyl)-4-oxo-4H-quinolin-1-yl]-N-(4'-trifluoromethylbiphenyl-4-ylmethyl)-acetamide bitartrate |

| Ex. No. | Precursors | Structure | Name |
|---|---|---|---|
| 101 | Int. E11<br>Int. A2 | 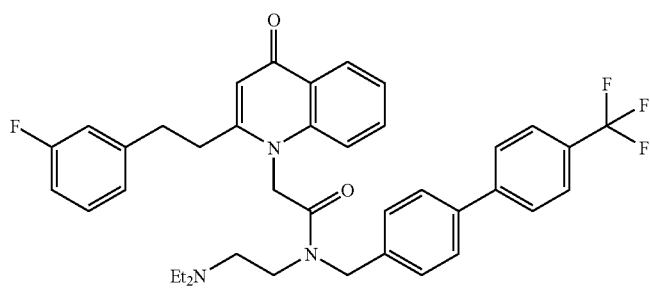 | N-(2-Diethylaminoethyl)-2-[2-(2-(3-fluorophenyl)ethyl)-4-oxo-4H-quinolin-1-yl]-N-(4'-trifluoromethylbiphenyl-4-ylmethyl)-acetamide bitartrate |

Example 105

N-(piperidin-4-yl)-2-[2-(2,3-difluorobenzylthio)-4-oxo-4H-quinolin-1-yl]-N-(4'-trifluoromethylbiphenyl-4-ylmethyl)acetamide bitartrate

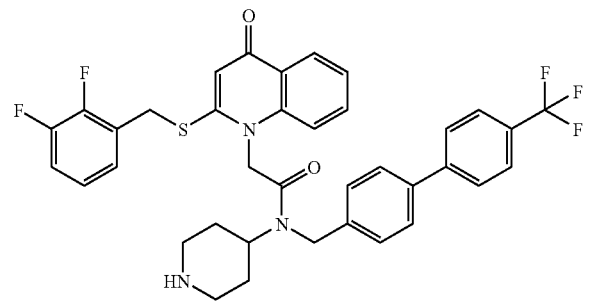

To intermediate F1 (0.55 g) in dichloromethane (6 ml) was added trifluoroacetic acid (2.5 ml) at room temperature. The mixture was stirred for 2 h, the solvent removed under reduced pressure and diethyl ether added The solid so formed was filtered and washed with diethyl ether to give a solid that was partitioned between dilute sodium bicarbonate and dichloromethane. The aqueous layer was extracted with further dichloromethane and the combined organic layers dried over $K_2CO_3$, filtered and evaporated under reduced pressure to a solid (0.42 g). This free base (0.42 g) was dissolved in methanol (10 ml), tartaric acid (0.044 g) was added, the mixture stirred for 5 min then evaporated under reduced pressure. Trituration with ether gave the bitartrate salt as an off-white solid (0.46 g). $^1$H-NMR (d6 DMSO, rotamer mixture) δ 1.6–2.05 (4H, m), 2.7–3.05 (2H, m), 3.1–3.4 (2H, m), 3.88 (2H, s), 4.1–5.8 (7H, br ms), 6.27+6.32 (1H, 2×s), 7.05+7.55 (6H, m), 7.55–7.95 (8H, m), 8.14 (1H, dt); MS (APCI+) found (M+1)=678. $C_{37}H_{32}F_5N_3O_2S$ requires 677.

The following examples were prepared by the method of Example 105:

| Ex. No. | Precursors | Structure | Name |
|---|---|---|---|
| 106 | Int. F2 | 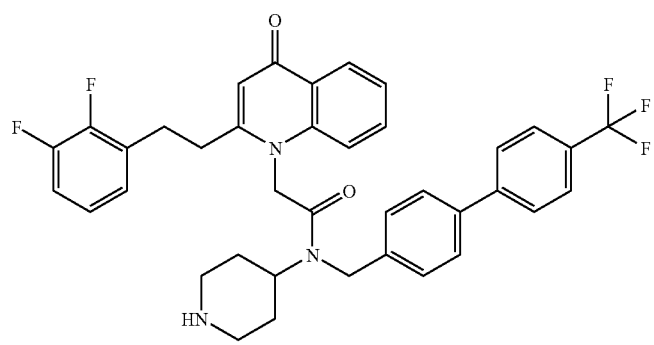 | N-(piperidin-4-yl)-2-[2-(2-(2,3-difluorophenyl)ethyl)-4-oxo-4H-quinolin-1-yl]-N-(4'-trifluoromethylbiphenyl-4-ylmethyl)-acetamide bitartrate |

-continued

| Ex. No. | Precursors | Structure | Name |
|---|---|---|---|
| 107 | Int. F3 | 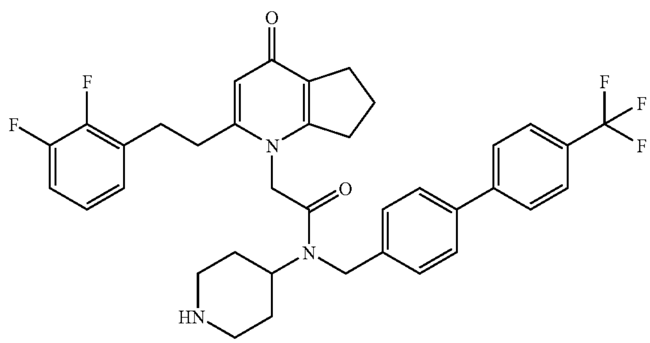 | N-(piperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate |
| 108 | Example 62 | 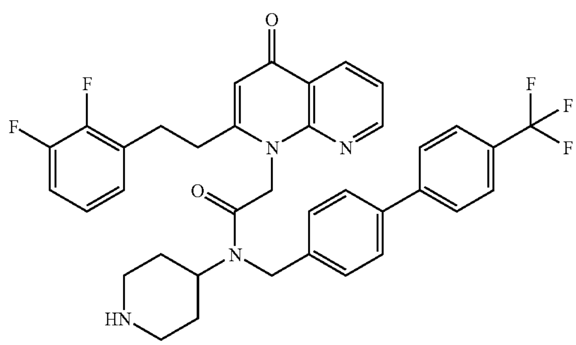 | N-(piperidin-4-yl)-2-[2-(2-(2,3-difluorophenyl)ethyl)-4-oxo-4H-[1,8]naphthyridin-1-yl]-N-(4'-trifluoromethylbiphenyl-4-yl-methyl)acetamide bitartrate |
| 109 | Example 96 | 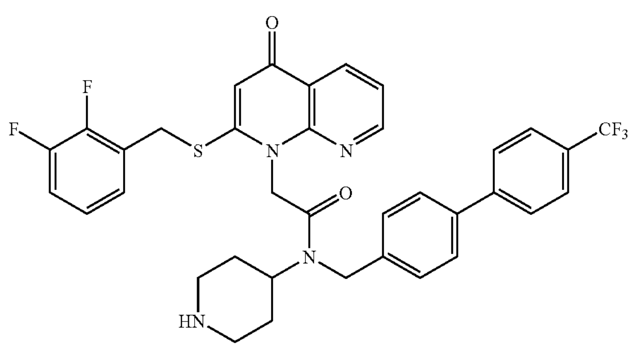 | N-(piperidin-4-yl)-2-[2-(2,3-difluorobenzylthio)-4-oxo-4H-[1,8]naphthyridin-1-yl]-N-4'-trifluoromethylbiphenyl-4-yl-methyl)acetamide trifluoroacetate |
| 110 | Int. F4 | 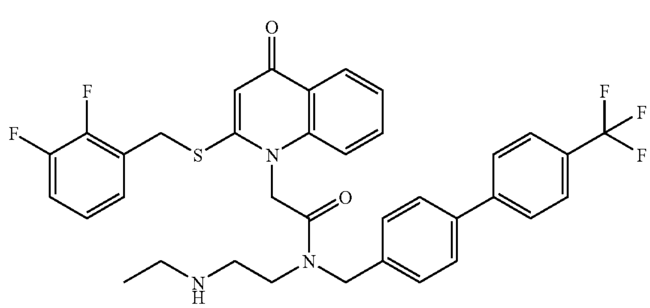 | N-(2-ethylaminoethyl)-2-[2-(2,3-difluorobenzylthio)-4-oxo-4H-quinolin-1-yl]-N-(4'-trifluoro-methylbiphenyl-4-ylmethyl)-acetamide |

| Ex. No. | Precursors | Structure | Name |
|---|---|---|---|
| 111 | Int. F5 | 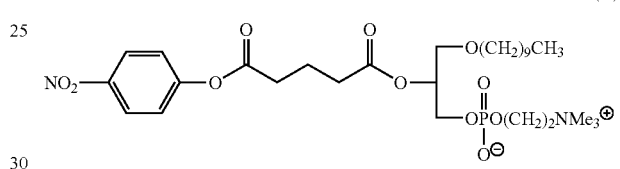 | N-(2-ethylaminoethyl)-2-[2-(2-(2,3-difluorophenyl)ethyl)-4-oxo-4H-quinolin-1-yl]-N-(4'-trifluoromethylbiphenyl-4-ylmethyl)-acetamide |

Example 115

N-(1-(2-hydroxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate

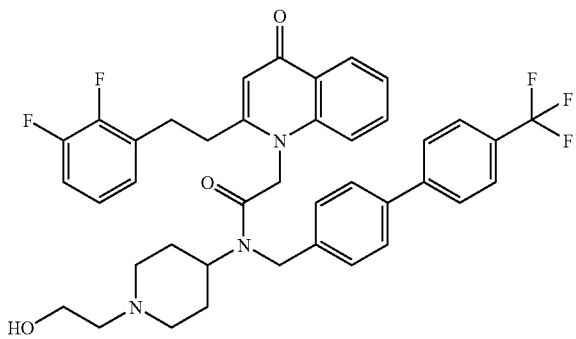

A mixture of Example 59 (0.18 g, 1 equiv), lithium borohydride (0.12 ml, 2M in THF, 1 equiv) and dry THF (2 ml) was heated at reflux under argon overnight, then a further 0.06 ml portion of lithium borohydride solution was added and heating continued for 4 h. Evaporation, aqueous workup and chromatography (silica, 0–10% methanol in dichloromethane) gave the title compound (0.06 g). The bitartrate was prepared as in example 1. $^1$H-NMR (DMSO, rotamer mixture) δ 1.5–2.1 (4H, m), 2.5–3.65 (12H, m), 4.15 (2H, s), 3.85–5.8 (5H, br m), 6.01+6.06 (1H, 2×s), 7.0–7.95 (14H, m), 8.05–8.2 (1H, m); MS (APCI+) found (M+1)= 704. $C_{40}H_{38}F_5N_3O_3$ requires 703.

Biological Data

1. Screen for Lp-PLA$_2$ Inhibition.

Enzyme activity was determined by measuring the rate of turnover of the artificial substrate (A) at 37 C in 50 mM HEPES (N-2-hydroxyethylpiperazine-N'-2-ethanesulphonic acid) buffer containing 150 mM NaCl, pH 7.4.

(A)

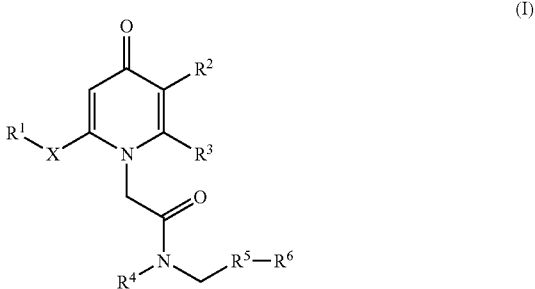

Assays were performed in 96 well titre plates.

Recombinant LpPLA2 was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay plates of compound or vehicle plus buffer were set up using automated robotics to a volume of 170 μl. The reaction was initiated by the addition of 20 μl of 10× substrate (A) to give a final substrate concentration of 20 μM and 10 μl of diluted enzyme to a final 0.2 nM LpPLA2.

The reaction was followed at 405 nm and 37° C. for 20 minutes using a plate reader with automatic mixing. The rate of reaction was measured as the rate of change of absorbance.

Results

The compounds described in the Examples were tested as described above and had IC$_{50}$ values in the range <0.1 to 100 nM.

What is claimed is:

1. A compound of formula (I):

(I)

in which:
- R₁ is an aryl group, optionally substituted by 1, 2, 3 or 4 substituents which may be the same or different selected from $C_{(1-6)}$alkyl, $C_{(1-6)}$alkoxy, $C_{(1-6)}$alkylthio, hydroxy, halogen, CN, mono to perfluoro-$C_{(1-4)}$alkyl, mono to perfluoro-$C_{(1-4)}$alkoxyaryl, and aryl$C_{(1-4)}$alkyl;
- $R^2$ is halogen, $C_{(1-3)}$alkyl, $C_{(1-3)}$alkoxy, hydroxy$C_{(1-3)}$alkyl, $C_{(1-3)}$alkylthio, $C_{(1-3)}$alkylsulphinyl, amino$C_{(1-3)}$alkyl, mono- or di-$C_{(1-3)}$alkylamino$C_{(1-3)}$alkyl, $C_{(1-3)}$alkylcarbonylamino$C_{(1-3)}$alkyl, $C_{(1-3)}$alkoxy$C_{(1-3)}$alkylcarbonylamino$C_{(1-3)}$alkyl, $C_{(1-3)}$alkylsulphonylamino$C_{(1-3)}$alkyl, $C_{(1-3)}$alkylcarboxy, or $C_{(1-3)}$alkylcarboxy$C_{(1-3)}$alkyl, or
- $R^3$ is hydrogen, halogen, $C_{(1-3)}$alkyl, or hydroxy$C_{1-3)}$alkyl; or
- $R^2$ and $R^3$ together with the pyridone ring carbon atoms to which they are attached form a fused 5-or 6-membered carbocyclic ring; or
- $R^2$ and $R^3$ together with the pyridone ring carbon atoms to which they are attached form a fused benzo or heteroaryl ring optionally substituted by 1, 2, 3 or 4 substituents which may be the same or different selected from halogen, $C_{(1-4)}$alkyl, cyano, $C_{(1-3)}$alkoxy$C_{1-3)}$alkyl, $C_{1-4)}$alkoxy or $C_{(1-4)}$alkylthio, and mono to perfluoro-$C_{(1-4)}$alkyl;
- $R^4$ is hydrogen, $C_{(1-6)}$alkyl which may be unsubstituted or substituted by 1, 2 or 3 substituents selected from hydroxy, halogen, $OR^7$, $COR^7$, carboxy, $COOR^7$, $CONR^9R^{10}$, $NR^9R^{10}$, $NR^7COR^8$, mono- or di-(hydroxy$C_{(1-6)}$alkyl)amino and N-hydroxy$C_{(1-6)}$alkyl-N—$C_{(1-6)}$alkylamino; or
- $R^4$ is Het-$C_{(0-4)}$alkyl in which Het is a 5- to 7-membered heterocyclyl ring comprising N and optionally O or S, and in which N may be substituted by $COR^7$, $COOR^7$, $CONR^9R^{10}$, or $C_{(1-6)}$alkyl optionally substituted by 1, 2 or 3 substituents selected from hydroxy, halogen, $OR^7$, $COR^7$, carboxy, $COOR^7$, $CONR^9R^{10}$ or $NR^9R^{10}$, for instance, piperidin-4-yl, pyrrolidin-3-yl;
- $R^5$ is an aryl or a heteroaryl ring optionally substituted by 1, 2, 3 or 4 substituents which may be the same or different selected from $C_{(1-6)}$alkyl, $C_{(1-6)}$alkoxy, $C_{(1-6)}$alkylthio, aryl$C_{(1-6)}$alkoxy, hydroxy, halogen, CN, $COR^7$, carboxy, $COOR^7$, $NR^7COR^8$, $CONR^9R^{10}$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy;
- $R^6$ is an aryl or a heteroaryl ring which is further optionally substituted by 1, 2, 3 or 4 substituents which may be the same or different selected from $C_{(1-6)}$alkyl, $C_{(1-6)}$alkoxy, $C_{(1-6)}$alkylthio, $C_{(1-6)}$alkylsulfonyl, aryl$C_{(1-6)}$alkoxy, hydroxy, halogen, CN, $COR^7$, carboxy, $COOR^7$, $CONR^9R^{10}$, $NR^7COR^8$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy, or $C_{(5-10)}$alkyl;
- $R^7$ and $R^8$ are independently hydrogen or $C_{(1-12)}$alkyl;
- $R^9$ and $R^{10}$ which may be the same or different is each selected from hydrogen, or $C_{(1-12)}$alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylcarboxy, aryl, e.g. phenyl, or aralkyl, e.g benzyl, for instance morpholine or piperazine; and
- X is a $C_{(2-4)}$alkylene group optionally substituted by 1, 2 or 3 substituents selected from methyl and ethyl; CH=CH; $(CH_2)_nS$ or $(CH_2)_nO$ where n is 1, 2 or 3;

or a pharmaceutically acceptable salt thereof.

2. A compound of formula (I) as claimed in claim 1 in which $R^1$ is phenyl optionally substituted by halogen, $C_{(1-6)}$alkyl, trifluoromethyl, $C_{(1-6)}$alkoxy.

3. A compound of formula (I) as claimed in claim 1 in which $R^2$ and $R^3$ together with the pyridone ring carbon atoms to which they are attached form a fused thiazolyl ring substituted by methyl, cyclopentenyl, or a fused benzo, pyrido, thieno or pyrazolo ring.

4. A compound of formula (I) as claimed in claim 1 in which $R^4$ is selected from the group consisting of 2-(diethylamino)ethyl, 1-ethyl-piperidin-4-yl, 1-(2-methoxyethyl)piperidin-4-yl, 1-methylpiperidin-4-yl and 1-ethylpyrrolidin-3-yl.

5. A compound of formula (I) as claimed in claim 1 in which $R^5$ is phenyl.

6. A compound of formula (I) as claimed in claim 1 in which $R^6$ is phenyl substituted by trifluoromethyl or ethyl in the 4-position.

7. A compound of formula (I) as claimed in claim 1 in which $R^5$ and $R^6$ together form a 4-(phenyl)phenyl or a 2-(phenyl)pyridinyl substituent in which the remote phenyl ring may be optionally substituted by halogen or trifluoromethyl.

8. A compound of formula (I) as claimed in claim 1 in which X is $C_{(2-4)}$alkylene or $CH_2S$.

9. A compound of formula (I) as claimed in claim 1 in which $R^1$ is phenyl substituted by 2,3-difluoro; $R^2$ and $R^3$, together with the pyridone ring carbon atoms to which they are attached, form a cyclopentenyl ring, or a fused benzo or pyrido ring; $R^4$ is 2-(diethylamino)ethyl, 1-ethyl-piperidin-4-yl, 1-(2-methoxyethyl)piperidin-4-yl, 1-methylpiperidin-4-yl or 1-ethylpyrrolidin-3-yl; $R^5$ is phenyl; $R^6$ is phenyl substituted by ethyl or trifluoromethyl in the 4-position; and X is $CH_2S$.

10. A compound of formula (I) as claimed in claim 1 in which $R^1$ is phenyl substituted by 2,3-difluoro; $R^2$ and $R^3$, together with the pyridone ring carbon atoms to which they are attached, form a fused thiazolyl ring substituted by methyl, or a benzo or pyrido ring; $R^4$ is 2-(diethylamino)ethyl, 1-ethyl-piperidin-4-yl, 1-(2-methoxyethyl)piperidin-4-yl, 1-methylpiperidin-4-yl or 1-ethylpyrrolidin-3-yl; $R^5$ is phenyl; $R^6$ is phenyl substituted by trifluoromethyl in the 4-position; and X is $(CH_2)_2$.

11. A compound of formula (I) as claimed in claim 1 in which $R^1$ is phenyl substituted by 2,3-difluoro; $R^2$ and $R^3$, together with the pyridone ring carbon atoms to which they are attached, form a fused benzo or pyrido ring; $R^4$ is 1-(2-methoxyethyl)piperidin-4-yl; $R^5$ and $R^6$ together form a 4-(phenyl)phenyl substituent in which the remote phenyl ring is substituted by trifluoromethyl, preferably at the 4-position; and X is $CH_2S$ or $(CH_2)_2$.

12. A compound of formula (I) as claimed in claim 1 which is:
- N-(2-diethylaminoethyl)-2-[2-(2,3-difluorobenzylthio)-4-oxo-4H-quinolin-1-yl]-N-(4'-trifluoromethylbiphenyl-4-ylmethyl)acetamide bitartrate;
- N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide;
- N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;
- N-(2-diethylaminoethyl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(1-methylpiperidin-4-yl)-2-[2-(2,3-difluoroben-zylthio)-4-oxo-4H-quinolin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide;

N-(1-(2-methoxyethyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl )-2-[2-(2,3-difluorobenzylthio)-4-oxo-4H-quinolin-1-yl]-N-(4'-ethylbiphenyl-4-ylmethyl)acetamide bitartrate;

N-(1-ethylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

(±)N-(1-ethylpyrrolidin-3-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

(±)N-(1-ethylpyrrolidin-3-yl )-2-[2-(2,3-difluorobenzylthio)-4-oxo-4H-quinolin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide dihydrochloride;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide mono para-toluenesulphonate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide monohydrochloride;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide dihydrochloride;

N-(2-diethylaminoethyl)-2-[2-(4-fluorobenzylthio)-4-oxo-4H-quinolin-1-yl]-N-(4'-trifluoromethylbiphenyl-4-ylmethyl)acetamide bitartrate;

N-(2-diethylaminoethyl)-2-[2-(4-fluorobenzylthio)-4-oxo-5,6-trimethylenepyridin-1-yl]-N-(4'-trifluoromethyl-biphenyl-4-ylmethyl)acetamide bitartrate;

N-(2-diethylaminoethyl)-2-[2-(2,3-difluorobenzylthio)-4-oxo-5,6-trimethylenepyridin-1-yl]-N-(4'-trifluoromethyl-biphenyl-4-ylmethyl)acetamide bitartrate;

N-(2-diethylaminoethyl)-2-[2-(4-fluorophenyl)ethyl)-4-oxo-4H-quinolin-1-yl]-N-(4'-trifluoromethylbiphenyl-4-ylmethyl)acetamide;

N-(2-diethylaminoethyl)-2-[2-(2-(3,4-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2-fluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(3-chlorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide bitartrate;

N-(1-ethylpiperidin-4-yl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide;

N-(1-ethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-pyrrolidin-1-ylethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-pipiperidin-1-ylethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2,3-difluorobenzylthio)7-fluoro-4-oxo-4H-quinolin-1-yl]-N-(4'-trifluoromethylbiphenyl-4-ylmethyl)acetamide bitartrate;

N-(2-diethylaminoethyl)-5-[2-(2-(2,3-difluorophenyl)ethyl)-2-methyl-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[2-(2-(2,3-difluorophenyl)ethyl)-5,6-dimethyl-4-oxo-4H-pyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-5-ethyl-4-oxo-4H-pyridin-1-yl]-N-(4'-trifluoromethylbiphenyl-4-ylmethyl)acetamide bitartrate;

N-(1-(2-methoxyethyl)piperidin-4-yl)-2-[2-(2,3-difluorophenyl)ethyl)-4-oxo-4H-quinolin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-thieno[3,4-b]pyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(2-pyrrolidin-1-ylethyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)acetamide bitartrate;

N-(1-isopropylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-ylmethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2,3-difluorobenzylthio)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[5-(2-(2,3-difluorobenzylthio)-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-ethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-ethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-isopropylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-isopropylbiphenyl-4-ylmethyl)acetamide bitartrate;

N-(2-diethylaminoethyl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-methylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-methylbiphenyl-4-ylmethyl)acetamide bitartrate;

N-(1-ethoxycarbonylmethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-dimethylbiphenyl-4-ylmethyl)acetamide bitartrate;

N-(1-(t-butoxycarbonyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-difluorobiphenyl-4-ylmethyl)acetamide bitartrate;

N-(2-diethylaminoethyl)-2-[6-(2,3-difluorobenzylthio)-4-oxo-4H-thieno-[2,3-b]pyridin-7-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2-(2,3,4-trifluorophenyl-ethyl)-4-oxo-4H-quinolin-1-yl]-N-(4'-trifluoromethylbiphenyl-4-ylmethyl)acetamide bitartrate;

N-(2-diethylaminoethyl)-2-[6-(2,3-difluorobenzylthio)-2-methyl-4-oxo-2,4-dihydropyrazolo[3,4-b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-ethyl-4-oxo-2,4-dihydropyrazolo[3,4-b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-isopropyl-4-oxo-2,4-dihydropyrazolo[3,4-b]pyridin-7-yl]-N-(4'-trifluoromethylbiphenyl-4-ylmethyl)acetamide bitartrate;

N-(1-ethylpiperidin-4-yl)-2-[2-(2-(2,3-difluorophenyl)ethyl)-4-oxo-4H-quinolin-1-yl]-N-(4'-ethylbiphenyl-4-ylmethyl)acetamide bitartrate;

N-(1-isopropylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(1-(2-methoxyethyl)piperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(1-ethylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-ethylpiperidin-4-yl)-2-[5-(2-(2,3-difluorophenyl)ethyl)-2-methyl-7-oxo-2,7-dihydropyrazolo[4,3-b]pyridin-4-yl]-N-(4'-trifluoromethylbiphenyl-4-ylmethyl)acetamide bitartrate;

N-(1-ethylpiperidin-4-yl)-2-[5-(2-(2,3-difluorophenyl)ethyl)-1-methyl-7-oxo-1,7-dihydropyrazolo[4,3-b]pyridin-4-yl]-N-(4'-trifluoromethylbiphenyl-4-ylmethyl)acetamide bitartrate;

N-(1-ethylpipiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-ethylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-methylpipiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(1-isopropylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-5,6-tetramethylenepyridin-1-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-4H-quinolin-1-yl]-N-(4'-chlorobiphenyl-4-ylmethyl)acetamide bitartrate;

N-(1-methylpipiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-ethylpiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-(2-methoxyethyl)pipiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-isopropylpipiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(2-diethylaminoethyl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)acetamide bitartrate;

N-(1-(t-butoxycarbonyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide;

N-(1-ethylpipiperidin-4-yl)-2-[6-(2-(2,3-difluorophenyl)ethyl)-2-(2-methoxyethyl)-4-oxo-4H-pyrazolo[3,4-b]pyridin-7-yl]-N-(4'-trifluoromethylbiphenyl-4-ylmethyl)acetamide bitartrate;

N-(2-diethylaminoethyl)-2-[4-oxo-2-(2-(2,3,4-trifluorophenyl)ethyl)-4H-quinolin-1-yl]-N-(4'-trifluoromethyl-biphenyl-4-ylmethyl)acetamide bitartrate;

N-(2-diethylaminoethyl)-2-[2-(2-(2,4-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(3-fluorophenyl)ethyl)-4-oxo-4H-quinolin-1-yl]-N-(4'-trifluoromethylbiphenyl-4-ylmethyl)acetamide bitartrate;

N-(pipiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(pipiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(pipiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(pipiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(pipiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide trifluoroacetate;

N-(2-ethylaminoethyl)-2-[2-(2,3-difluorobenzylthio)-4-oxo-4H-quinolin-1-yl]-N-(4'-trifluoromethylbiphenyl-4-ylmethyl)acetamide;

N-(2-ethylaminoethyl)-2-[2-(2-(2,3-difluorophenyl)ethyl)-4-oxo-4H-quinolin-1-yl]-N-(4'-trifluoromethyl-biphenyl-4-ylmethyl)acetamide;

N-(1-(2-hydroxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

or the free base thereof, or or another pharmaceutically acceptable salt thereof.

13. A compound of formula (I) as defined in claim 1 which is:

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide;

or a pharmaceutically acceptable salt thereof.

14. A pharmaceutical composition comprising a compound of formula (I) as claimed in claim 1 and a pharmaceutically acceptable carrier.

15. A process for preparing a compound of formula (I) as defined in claim 1 which process comprises reacting an acid compound of formula (II):

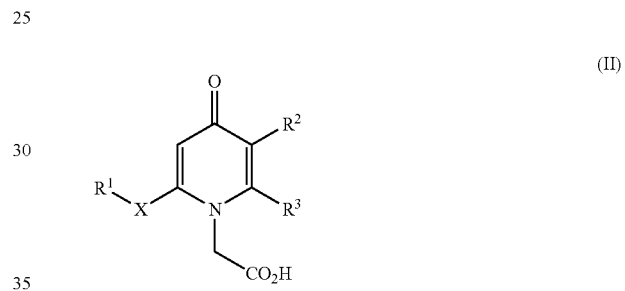

in which X, $R^1$, $R^2$ and $R^3$ are as defined in claim 1 for formula (I), with an amine compound of formula (III):

in which $R^4$, $R^5$ and $R^6$ are as defined in claim 1 for formula (I); under amide forming conditions.

16. A pharmaceutical composition comprising N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)-acetamide, or a pharmaceutically acceptable salt thereof, and a pharmaceutically acceptable carrier.

17. A method of treating atherosclerosis which comprises administering to a human in need thereof an effective amount of a compound according to claim 1 or a salt thereof, alone or in admixture with a pharmaceutically acceptable carrier.

18. The method of claim 17 wherein the compound is N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide, or a pharmaceutically acceptable salt thereof.

19. A method for treating atherosclerosis which comprises administering to a human in need thereof an effective amount of a compound according to claim 1 or a salt thereof, alone, or combined with a statin, in admixture with a pharmaceutically acceptable carrier.

20. A method for treating atherosclerosis which comprises administering to a human in need thereof an effective amount of N-(1-(2-methoxyethyl)piperidin-4-yl )-2-[2-(2,3-difluorobenzylthio)-4-oxo-4H-quinolin-1-yl]-N-(4'-trifluoromethylbiphenyl-4-yl methyl)acetamide or a salt thereof and a statin, both or either being administered in essentially pure form or in admixture with a pharmaceutically acceptable carrier.

* * * * *